(12) United States Patent
Otto et al.

(10) Patent No.: US 8,211,445 B2
(45) Date of Patent: Jul. 3, 2012

(54) **PSM PEPTIDES AS VACCINE TARGETS AGAINST METHICILLIN-RESISTANT *STAPHYLOCOCCUS***

(75) Inventors: Michael Otto, Washington, DC (US); Rong Wang, Hamilton, MT (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 41 days.

(21) Appl. No.: 12/631,253

(22) Filed: Dec. 4, 2009

(65) Prior Publication Data

US 2010/0119477 A1      May 13, 2010

Related U.S. Application Data

(63) Continuation-in-part of application No. PCT/US2008/063119, filed on May 8, 2008.

(60) Provisional application No. 60/933,573, filed on Jun. 6, 2007, provisional application No. 60/983,141, filed on Oct. 26, 2007.

(51) Int. Cl.
*A61K 39/085*      (2006.01)
(52) U.S. Cl. .............. 424/243.1; 424/185.1; 424/190.1; 424/193.1; 530/300; 530/326
(58) Field of Classification Search .................... None
See application file for complete search history.

(56) References Cited

FOREIGN PATENT DOCUMENTS

| EP | 0597110 | 5/1994 |
|---|---|---|
| WO | WO 2007/113499 | 10/2007 |
| WO | WO 2008/103751 | 8/2008 |

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Kuroda et al (Lancet. 2001. 357: 1225-1240.*
Baba et al (Lancet. 2002. 367: 731-9.*
Cogen et al., "Selective Antimicrobial Action Is Provided by Phenol-Soluble Modulins Derived from *Staphylococcus epidermidis*, a Normal Resident of the Skin," *J. Invest. Dermatol.*, e-published ahead of print, 2009.
Dürr et al., "Neutrophil chemotaxis by pathogen-associated molecular patterns—formylated peptides are crucial but not the sole neutrophil attractants produced by *Staphylococcus aureus*," *Cellular Microbiology*, vol. 8, No. 2, pp. 207-217, 2006.
Gill et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain," *Journal of Bacteriology*, vol. 187, No. 7, pp. 2426-2438, 2005.
Klevens et al., "Invasive Methicillin-Resistant *Staphylococcus aureus* Infections in the United States," *JAMA*, vol. 298, No. 15, pp. 1763-1771, 2007.
Li et al., "Evolution of virulence in epidemic community-associated methicillin-resistant *Staphylococcus aureus*," *PNAS*, vol. 106, No. 14, pp. 5883-5888, 2009.
Otto et al., "Activity of *Staphylococcus epidermidis* Phenol-Soluble Modulin Peptides Expressed in *Staphylococcus carnosus*," *Journal of Infectious Diseases*, vol. 190, pp. 748-755, 2004.
Queck et al., "RNAIII-Independent Target Gene Control by the *agr* Quorum-Sensing System: Insight into the Evolution of Virulence Regulation in *Staphylococcus aureus*," *Molecular Cell*, vol. 32, pp. 150-158, 2008.
Queck et al., "Mobile Genetic Element-Encoded Cytolysin Connects Virulence to Methicillin Resistance in MRSA," *PLoS Pathogens*, vol. 5, No. 7, e1000533, 2009.
Veldkamp et al., "Staphylococcal Culture Supernates Stimulate Human Phagocytes," *Inflammation*, vol. 21, No. 5, pp. 541-551, 1997.
Wang et al., "Identification of novel cytolytic peptides as key virulence determinants for community-associated MRSA," *Nature Medicine*, vol. 13, No. 12, pp. 1510-1514, 2007.

* cited by examiner

*Primary Examiner* — Jennifer Graser
(74) *Attorney, Agent, or Firm* — Klarquist Sparkman, LLP.

(57) ABSTRACT

This disclosure concerns compositions and methods for the treatment and inhibition of infectious disease, particularly methicillin-resistant *Staphylococcus*. In certain embodiments, the disclosure concerns immunogenic peptides, for instance PSM peptides, which can be used to induce protective immunity against methicillin-resistant *Staphylococcus*. Also disclosed are methods of detecting methicillin-resistant *staphylococcus* in a sample, and methods of diagnosing methicillin-resistant *staphylococcus* in a subject.

16 Claims, 33 Drawing Sheets

```
                 1         10        20        30        40
PSMα1  fMGIIAGIIKVIKSLIEQFTGK        (SEQ ID NO: 1)
PSMα2  fMGIIAGIIKFIKGLIEKFTGK        (SEQ ID NO: 2)
PSMα3  fMEFVAKLFKFFKDLLGKFLGNN       (SEQ ID NO: 3)
PSMα4  fMAIVGTIIKIIKAIIDIFAK         (SEQ ID NO: 4)
δ-Toxin fMAQDIISTISDLVKWIIDTVNKFTKK  (SEQ ID NO: 5)
PSMβ1  fMEGLFNAIKDTVTAAINNDGAKLGTSIVSIVENGVGLLGKLFGF  (SEQ ID NO: 6)
PSMβ2  fMTGLAEAIANTVQAAQQHDSVKLGTSIVDIVANGVGLLGKLFGF  (SEQ ID NO: 7)
```

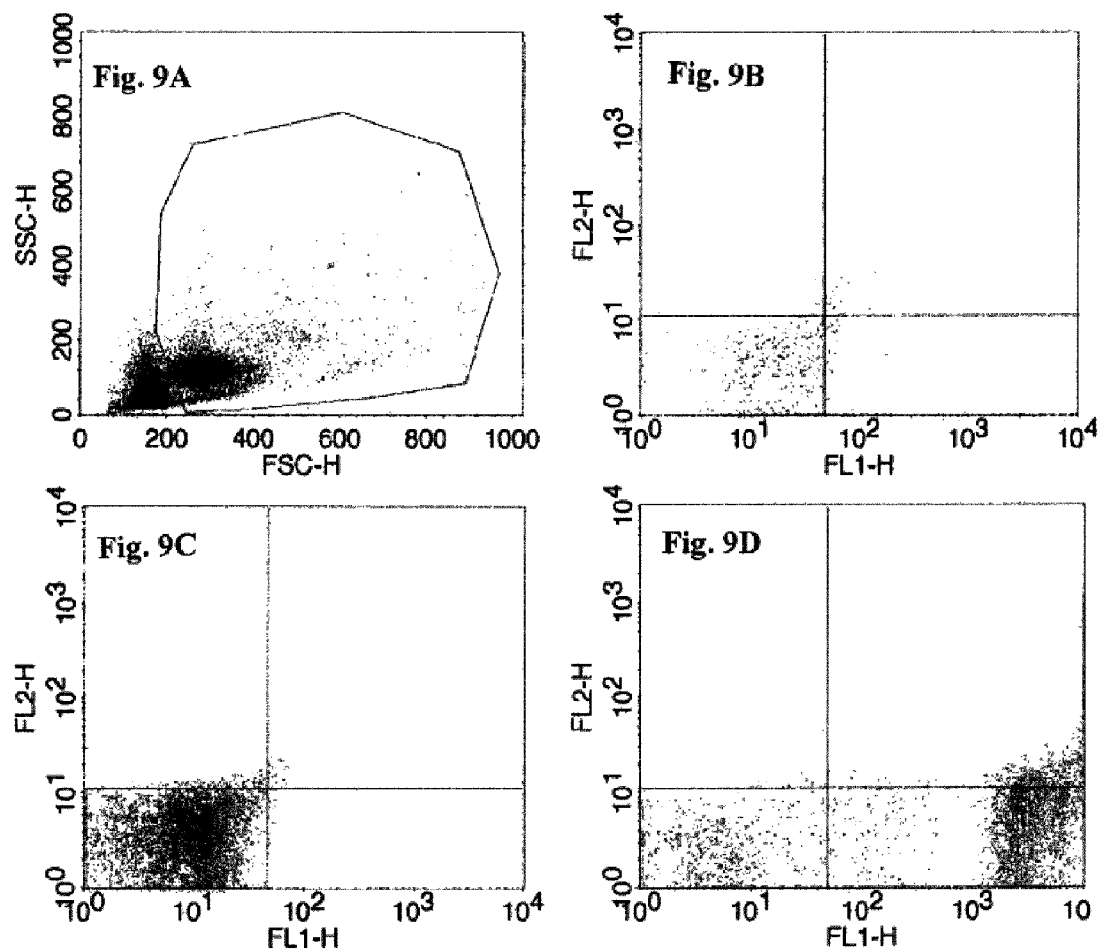

Fig. 17

Antibody (N-formylated PSM) mediated phagocytosis (LAC)

SEQUENCE LISTING

<160> NUMBER OF SEQ ID NOS: 33

<210> SEQ ID NO 1
<211> LENGTH: 21
<212> TYPE: PRT
<213> ORGANISM: S. aureus

<400> SEQUENCE: 1

Met Gly Ile Ile Ala Gly Ile Ile Lys Val Ile Lys Ser Leu Ile Glu
1               5                   10                  15

Gln Phe Thr Gly Lys
            20

<210> SEQ ID NO 2
<211> LENGTH: 21
<212> TYPE: PRT
<213> ORGANISM: S. aureus

-continued

```
<400> SEQUENCE: 2

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 3
<211> LENGTH: 22
<212> TYPE: PRT
<213> ORGANISM: S. aureus

<400> SEQUENCE: 3

Met Glu Phe Val Ala Lys Leu Phe Lys Phe Phe Lys Asp Leu Leu Gly
1               5                   10                  15

Lys Phe Leu Gly Asn Asn
            20

<210> SEQ ID NO 4
<211> LENGTH: 20
<212> TYPE: PRT
<213> ORGANISM: S. aureus

<400> SEQUENCE: 4

Met Ala Ile Val Gly Thr Ile Ile Lys Ile Ile Lys Ala Ile Ile Asp
1               5                   10                  15

Ile Phe Ala Lys
            20

<210> SEQ ID NO 5
<211> LENGTH: 26
<212> TYPE: PRT
<213> ORGANISM: S. aureus

<400> SEQUENCE: 5

Met Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25

<210> SEQ ID NO 6
<211> LENGTH: 44
<212> TYPE: PRT
<213> ORGANISM: S. aureus

<400> SEQUENCE: 6

Met Glu Gly Leu Phe Asn Ala Ile Lys Asp Thr Val Thr Ala Ala Ile
1               5                   10                  15

Asn Asn Asp Gly Ala Lys Leu Gly Thr Ser Ile Val Ser Ile Val Glu
            20                  25                  30

Asn Gly Val Gly Leu Leu Gly Lys Leu Phe Gly Phe
        35                  40

<210> SEQ ID NO 7
<211> LENGTH: 44
<212> TYPE: PRT
<213> ORGANISM: S. aureus

<400> SEQUENCE: 7

Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30
```

Asn Gly Val Gly Leu Leu Gly Lys Leu Phe Gly Phe
            35                  40

<210> SEQ ID NO 8
<211> LENGTH: 21
<212> TYPE: PRT
<213> ORGANISM: S. aureus
<220> FEATURE:
<221> NAME/KEY: MISC_FEATURE
<222> LOCATION: (10)..(10)
<223> OTHER INFORMATION: Xaa can be Val or Phe
<220> FEATURE:
<221> NAME/KEY: MISC_FEATURE
<222> LOCATION: (13)..(13)
<223> OTHER INFORMATION: Xaa can be Ser or Gly
<220> FEATURE:
<221> NAME/KEY: MISC_FEATURE
<222> LOCATION: (17)..(17)
<223> OTHER INFORMATION: Xaa can be Gln or Lys

<400> SEQUENCE: 8

Met Gly Ile Ile Ala Gly Ile Ile Lys Xaa Ile Lys Xaa Leu Ile Glu
1               5                   10                  15

Xaa Phe Thr Gly Lys
            20

<210> SEQ ID NO 9
<211> LENGTH: 22
<212> TYPE: PRT
<213> ORGANISM: Staphylococcus aureus

<400> SEQUENCE: 9

Met Asp Phe Thr Gly Val Ile Thr Ser Ile Ile Asp Leu Ile Lys Thr
1               5                   10                  15

Cys Ile Gln Ala Phe Gly
            20

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide primer PSMErev1

<400> SEQUENCE: 10
caagacttgc attcaggctt tcggtgaatt ctttc                          35

<210> SEQ ID NO 11
<211> LENGTH: 64
<212> TYPE: DNA
<213> ORGANISM: Artificial Sequence
<220> FEATURE:
<223> OTHER INFORMATION: Synthetic oligonucleotide primer PSMEatt1

<400> SEQUENCE: 11
ggggacaagt ttgtacaaaa aagcaggctg gaagttttgt gctttataat gaacgggagc  60
aagc                                                              64

<210> SEQ ID NO 12
<211> LENGTH: 32
<212> TYPE: DNA
<213> ORGANISM: Artificial Sequence
<220> FEATURE:
<223> OTHER INFORMATION: Synthetic oligonucleotide primer PSMErev2

<400> SEQUENCE: 12

```
caccagtgaa ttccatatgc ataccctctt tc                           32
```

<210> SEQ ID NO 13
<211> LENGTH: 58
<212> TYPE: DNA
<213> ORGANISM: Artificial Sequence
<220> FEATURE:
<223> OTHER INFORMATION: Synthetic oligonucleotide primer PSMEatt2

<400> SEQUENCE: 13

```
ggggaccact ttgtacaaga aagctgggtg taccacctag caaagttgca aatttgac   58
```

<210> SEQ ID NO 14
<211> LENGTH: 22
<212> TYPE: PRT
<213> ORGANISM: Staphylococcus aureus

<400> SEQUENCE: 14

```
Met Ala Phe Val Ala Lys Leu Phe Lys Phe Phe Lys Asp Leu Leu Gly
1               5                   10                  15

Lys Phe Leu Gly Asn Asn
            20
```

<210> SEQ ID NO 15
<211> LENGTH: 22
<212> TYPE: PRT
<213> ORGANISM: Staphylococcus aureus

<400> SEQUENCE: 15

```
Met Glu Ala Val Ala Lys Leu Phe Lys Phe Phe Lys Asp Leu Leu Gly
1               5                   10                  15

Lys Phe Leu Gly Asn Asn
            20
```

<210> SEQ ID NO 16
<211> LENGTH: 22
<212> TYPE: PRT
<213> ORGANISM: Staphylococcus aureus

<400> SEQUENCE: 16

```
Met Glu Phe Ala Ala Lys Leu Phe Lys Phe Phe Lys Asp Leu Leu Gly
1               5                   10                  15

Lys Phe Leu Gly Asn Asn
            20
```

<210> SEQ ID NO 17
<211> LENGTH: 22
<212> TYPE: PRT
<213> ORGANISM: Staphylococcus aureus

<400> SEQUENCE: 17

```
Met Glu Phe Val Ala Ala Leu Phe Lys Phe Phe Lys Asp Leu Leu Gly
1               5                   10                  15

Lys Phe Leu Gly Asn Asn
            20
```

<210> SEQ ID NO 18
<211> LENGTH: 22
<212> TYPE: PRT
<213> ORGANISM: Staphylococcus aureus

<400> SEQUENCE: 18

```
Met Glu Phe Val Ala Lys Ala Phe Lys Phe Phe Lys Asp Leu Leu Gly
1               5                   10                  15
```

Lys Phe Leu Gly Asn Asn
            20

<210> SEQ ID NO 19
<211> LENGTH: 22
<212> TYPE: PRT
<213> ORGANISM: Staphylococcus aureus

<400> SEQUENCE: 19

Met Glu Phe Val Ala Lys Leu Ala Lys Phe Phe Lys Asp Leu Leu Gly
1               5                   10                  15

Lys Phe Leu Gly Asn Asn
            20

<210> SEQ ID NO 20
<211> LENGTH: 22
<212> TYPE: PRT
<213> ORGANISM: Staphylococcus aureus

<400> SEQUENCE: 20

Met Glu Phe Val Ala Lys Leu Phe Ala Phe Phe Lys Asp Leu Leu Gly
1               5                   10                  15

Lys Phe Leu Gly Asn Asn
            20

<210> SEQ ID NO 21
<211> LENGTH: 22
<212> TYPE: PRT
<213> ORGANISM: Staphylococcus aureus

<400> SEQUENCE: 21

Met Glu Phe Val Ala Lys Leu Phe Lys Ala Phe Lys Asp Leu Leu Gly
1               5                   10                  15

Lys Phe Leu Gly Asn Asn
            20

<210> SEQ ID NO 22
<211> LENGTH: 22
<212> TYPE: PRT
<213> ORGANISM: Staphylococcus aureus

<400> SEQUENCE: 22

Met Glu Phe Val Ala Lys Leu Phe Lys Phe Ala Lys Asp Leu Leu Gly
1               5                   10                  15

Lys Phe Leu Gly Asn Asn
            20

<210> SEQ ID NO 23
<211> LENGTH: 22
<212> TYPE: PRT
<213> ORGANISM: Staphylococcus aureus

<400> SEQUENCE: 23

Met Glu Phe Val Ala Lys Leu Phe Lys Phe Phe Ala Asp Leu Leu Gly
1               5                   10                  15

Lys Phe Leu Gly Asn Asn
            20

<210> SEQ ID NO 24
<211> LENGTH: 22
<212> TYPE: PRT
<213> ORGANISM: Staphylococcus aureus -continued

```
<400> SEQUENCE: 24

Met Glu Phe Val Ala Lys Leu Phe Lys Phe Phe Lys Ala Leu Leu Gly
1               5                   10                  15

Lys Phe Leu Gly Asn Asn
            20

<210> SEQ ID NO 25
<211> LENGTH: 22
<212> TYPE: PRT
<213> ORGANISM: Staphylococcus aureus

<400> SEQUENCE: 25

Met Glu Phe Val Ala Lys Leu Phe Lys Phe Phe Lys Asp Ala Leu Gly
1               5                   10                  15

Lys Phe Leu Gly Asn Asn
            20

<210> SEQ ID NO 26
<211> LENGTH: 22
<212> TYPE: PRT
<213> ORGANISM: Staphylococcus aureus

<400> SEQUENCE: 26

Met Glu Phe Val Ala Lys Leu Phe Lys Phe Phe Lys Asp Leu Ala Gly
1               5                   10                  15

Lys Phe Leu Gly Asn Asn
            20

<210> SEQ ID NO 27
<211> LENGTH: 22
<212> TYPE: PRT
<213> ORGANISM: Staphylococcus aureus

<400> SEQUENCE: 27

Met Glu Phe Val Ala Lys Leu Phe Lys Phe Phe Lys Asp Leu Leu Ala
1               5                   10                  15

Lys Phe Leu Gly Asn Asn
            20

<210> SEQ ID NO 28
<211> LENGTH: 22
<212> TYPE: PRT
<213> ORGANISM: Staphylococcus aureus

<400> SEQUENCE: 28

Met Glu Phe Val Ala Lys Leu Phe Lys Phe Phe Lys Asp Leu Leu Gly
1               5                   10                  15

Ala Phe Leu Gly Asn Asn
            20

<210> SEQ ID NO 29
<211> LENGTH: 22
<212> TYPE: PRT
<213> ORGANISM: Staphylococcus aureus

<400> SEQUENCE: 29

Met Glu Phe Val Ala Lys Leu Phe Lys Phe Phe Lys Asp Leu Leu Gly
1               5                   10                  15

Lys Ala Leu Gly Asn Asn
            20

<210> SEQ ID NO 30
```

```
<211> LENGTH: 22
<212> TYPE: PRT
<213> ORGANISM: Staphylococcus aureus

<400> SEQUENCE: 30

Met Glu Phe Val Ala Lys Leu Phe Lys Phe Phe Lys Asp Leu Leu Gly
1               5                   10                  15

Lys Phe Ala Gly Asn Asn
            20

<210> SEQ ID NO 31
<211> LENGTH: 22
<212> TYPE: PRT
<213> ORGANISM: Staphylococcus aureus

<400> SEQUENCE: 31

Met Glu Phe Val Ala Lys Leu Phe Lys Phe Phe Lys Asp Leu Leu Gly
1               5                   10                  15

Lys Phe Leu Ala Asn Asn
            20

<210> SEQ ID NO 32
<211> LENGTH: 22
<212> TYPE: PRT
<213> ORGANISM: Staphylococcus aureus

<400> SEQUENCE: 32

Met Glu Phe Val Ala Lys Leu Phe Lys Phe Phe Lys Asp Leu Leu Gly
1               5                   10                  15

Lys Phe Leu Gly Ala Asn
            20

<210> SEQ ID NO 33
<211> LENGTH: 22
<212> TYPE: PRT
<213> ORGANISM: Staphylococcus aureus

<400> SEQUENCE: 33

Met Glu Phe Val Ala Lys Leu Phe Lys Phe Phe Lys Asp Leu Leu Gly
1               5                   10                  15

Lys Phe Leu Gly Asn Ala
            20
```

US 8,211,445 B2

PSM PEPTIDES AS VACCINE TARGETS AGAINST METHICILLIN-RESISTANT *STAPHYLOCOCCUS*

CROSS REFERENCE TO RELATED APPLICATIONS

This is a continuation-in-part of International Patent Application PCT/US2008/063119, filed May 8, 2008, designating the United States and published in English as WO 2008/154101, which claims the benefit of U.S. Provisional Application No. 60/933,573, filed Jun. 6, 2007, and U.S. Provisional Application No. 60/983,141, filed Oct. 26, 2007. The entire contents of these prior applications are incorporated herein by reference.

FIELD OF THE DISCLOSURE

This disclosure concerns compositions and methods for the treatment and inhibition of infectious disease, particularly methicillin-resistant *Staphylococcus*. In certain embodiments, the disclosure concerns immunogenic peptides, for instance PSM peptides, which can be used to induce protective immunity against methicillin-resistant *Staphylococcus*.

BACKGROUND

Methicillin-resistant *Staphylococcus aureus* (MRSA) and methicillin-resistant *Staphylococcus epidermidis* (MRSE) are dangerous human pathogens. Traditionally, MRSA infections occurred exclusively in hospitals and were limited to immunocompromised patients or individuals with predisposing risk factors. However, MRSA strains have recently emerged that can cause severe infections (such as necrotizing fasciitis) or death in otherwise healthy adults. These strains are increasingly community-acquired, and can be contracted outside of the health care settings. As is true for hospital-acquired MRSA, the incidence of these community-associated (CA)-MRSA infections is increasing. For example, the majority of infections in patients reporting to emergency departments in the United States are now due to CA-MRSA. Individuals with indwelling medical devices are particularly at risk for infection with *S. epidermidis*, including MRSE.

It is unclear what makes CA-MRSA strains more successful at causing human disease compared with their hospital-associated counterparts. Given the foregoing, it would be desirable to know the cause of the increased virulence of CA-MRSA, and to have methods of treating, ameliorating, and preventing MRSA. Similarly, it would be desirable to identify virulence factors of methicillin-resistant *staphylococcus* and to have methods of treating, ameliorating, and preventing these infections.

SUMMARY OF THE DISCLOSURE

Described herein is a class of secreted staphylococcal peptides with an extraordinary ability to recruit, activate, and subsequently lyse human neutrophils, thus eliminating the main cellular defense against staphylococcal infection (for example, *S. aureus* or *S. epidermidis* infection). These peptides are produced at especially high levels in methicillin-resistant *staphylococcus* (for example, methicillin-resistant *S. aureus* (MRSA) or methicillin-resistant *S. epidermidis* (MRSE)), and to a large extent determine their aggressive behavior and ability to cause disease in animal models of infection. Thus, disclosed is a set of virulence factors of *staphylococcus* (for example, *S. aureus* and *S. epidermidis*) that account for virulence (such as the enhanced virulence of CA-MRSA).

The peptides are phenol-soluble modulins (PSM) and include PSMs encoded by the PSMα gene cluster (for example, PSMα1, PSMα2, PSMα3, and PSMα4) and a PSM (PSM-mec) encoded by a PSM gene in the methicillin resistance-encoding mobile genetic element (MGE) SCCmec. Most of these PSM peptides activate and subsequently lyse neutrophils. The identification of these peptides enables the production of vaccines and other preventative and/or therapeutic agents for use in subjects infected with methicillin-resistant staphylococci.

One disclosed embodiment is an isolated immunogenic peptide that includes at least one antigenic phenol-soluble modulin alpha (PSMα) or PSM-mec peptide. The peptide includes (a) the amino acid sequence set forth as SEQ ID NO: 8; (b) the amino acid sequence set forth as SEQ ID NO: 2; (c) the amino acid sequence set forth as SEQ ID NO: 3; (d) the amino acid sequence set forth as SEQ ID NO: 4; (e) the amino acid sequence set forth as SEQ ID NO: 1; (f) the amino acid sequence set forth as SEQ ID NO: 9; (g) an amino acid sequence having at least 85% sequence identity with (b), (e), or (f); or (h) an amino acid sequence having at least 90% sequence identity with (a), (c), or (d). In some embodiments, the amino acid sequence has at least 90% sequence identity with (b), (e), or (f). In other embodiments, the amino acid sequence has at least 95% sequence identity with (a), (b), (c), (d), (e), or (f).

Another embodiment is a method for eliciting an immune response in a subject. The method includes (a) selecting a subject in which an immune response to the immunogenic peptides disclosed herein is desirable; and (b) administering to the subject a therapeutically effective amount of the immunogenic peptide described above. In some embodiments, mixtures of PSM peptides (such as mixtures of PSMα peptides or PSMα and PSM-mec peptides) are administered to the subject, and in other embodiments, one or more PSMβ peptide is administered in combination with one or more PSMα or PSM-mec peptide. The method is particularly useful in stimulating an immune response against methicillin-resistant *staphylococcus*, such as methicillin-resistant *S. aureus* or methicillin-resistant *S. epidermidis*. Subjects at risk of developing such infections can therefore be selected and administered the immunogen to stimulate their immunity against such infection, thereby producing an immune response in the subject.

An additional embodiment is a method for diagnosing methicillin-resistant *staphylococcus* (for example, MRSA or MRSE) in a subject. The method includes selecting a subject at risk for developing methicillin-resistant *staphylococcus*, collecting a biological sample from the subject, and determining whether an anti-PSM antibody (such as an anti-PSM-mec antibody) is present in the sample. The presence of an anti-PSM-mec antibody in the sample indicates that the subject has methicillin-resistant *staphylococcus*.

The foregoing and other features will become more apparent from the following detailed description of several embodiments, which proceeds with reference to the accompanying figures.

BRIEF DESCRIPTION OF THE FIGURES

1B shows the location of PSM genes in the genome of *S. aureus* MW24.

FIG. 2 includes three panels showing murine models of *S. aureus* infection. In FIGS. 2A, 2C, *, P<0.05; , P<0.01; *, P<0.001, (*), significant difference in the opposite direction (for Δβ strain, P<0.05); all versus wild-type.

FIG. 3 includes three panels showing the interaction of PSMs with human neutrophils.

FIG. 4 includes several panels showing PSM-induced lysis of human neutrophils.

FIG. 5 is a series of graphs and digital images of gels showing detection of PSMs in *S. aureus* wild-type and PSM gene deletion strains.

FIG. 6 includes a series of graphs showing the interaction of PSMs with human neutrophils.

FIG. 8 includes several graphs showing hemolytic activities of PSMs. In FIGS. 8A and 8B, the data are mean±SEM of three independent measurements. P values are vs. DMSO in FIG. 8A and vs. wild-type in FIG. 8B. Hemolytic activity was determined by incubating samples with a 2% (v/v) suspension of sheep red blood cells and incubation at 37° C. for 1 hour. Synthetic PSM peptides or filtered bacterial overnight culture supernatants were diluted in PBS and added to sheep erythrocytes at a final concentration of 10 µg/ml for the peptides and 1:200 for culture filtrates.

FIG. 9 includes several panels showing flow cytometric analyses of neutrophil recruitment and destruction by *S. aureus* infection. CD1 Swiss female mice were i.p. injected with 100 µl of sterile PBS or $10^7$ live *S. aureus* strains. Cells were harvested two hours after inoculation by rinsing the mouse abdominal cavity with RPMI medium plus 10% FBS, and stained with FITC-conjugated rat anti-mouse Gr1 as neutrophil surface marker. Propidium iodide was used to identify dead cells. FIG. 9A shows a forward/side light scatter gate for WBCs (R1). FIG. 9B shows a dot plot illustrating WBCs stained with FITC-conjugated rat $IgG_{2a}$ isotype control. FIGS. 9C and 9D show dot plots illustrating neutrophil recruitment (FL1+) and destruction (FL1+/FL2+) by i.p. injection of sterile PBS (FIG. 9C) or $10^7$ live *S. aureus* MW2 wild-type strain (FIG. 9D). Representative FACS dot plots gated on Gr1+ neutrophils are shown from three to five independent samples per treatment and from two separate experiments.

FIG. 10 includes two panels showing growth- and agr-dependent production of PSMs.

FIG. 17 is a graph showing that anti PSM-α, -β, and δ-toxin specific antisera mediated opsonophagocytosis and killing of *S. aureus* (LAC) by human PMNs.

FIG. 18 includes two panels showing RP-HPLC and ESI analysis of PSM-mec production in *S. aureus* and *S. epidermidis*.

FIG. 19 includes two panels showing molar ellipticity and amphipathy of PSM-mec.

FIG. 20 includes three panels showing characteristics of PSM-mec production and regulation in *S. aureus*.

FIG. 21 is a series of graphs showing pro-inflammatory and cytolytic capacities of PSM-mec and derivatives.

FIG. 22 includes three panels showing the influence of PSM-mec on biofilm formation and intercellular aggregation.

FIG. 23 includes three panels showing cytolytic activities of *S. aureus* PSM-mec producers and isogenic psm-mec deletion mutants.

FIG. 24 is a series of graphs showing impact of PSM-mec on virulence in animal infection models.

SEQUENCE LISTING

Figure 1A:
FIG. 1A is an alignment of the PSM amino acid sequences. The PSMs are all formylated at the N-terminal methionine residue (designated by "f"). FIG.

The amino acid sequences listed in the accompanying sequence listing are shown using standard letter abbreviations for amino acids, as defined in 37 C.F.R. 1.822. In the accompanying sequence listing:

SEQ ID NO: 1 is the amino acid sequence of PSMα1.

MGIIAGIIKVIKSLIEQFTGK

SEQ ID NO: 2 is the amino acid sequence of PSMα2.

MGIIAGIIKFIKGLIEKFTGK

SEQ ID NO: 3 is the amino acid sequence of PSMα3.

MEFVAKLFKFFKDLLGKFLGNN

SEQ ID NO: 4 is the amino acid sequence of PSMα4.

MAIVGTIIKIIKAIIDIFAK

SEQ ID NO: 5 is the amino acid sequence of δ-Toxin.

MAQDIISTISDLVKWIIDTVNKFTKK

SEQ ID NO: 6 is the amino acid sequence of PSMβ1.

MEGLFNAIKDTVTAAINNDGAKLGTSIVSIVENGVGLLGKLFGF

SEQ ID NO: 7 is the amino acid sequence of PSMβ2.

MTGLAEAIANTVQAAQQHDSVKLGTSIVDIVANGVGLLGKLFGF

SEQ ID NO: 8 is a PSMα consensus sequence.

MGIIAGIIK(V/F)IK(S/G)LIE(Q/K)FTGK

SEQ ID NO: 9 is the amino acid sequence of PSM-mec.

MDFTGVITSIIDLIKTCIQAFG

SEQ ID NOs: 10-13 are the nucleic acid sequences of primers for constructing the PSM-mec deletion mutant.

SEQ ID NOs: 14-33 are the amino acid sequences of PSMα3 mutant peptides.

DETAILED DESCRIPTION

I. Overview of Several Embodiments

The compositions and methods described herein take advantage of the surprising discovery of a class of secreted staphylococcal peptides that has an extraordinary ability to recruit, activate, and subsequently lyse human neutrophils, thus eliminating the main cellular defense against *staphylococcus* infection. In some examples, these peptides are produced at especially high levels in CA-MRSA and to a large extent determine their aggressive behavior and ability to cause disease in animal models of infection. In other examples, these peptides are produced in staphylococcal strains including SCCmec clusters of types II, III, or VIII, including *S. aureus, S. epidermidis, S. saprophyticus, S. pseudintermedius*, and *S. sciuri*.

In some examples, the peptides are encoded by the phenol-soluble modulin (PSM) gene cluster and include PSMα1, PSMα2, PSMα3, and PSMα4, most of which activate and subsequently lyse neutrophils. In other examples, the peptides are encoded by a PSM gene included on a staphylococcal methicillin resistance-encoding mobile genetic element SCCmec and includes PSM-mec. The identification of these peptides makes possible the production of vaccines and other preventative and/or therapeutic agents for use in subjects infected with methicillin-resistant *staphylococcus* including, but not limited to, MRSA and MRSE.

Thus, disclosed herein is an isolated immunogenic peptide that includes at least one antigenic phenol-soluble modulin alpha (PSMα) or PSM-mec peptide. This peptide includes: (a) the amino acid sequence set forth as SEQ ID NO: 8; (b) the amino acid sequence set forth as SEQ ID NO: 2; (c) the amino acid sequence set forth as SEQ ID NO: 3; (d) the amino acid sequence set forth as SEQ ID NO: 4; (e) the amino acid sequence set forth as SEQ ID NO: 1; (f) the amino acid sequence set forth as SEQ ID NO: 9; (g) an amino acid sequence having at least 85% sequence identity with (b), (e), or (f); or (h) an amino acid sequence having at least 90% sequence identity with (a), (c), or (d). In some embodiments, the PSM peptide includes an amino acid sequence having at least 95% sequence identity with (a), (b), (c), (d), (e), or (f), and in particular embodiments the PSMα or PSM-mec peptide is (a) the amino acid sequence set forth as SEQ ID NO: 8;

(b) the amino acid sequence set forth as SEQ ID NO: 2; (c) the amino acid sequence set forth as SEQ ID NO: 3; (d) the amino acid sequence set forth as SEQ ID NO: 4; (e) the amino acid sequence set forth as SEQ ID NO: 1; (f) the amino acid sequence set forth as SEQ ID NO: 9; (g) an amino acid sequence having at least 85% sequence identity with (b), (e), or (f); or at least 90% sequence identity with (a), (c), or (d). The peptide can be immunogenic fragments or immunogenic fusion proteins that include heterologous proteins other than the PSMα or PSM-mec peptides or variants thereof and retain the immunogenicity of the peptides recited in SEQ ID NOs: 1, 2, 3, 4, 8, or 9. Another embodiment includes an isolated polynucleotide that includes a nucleic acid sequence encoding the immunogenic PSMα or PSM-mec peptide, or its immunogenic fragments or fusion proteins. In certain examples, the polynucleotide is operably linked to a promoter. Yet another embodiment is a vector that includes this polynucleotide. In some embodiments, the isolated immunogenic PSMα or PSM-mec peptide provides protective immunity from methicillin-resistant staphylococcus (for example, MRSA or MRSE) when administered to a subject in a therapeutically effective amount. In particular examples, the MRSA is community-associated MRSA (CA-MRSA).

Another embodiment is a pharmaceutical composition that includes the immunogenic PSMα or PSM-mec peptide together with a pharmaceutically acceptable carrier, and, in some examples, a therapeutically effective amount of an adjuvant, such as IL-2, RANTES, GM-CSF, G-CSF, TNF-α, IFN-γ, IL-12, or IL-6. Certain examples of the pharmaceutical composition include mixtures of two or more PSMα peptides, one or more PSMα peptide and a PSM-mec peptide, or, optionally, a combination of one or more PSMα peptides or PSM-mec peptides and one or more PSMβ peptides.

Other embodiments are methods for eliciting an immune response in a subject. These methods include (a) selecting a subject in which an immune response to the immunogenic PSMα or PSM-mec peptide is desirable; and (b) administering to the subject a therapeutically effective amount of the immunogenic PSMα peptide or PSM-mec peptide, a combination of PSMα peptides, or a combination of PSMα and PSM-mec peptides, thereby producing an immune response in the subject. Certain examples of the method also include administering one or more PSMβ peptide to the subject. In some examples, administration includes oral, topical, mucosal, or parenteral administration, and in certain examples, parenteral administration includes intravenous administration, intramuscular administration, or subcutaneous administration. The immunogenic PSMα or PSM-mec peptide is administered, in some examples, in from about one to about six doses, for instance two doses. In certain examples, the method further includes administering a therapeutically effective amount of an adjuvant to the subject, for instance a therapeutically effective amount of IL-2, RANTES, GM-CSF, G-CSF, TNF-α, IFN-γ, IL-12, or IL-6, or a combination thereof.

Still other embodiments are methods for inhibiting methicillin-resistant staphylococcus infection (for example, MRSA or MRSE infection) in a subject. These methods include (a) selecting a subject at risk for exposure to methicillin-resistant staphylococcus; and (b) administering to the subject a therapeutically effective amount of the immunogenic PSMα or PSM-mec peptide or a combination of PSMα or PSM-mec peptides, thereby inhibiting methicillin-resistant staphylococcus infection in the subject. Some examples of the method further include administering one or more PSMβ peptides to the subject. In particular examples, the methicillin-resistant staphylococcus is MRSA or MRSE. In particular examples, the MRSA is community-associated MRSA (CA-MRSA).

Other embodiments include methods for diagnosing methicillin-resistant staphylococcus in a subject. These methods include (a) selecting a subject at risk for developing methicillin-resistant staphylococcus; (b) collecting a biological sample from the subject; and (c) determining whether an anti-PSM-mec antibody is present in the sample, wherein the presence of an anti-PSM-mec antibody in the sample indicates that the subject has methicillin-resistant staphylococcus. In some examples, the methicillin-resistant staphylococcus is MRSA (for example, community-associated MRSA (CA-MRSA) or hospital-acquired MRSA (HA-MRSA)), and in other examples, the methicillin-resistant staphylococcus is MRSE.

II. Abbreviations

CA: community-associated
CD: circular dichroism
EIC: extracted ion chromatograms
FITC: fluorescein isothiocyanate
Fmlp; formyl-met-leu-phe
HA: hospital-associated
HSA: human serum albumin
HBSS: Hank's Buffered Salt Solution
LDH: lactate dehydrogenase
MRSA: methicillin-resistant *Staphylococcus aureus*
MRSE: methicillin-resistant *Staphylococcus epidermidis*
MSSA: methicillin-sensitive *Staphylococcus aureus*
MSSE: methicillin-sensitive *Staphylococcus epidermidis*
PSM: phenol-soluble modulin
PVL: Panton-Valentine leukocidin
RP-HPLC/ESI-MS: reversed phase high pressure liquid chromatography/electrospray ionization mass spectrometry
RPMI: Roswell Park Memorial Institute medium
SDS-PAGE: sodium dodecyl sulfate polyacrylamide gel electrophoresis
TSB: tryptic soy broth

III. Terms

In order to facilitate review of the various embodiments of the disclosure, the following explanations of specific terms are provided:

Adjuvant: An agent used to enhance antigenicity. Some adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunstimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants also can include biological molecules, such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL. Adjuvants also can include dsRNA.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

Antibody: Immunoglobulin molecules and immunologically active portions of immunoglobulin molecules, for instance, molecules that contain an antigen binding site that specifically binds (immunoreacts with) an antigen.

A naturally occurring antibody (for example, IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., *Nature* 341:544-546, 1989) which consists of a $V_H$ domain; (v) an isolated complimentarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (for instance, see U.S. Pat. No. 4,745,055; U.S. Pat. No. 4,444, 487; WO 88/03565; EP 256,654; EP 120,694; EP 125,023; Faoulkner et al., (1982) *Nature* 298:286; Morrison, (1979) *J. Immunol.* 123:793; Morrison et al., (1984) *Ann Rev. Immunol* 2:239).

Animal: Living multi-cellular vertebrate organisms, a category that includes, for example, mammals and birds. The term mammal includes both human and non-human mammals. Similarly, the term "subject" includes both human and veterinary subjects.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: As used herein, the term "conservative variant," in the context of an immunogenic PSM peptide, refers to a peptide or amino acid sequence that deviates from another amino acid sequence only in the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some embodiments, conservative amino acid substitutions are those substitutions that do not substantially affect or decrease antigenicity of an immunogenic PSM peptide. Specific, non-limiting examples of conservative substitutions are shown in Table 1, below.

The term conservative variation also includes the use of a substituted amino acid in place of an unsubstituted parent amino acid, provided that antibodies raised to the substituted peptide also immunoreact with the unsubstituted peptide. Non-conservative substitutions are those that reduce antigenicity.

Epitope: An antigenic determinant. These are particular chemical groups or peptide sequences on a molecule that are antigenic (that elicit a specific immune response). An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, for instance, "Epitope Mapping Protocols" in *Methods in Molecular Biology*, Vol. 66, Glenn E. Morris, Ed (1996).

Encode: As used herein, the term "encode" refers to any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some examples, an RNA molecule can encode a DNA molecule, for instance, by the process of reverse transcription incorporating an RNA-dependent DNA polymerase. In another example, a DNA molecule can encode a peptide, where it is understood that "encode" as used in that case incorporates both the processes of transcription and translation.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (for instance, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements that are sufficient to render promoter-dependent gene expression controllable for cell-type specific, tissue-specific, or inducible by external signals or agents; such elements may be located in the 5' or 3' regions of the gene. Both constitutive and inducible promoters are included (see for instance, Bitter et al., (1987) *Methods in Enzymology* 153:516-544). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a cell, tissue or subject to an agent that increases or decreases gene expression. Expression of a gene also can be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression can be measured at the RNA level or the protein level and by any method known in the art, including, without limitation, Northern blot, RT-PCR, Western blot, or in vitro, in situ, or in vivo protein activity assay(s).

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a PSMα peptide-encoding RNA, or a PSMα peptide-encoding DNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic protein or peptide: A protein or peptide that includes an allele-specific motif or other sequence such that the peptide will bind an MHC molecule and induce a cytotoxic T lymphocyte ("CTL") response, or a B cell response (for instance, antibody production) against the antigen from which the immunogenic peptide is derived.

In one embodiment, immunogenic proteins and peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing protein. Within the context of an immunogenic protein or peptide, a "conserved residue" is one which appears in a significantly higher frequency than would be expected by random distribution at a particular position in a peptide. In one embodiment, a conserved residue is one where the MHC structure may provide a contact point with the immunogenic protein or peptide.

Immunogenic proteins and peptides also can be identified by measuring their binding to a specific MHC protein and by their ability to stimulate CD4 and/or CD8 when presented in the context of the MHC protein.

Generally, immunogenic PSM peptides can be used to induce an immune response in a subject, such as a B cell response or a T cell response.

Immunogenic composition: A composition comprising an immunogenic PSM peptide that induces a measurable B cell response (such as production of antibodies that specifically bind the PSMα, PSM-mec, PSMβ, or δ-toxin antigens) against methicillin-resistant *staphylococcus*. For in vitro use, the immunogenic composition can consist of the immunogenic peptide alone. For in vivo use, the immunogenic composition will typically comprise the immunogenic peptide in a pharmaceutically acceptable carrier, and/or other agents. An immunogenic composition optionally can include an adjuvant, a costimulatory molecule, or a nucleic acid encoding a costimulatory molecule.

Isolated: An "isolated" biological component (such as a nucleic acid or protein or organelle) has been substantially separated or purified away from other biological components in the cell of the organism in which the component naturally occurs, for instance, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mammal: This term includes both human and non-human mammals. Similarly, the term "subject" includes both human and veterinary subjects.

Methicillin-resistant *staphylococcus*: Bacteria of the genus *Staphylococcus* which are resistant to penicillin and β-lactam penicillin-derivatives, such as methicillin, ampicillin, oxacillin, and nafcillin Methicillin-resistant *staphylococcus* includes methicillin-resistant forms of *S. aureus*, *S. epidermidis*, *S. saprophyticus*, *S. pseudintermedius*, and *S. sciuri*. Of these, methicillin-resistant *S. aureus* (MRSA) and *S. epidermidis* (MRSE) are the most significant in terms of human disease. Staphylococcal bacteria that are non-resistant to methicillin are sometimes referred to as "methicillin-sensitive" or "methicillin-susceptible" *staphylococcus*.

MRSA: Methicillin-resistant *Staphylococcus aureus* includes isolates of the bacterium *Staphylococcus aureus* that are characterized by antibiotic resistance to all penicillins, including methicillin and other narrow-spectrum β-lactamase-resistant penicillin antibiotics. MRSA was discovered for the first time in 1961 in the UK, but it is now widespread in hospital settings. MRSA is commonly termed a "superbug." MRSA may also be known as oxacillin-resistant *Staphylococcus aureus* (ORSA) and multiple-resistant *Staphylococcus aureus*. Strains of *S. aureus* that are non-resistant to methicillin are sometimes called methicillin-susceptible or methicillin-sensitive *Staphylococcus aureus* (MSSA) if an explicit distinction must be made.

Although MRSA has traditionally been seen as a hospital-associated infection, community-acquired MRSA strains have appeared in recent years, notably in the U.S. and Australia. The abbreviations CA-MRSA (community-acquired MRSA) and HA-MRSA (hospital-acquired MRSA) distinguish the two forms of the disease.

Approximately 10% of *S. aureus* isolates in the United States are susceptible to penicillin. However, many *S. aureus* strains, while resistant to penicillin, remain susceptible to penicillinase-stable penicillins, such as oxacillin and methicillin (methicillin-sensitive *S. aureus* (MSSA)). Strains that are oxacillin and methicillin resistant, historically termed methicillin-resistant *S. aureus* (MRSA), are resistant to all β-lactam agents, including cephalosporins and carbapenems. Hospital-associated MRSA isolates often are multiply resistant to other commonly used antimicrobial agents, including erythromycin, clindamycin, and tetracycline, while community-associated MRSA isolates are often resistant only to β-lactam agents and erythromycin. Since 1996, MRSA strains with decreased susceptibility to vancomycin (minimum inhibitory concentration [MIC], 8-16 µg/ml) and strains fully resistant to vancomycin (MIC≧32 µg/ml) have been reported.

MRSA have many virulence factors that enable them to cause disease in normal hosts. For example, MRSA are frequent causes of healthcare-associated bloodstream and catheter-related infections. MRSA are also an emerging cause of community-associated infections, especially skin and soft tissue infections and necrotizing pneumonia. Vancomycin and two newer antimicrobial agents, linezolid and daptomycin, are among the drugs that are used for treatment of severe healthcare-associated MRSA infections. Although some strains remain susceptible to trimethoprim/sulfamethoxazole, gentamicin, or rifampin, these drugs are not typically used as first-line agents. Because of the rapid emergence of resistance to rifampin, this drug is unsuitable for use as a single agent to treat MRSA infections.

An MRSA outbreak can occur when one strain is transmitted to other patients or close contacts of the infected persons in the community. Often this occurs when a patient or healthcare worker is colonized with an MRSA strain (for instance, carries the organism but shows no clinical signs or symptoms of infection) and, through contact, spreads the strain to another person. Handwashing and screening patients for MRSA should be performed to decrease transmission and reduce the number of patients infected with MRSA.

Several methods are used to identify MRSA. The National Committee for Clinical Laboratory Standards, now called the Clinical and Laboratory Standards Institute (CLSI), recommends the cefoxitin disk screen test, the latex agglutination test for PBP2a, or a plate containing 6 µg/ml of oxacillin in Mueller-Hinton agar supplemented with NaCl (4% w/v; 0.68 mol/L) as suitable methods of testing for MRSA. For methods of inoculation, see the CLSI Approved Standard M100-S15 (CLSI. 2007. "Performance standards for antimicrobial susceptibility testing." *CLSI approved standard M*100-S17. Clinical and Laboratory Standards Institute, Wayne, Pa.).

Accurate detection of oxacillin/methicillin resistance can be difficult due to the presence of two subpopulations (one susceptible and the other resistant) that may coexist within a culture of staphylococci (Bannerman, 2003. "*Staphylococcus, Micrococcus* and other catalase-positive cocci that grow aerobically." In P. R. Murray, E. J. Baron, J. H. Jorgensen, M. A. Pfaller, R. H. Yolken [eds.], *Manual of Clinical Microbiology* 8th ed. ASM Press, Washington, D.C.). All cells in a culture may carry the genetic information for resistance, but only a small number may express the resistance in vitro. This phenomenon is termed heteroresistance and occurs in staphylococci resistant to penicillinase-stable penicillins, such as oxacillin. Cells expressing heteroresistance grow more slowly than the oxacillin-susceptible population and may be missed at temperatures above 35° C. This is why CLSI recommends incubating isolates being tested against oxacillin, methicillin, or nafcillin at 33-35° C. (maximum of 35° C.) for a full 24 hours before reading.

When used correctly, broth-based and agar-based tests usually can detect MRSA. The cefoxitin disk diffusion method can be used in addition to routine susceptibility test methods or as a back-up method. In addition, nucleic acid amplification tests, such as the polymerase chain reaction (PCR), can be used to detect the mecA gene, which mediates oxacillin resistance in staphylococci. Staphylococcal resistance to oxacillin/methicillin occurs when an isolate carries an altered penicillin-binding protein, PBP2a, which is encoded by the mecA gene. The new penicillin-binding protein binds beta-lactams with lower avidity, which results in resistance to this class of antimicrobial agents.

The CLSI breakpoints for *S. aureus* are different than those for coagulase-negative staphylococci (CoNS):

Interpretive Criteria (in μg/ml) for Oxacillin MIC Tests

|  | Susceptible | Intermediate | Resistant |
| --- | --- | --- | --- |
| *S. aureus* | ≦2 μg/ml | N/A | ≧4 μg/ml |
| CoNS | ≦0.25 μg/ml | N/A | ≧0.5 μg/ml |

Interpretive Criteria (in mm) for Oxacillin Disk Diffusion Tests

|  | Susceptible | Intermediate | Resistant |
| --- | --- | --- | --- |
| *S. aureus* | ≧13 mm | 11-12 mm | ≦10 mm |
| CoNS | ≧18 mm | N/A | ≦17 mm |

N/A = not applicable

Interpretive Criteria (in mm) for Cefoxitin Disk Diffusion Test

|  | Susceptible*† | Resistant** |
| --- | --- | --- |
| *S. aureus* | ≧22 mm | ≦21 mm |
| CoNS | ≧25 mm | ≦24 mm |

*Report as oxacillin susceptible
**Report as oxacillin resistant
†There is no intermediate category with the cefoxitin disk diffusion test There are several reasons why oxacillin and cefoxitin are used for testing instead of methicillin First, methicillin is no longer commercially available in the United States. Second, oxacillin maintains its activity during storage better than methicillin and is more likely to detect heteroresistant strains. However, cefoxitin is an even better inducer of the mecA gene and disk diffusion tests using cefoxitin give clearer endpoints and are easier to read than tests with oxacillin.

MRSE: Methicillin-resistant *Staphylococcus epidermidis* (MRSE) includes isolates of the bacterium *S. epidermidis* that are characterized by antibiotic resistance to all penicillins, including methicillin and other narrow-spectrum β-lactamase-resistant penicillin antibiotics. *S. epidermidis* is a coagulase-negative *staphylococcus* species. Methods for identifying MRSE strains are as described above for MRSA, using the CLSI breakpoints for coagulase-negative staphylococci (CoNS) provided above.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically or can contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence. When recombinantly produced, operably linked nucleic acid sequences are generally contiguous and, where necessary to join two protein-coding regions, in the same reading frame. However, nucleic acids need not be contiguous to be operably linked.

Parenteral administration: Administration by injection or infusion. Specific, non-limiting examples of parenteral routes of administration include: intravenous, intramuscular, intrathecal, intraventricular, intraarterial, intracardiac, subcutaneous, intradermal, intraperitoneal, epidural, intravitreal, and intraosseous infusion.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition (1995), describes compositions and formulations suitable for pharmaceutical delivery of the PSM peptides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount necessary to induce an immune response in a subject. When administered to a subject, a dosage will generally be used that will achieve target tissue concentrations (for example, in lymphocytes) that has been shown to achieve an in vitro effect.

Peptide: Any chain of amino acids, regardless of length or post-translational modification (for instance, glycosylation or phosphorylation). In one embodiment, the protein is a PSM peptide (for example, a PSMα or PSM-mec peptide). Longer peptides are often referred to as proteins. With regard to proteins or peptides, "comprises" indicates that additional amino acid sequence or other molecules can be included in the molecule, "consists essentially of" indicates that additional amino acid sequences are not included in the molecule, but that other agents (such as labels or chemical compounds) can be included, and "consists of" indicates that additional amino acid sequences and additional agents are not included in the molecule.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (for instance, a cDNA) independent of other sequences. The nucleotides can be ribonucleotides, deoxyribonucleotides, or modified forms of either nucleotide. The term includes single- and double-stranded forms of DNA.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

PSMα peptide: Any of several peptides encoded by the phenol-soluble modulin (PSM) α gene cluster. The peptides disclosed herein were identified in *S. aureus*, and include PSMα1 (SEQ ID NO: 1), PSMα2 (SEQ ID NO: 2), PSMα3 (SEQ ID NO: 3), and PSMα4 (SEQ ID NO: 4), most of which activate and subsequently lyse neutrophils. In some embodiments, the PSMα peptides are formylated, for example, N-terminal formylation, whereas in other embodiments they are not formylated. In other embodiments, the PSMα peptides include variants that contain a substitution of one or several amino acids for amino acids having similar biochemical properties (so-called conservative substitutions). The peptide may also be an immunogenic fragment or a fusion with a heterologous peptide sequence. Conservative amino acid substitutions are likely to have minimal impact on the activity of the resultant protein. Further information about conservative substitutions can be found, for instance, in section IVB of the Detailed Description, below.

Without being bound by theory, the membrane-damaging activity of PSMαs most likely is due to their strong α-helicity and amphipathy, which are typical features of pore-forming peptides.

PSMβ peptide: Any of several peptides encoded by the phenol-soluble modulin (PSM) β gene cluster. The peptides disclosed herein were identified in *S. aureus*, and include PSMβ1 (SEQ ID NO: 6) and PSMβ2 (SEQ ID NO: 7). In some embodiments, the PSMβ peptides are formylated, for example, N-terminal formylation, whereas in other embodiments they are not formylated. In other embodiments, the PSMβ peptides include variants that contain a substitution of one or several amino acids for amino acids having similar biochemical properties (so-called conservative substitutions). The peptide may also be an immunogenic fragment or a fusion with a heterologous peptide sequence. Conservative amino acid substitutions are likely to have minimal impact on the activity of the resultant protein. Further information about conservative substitutions can be found, for instance, in section IVB of the Detailed Description, below.

PSM-mec peptide: A peptide encoded by the phenol-soluble modulin (PSM)-mec gene present within some SCCmec clusters of methicillin-resistant *Staphylococcus* bacteria (for example, type II or type III SCCmec clusters). The PSM-mec peptide disclosed herein was identified in *S. aureus* and *S. epidermidis* and includes the amino acid sequence set forth as SEQ ID NO: 9. In some embodiments, the PSM-mec peptide is formylated, for example, N-terminal formylation, whereas in other embodiments it is not formylated. In other embodiments, the PSM-mec peptide includes variants that contain a substitution of one or several amino acids for amino acids having similar biochemical properties (so-called conservative substitutions). The peptide may also be an immunogenic fragment or a fusion with a heterologous peptide sequence. Conservative amino acid substitutions are likely to have minimal impact on the activity of the resultant protein. Further information about conservative substitutions can be found, for instance, in section IVB of the Detailed Description, below.

Purified: The PSM peptides disclosed herein can be purified (and/or synthesized) by any of the means known in the art (see, for instance, *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Risk of exposure to methicillin-resistant *staphylococcus*: A subject is at "risk of exposure to methicillin-resistant *staphylococcus*" (such as MRSA or MRSE) if there is an increased probability that the subject will be exposed to the bacterium relative to the general population. Accordingly, risk is a statistical concept based on empirical and/or actuarial data. Commonly, risk is correlated with one or more indicators, such as occupation, geographical location, living conditions, contact with potential methicillin-resistant *staphylococcus* carriers, or other occurrences, events or undertakings, of a subject. For example, indicators include but are not limited to close living or working conditions, and any condition or occupation that brings the subject in close contact with the public. In some examples, a subject is at risk of exposure to MRSE if the subject has a catheter or surgical implant, including but not limited to, a prosthetic valve, shunt, or joint prosthesis.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below, in section IV B of the Detailed Description.

Subcutaneous administration: delivery, most often by injection, of an agent into the subcutis. The subcutis is the layer of tissue directly underlying the cutis, composed mainly of adipose tissue. Subcutaneous injections are given by injecting a fluid into the subcutis. Within the context of administering immunogenic PSM peptides, subcutaneous administration most often will involve injection of a PSM peptide with an acceptable carrier into the subcutis of a subject at risk of exposure to methicillin-resistant *staphylococcus*.

Therapeutically active peptide: An agent, such as a PSMα, PSM-mec, or PSMβ peptide that causes induction of an immune response, as measured by clinical response (for example increase in a population of immune cells, increased cytolytic activity against cells that express a PSMα or PSM-mec peptide, or protection from methicillin-resistant staphylococcal infection). In one embodiment, a therapeutically effective amount of PSMα peptide is an amount used to generate an immune response against MRSA. In another embodiment, a therapeutically effective amount of PSM-mec peptide is an amount used to generate an immune response against MRSA or MRSE. The immune response may be generated in a person at risk for, or thought to already be infected with MRSA or MRSE.

Vector: A nucleic acid molecule capable of transporting a non-vector nucleic acid sequence which has been introduced into the vector. One type of vector is a "plasmid," which refers to a circular double-stranded DNA into which non-plasmid DNA segments can be ligated. Other vectors include cosmids, bacterial artificial chromosomes (BAC) and yeast artificial chromosomes (YAC). Another type of vector is a viral vector, wherein additional DNA segments can be ligated into all or part of the viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

The singular terms "a," "an," and "the" include plural referents unless context clearly indicates otherwise. "Comprising" means "including." "Comprising A or B" means "including A," "including B" or "including A and B." It is further to be understood that all base sizes or amino acid sizes, and all molecular weight or molecular mass values, given for nucleic acids or peptides are approximate, and are provided for description.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

IV. PSM Peptides as Vaccine Targets Against Methicillin-Resistant *Staphylococcus aureus*

A. Overview

Methicillin-resistant *Staphylococcus aureus* (MRSA) is bacterial infection that is resistant to certain antibiotics, such as methicillin, as well as other more common antibiotics such as oxacillin, penicillin and amoxicillin. *S. aureus* infections, including MRSA, occur most frequently among persons in hospitals and healthcare facilities (such as nursing homes and dialysis centers) who have weakened immune systems. Similarly, methicillin-resistant *Staphylococcus epidermidis* (MRSE) is a bacterial infection that is resistant to antibiotics, such as methicillin, penicillin, amoxicillin, and oxacillin *S. epidermidis* infection is usually non-pathogenic, however, individuals with compromised immune system are at risk for developing infection. Also, *S. epidermidis* infection is a major concern for individuals with catheters or other implants (such as prosthetic valves, shunts, or joint prostheses), particularly because of its ability to form biofilms.

MRSA infections that are acquired by persons who have not been recently (within the past year) hospitalized or had a medical procedure (such as dialysis, surgery, catheters) are known as CA-MRSA infections. MRSA infections in the community are usually manifested as skin infections, such as pimples and boils, or more serious conditions, such as necrotizing fasciitis or death, and occur in otherwise healthy people. Prior to this disclosure, it has been unclear what makes CA-MRSA strains more successful at causing human disease compared with their hospital-associated counterparts.

Disclosed herein is a class of secreted staphylococcal peptides (PSMα peptides) with an extraordinary ability to recruit, activate, and subsequently lyse human neutrophils, thus eliminating the main cellular defense against *S. aureus* infection. These peptides are produced at high levels in standard CA-MRSA strains and contribute significantly to their ability to cause disease in animal models of infection. This novel set of *S. aureus* virulence factors accounts at least in part for the enhanced virulence of CA-MRSA.

Also disclosed herein is a novel staphylococcal peptide (PSM-mec peptide) that is encoded within a mobile genetic element that also encodes methicillin resistance in staphylococcal bacteria (such as *S. aureus* and *S. epidermidis*). This peptide has pro-inflammatory and cytolytic activity and provides a connection between virulence and antibiotic resistance in staphylococci.

The present disclosure provides a treatment for persons at risk of a methicillin-resistant staphylococcal infection (such as MRSA or MRSE) infection or who are thought to be infected with MRSA or MRSE. Persons at risk of such an infection include persons living in institutions (such as nursing homes) or other crowded facilities, persons with a relative lack of immunity (such as the immunocompressed or elderly), persons with a catheter or other implant, and persons who come in contact with others who may have MRSA or MRSE (such as athletes or personnel at medical facilities).

B. PSM Peptides

Disclosed herein are several peptides encoded by the phenol-soluble modulin (PSM) gene cluster that have a significant effect on the ability of MRSA strains to cause disease. The peptides include PSMα1 (SEQ ID NO: 1), PSMα2 (SEQ ID NO: 2), PSMα3 (SEQ ID NO: 3), and PSMα4 (SEQ ID NO: 4), most of which activate and subsequently lyse neutrophils. Also provided is a PSMα consensus sequence (SEQ ID NO: 8), and two PSMβ peptides (SEQ ID NOs: 6 and 7). PSMα1 and PSMα2 (SEQ ID NOs: 1 and 2) share about 85% sequence identity. Also disclosed is a peptide (PSM-mec peptide; SEQ ID NO: 9) that is part of the PSM family based on its physico-chemical properties. The PSM-mec peptide is encoded by the psm-mec gene present on a SCCmec mobile genetic element of staphylococcus.

The identification of these peptides enables the production of vaccines and other preventative and/or therapeutic agents for use in subjects infected with methicillin-resistant staphylococcus (for example, MRSA or MRSE). The PSMα peptides described herein were identified in S. aureus. The PSMα peptides are of use in vaccines or other preventative and/or therapeutic agents for use in subjects infected with MRSA (for example, CA-MRSA). The PSM-mec peptides described herein were identified in S. aureus and S. epidermidis having a type II, type III, or type VIII SCCmec elements encoding methicillin-resistance. The PSM-mec peptides are of use in vaccines or other preventative and/or therapeutic agents for use in subjects infected with methicillin-resistant staphylococcus, such as MRSA or MRSA.

As described herein, S. aureus was found to secrete 4 shorter (~20 amino acids, α-type) and 2 longer (~40 amino acids, β-type) PSM-like peptides, whose genes are arranged in two gene clusters. In addition, S. aureus produces δ-toxin, which is similar to the α-type PSMs. Although the specific PSMα peptides disclosed herein range from 20 amino acids to 22 amino acids in length, other PSMα peptides and PSMα variants can be longer or shorter. In some examples, the PSMα peptides and PSMα variants may be about 15-30 amino acids long (for example, about 15-25 amino acids, about 18-25 amino acids, about 19-24 amino acids, or about 20-22 amino acids long). For instance, N-terminal or C-terminal additions of short amino acid sequences (for instance 1, 2, 3, or more amino acids) also yield active PSMα peptides, in certain embodiments. In some embodiments, the PSMα peptides disclosed herein are formylated, for example, N-terminal formylation, whereas in other embodiments they are not formylated. In other examples, the PSMα peptides disclosed herein include the N-terminal methionine residue, while in other examples, the N-terminal methionine is absent.

As also described herein, S. aureus and S. epidermidis strains were found to secrete a 22 amino acid peptide encoded on a SCCmec mobile genetic element that also encodes methicillin resistance in staphylococcal bacteria. Although the specific PSM-mec peptide is 22 amino acids in length, other PSM-mec peptides and variants can be longer or shorter. In some examples, the PSM-mec peptide and PSM-mec variants may be about 15-30 amino acids long (for example, about 15-25 amino acids, about 18-25 amino acids, about 19-24 amino acids, or about 20-22 amino acids long).

For instance, N-terminal or C-terminal additions of short amino acid sequences (for instance 1, 2, 3, or more amino acids) also yield active PSM-mec peptides, in certain embodiments. In some embodiments, the PSM-mec peptides are formylated, for example, N-terminal formylation, whereas in other embodiments they are not formylated. In other examples, the PSM-mec peptides disclosed herein include the N-terminal methionine residue, while in other examples, the N-terminal methionine is absent.

In some embodiments, the PSMα and PSM-mec peptides have non-conservative substitutions (such as 1, 2, 3, or 4 substitutions). For instance, PSMα1 and PSMα2 differ at positions 10, 13, and 17. Thus, PSMα1 (SEQ ID NO: 1) could, in a specific, non-limiting example, have a phenylalanine in place of the valine at position 10, and/or a glycine in place of the serine at position 13, and/or a lysine in place of the glutamine at position 17. Conversely, PSMα2 (SEQ ID NO: 2) could have a valine in place of the phenylalanine at position 10, and/or a serine in place of the glycine at position 13, and/or a glutamine in place of the lysine at position 17. Similar substitutions can be made in the sequences of PSMα3 and PSMα4 (SEQ ID NOs: 3 and 4) at these and other positions where the PSMα sequences differ from one another. In additional, non-limiting, examples, the PSMα and PSM-mec peptides could have one or more amino acids replaced with an alanine (for example, SEQ ID NOs: 14-33).

In some examples, a PSMα or PSM-mec peptide with a non-conservative substitution has reduced activity compared to the wild type peptide (such as reduced pro-inflammatory activity, for example one or more of reduced neutrophil lysis, reduced CD11b expression, or reduced IL-8 secretion activity), while retaining immunogenic properties. In particular examples, the PSMα and/or PSM-mec peptide variants have a decrease in activity of at least 10% (such as at least 20%, 30%, 40%, 50%, 60%, 70%, 80%, 90%, 95%, or even 99%) as compared to the corresponding wild type PSM peptide.

The PSM peptides disclosed herein also include variants that contain a substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (J. Bacteriol., 169:751-757, 1987), O'Regan et al. (Gene, 77:237-251, 1989), Sahin-Toth et al. (Protein Sci., 3:240-247, 1994), Hochuli et al. (Bio/Technology, 6:1321-1325, 1988) and in widely used textbooks of genetics and molecular biology. In some examples, PSM peptide variants can have no more than 1, 2, 3, or 4 conservative amino acid changes. Table 1 shows exemplary conservative amino acid substitutions that can be made to PSM peptides. In some embodiments, a conservative substitution of a cysteine residue can also include Met, Gly, Glu, Asp, Val, Thr, Tyr, or Ala.

TABLE 1

Exemplary conservative amino acid substitutions

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |

TABLE 1-continued

Exemplary conservative amino acid substitutions

| Original Residue | Conservative Substitutions |
| --- | --- |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In addition, the peptides disclosed herein can include a label or detectable compound or composition facilitating detection of the peptide. Specific, non-limiting examples of labels include fluorescent tags, enzymatic linkages, and radioactive isotopes. For example, the label is, in certain embodiments, a detectable marker, such as a radiolabeled amino acid or a peptide of biotinyl moieties that can be detected by marked avidin (for example, streptavidin containing a fluorescent marker or enzymatic activity that can be detected by optical or colorimetric methods). Various methods of labeling peptides and glycoproteins are known in the art and can be used. Examples of labels for peptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined peptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

C. Nucleic Acid Sequences and Variants

As any molecular biology textbook teaches, a peptide of interest is encoded by its corresponding nucleic acid sequence (for instance, an mRNA or genomic DNA). Accordingly, nucleic acid sequences encoding PSM peptides are contemplated herein, at least to make and use the PSM peptides of the disclosed compositions and methods.

In one example, in vitro nucleic acid amplification (such as polymerase chain reaction (PCR)) can be utilized as a method for producing nucleic acid sequences encoding PSM peptides. PCR is a standard technique, which is described, for instance, in *PCR Protocols: A Guide to Methods and Applications* (Innis et al., San Diego, Calif.: Academic Press, 1990), or *PCR Protocols, Second Edition (Methods in Molecular Biology*, Vol. 22, ed. by Bartlett and Stirling, Humana Press, 2003).

A representative technique for producing a nucleic acid sequence encoding a PSMα or PSM-mec peptide by PCR involves preparing a sample containing a target nucleic acid molecule that includes the PSM peptide-encoding nucleic acid sequence. For example, DNA or RNA (such as mRNA or total RNA) can serve as a suitable target nucleic acid molecule for PCR reactions. Optionally, the target nucleic acid molecule can be extracted from cells by any one of a variety of methods well known to those of ordinary skill in the art (for instance, Sambrook et al., *Molecular Cloning: A Laboratory Manual*, Cold Spring Harbor Laboratory Press, New York, 1989; Ausubel et al., *Current Protocols in Molecular Biology*, Greene Publ. Assoc. and Wiley-Intersciences, 1992). PSM peptides are, in some embodiments expressed in a variety of cell types; for example, prokaryotic and eukaryotic cells. In examples where RNA is the initial target, the RNA is reverse transcribed (using one of a myriad of reverse transcriptases commonly known in the art) to produce a double-stranded template molecule for subsequent amplification. This particular method is known as reverse transcriptase (RT)-PCR. Representative methods and conditions for RT-PCR are described, for example, in Kawasaki et al. (In *PCR Protocols, A Guide to Methods and Applications*, Innis et al. (eds.), 21-27, Academic Press, Inc., San Diego, Calif., 1990).

The selection of amplification primers will be made according to the portion(s) of the target nucleic acid molecule that is to be amplified. In various embodiments, primers (typically, at least 10 consecutive nucleotides of PSM peptide-encoding nucleic acid sequence) can be chosen to amplify all or part of a PSM peptide-encoding nucleic acid sequence. Variations in amplification conditions may be required to accommodate primers and amplicons of differing lengths and composition; such considerations are well known in the art and are discussed for instance in Innis et al. (*PCR Protocols, A Guide to Methods and Applications*, San Diego, Calif.: Academic Press, 1990). From a provided PSM peptide-encoding nucleic acid sequence, one skilled in the art can easily design many different primers that can successfully amplify all or part of a PSM peptide-encoding sequence.

As described herein, disclosed are nucleic acid sequences encoding PSMα and PSM-mec peptides. Though particular nucleic acid sequences are disclosed herein, one of skill in the art will appreciate that also provided are many related sequences with the functions described herein, for instance, nucleic acid molecules encoding conservative variants of a PSMα or PSM-mec peptide are disclosed herein. One indication that two nucleic acid molecules are closely related (for instance, are variants of one another) is sequence identity, a measure of similarity between two nucleic acid sequences or between two amino acid sequences expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, at least 95%, at least 98%, or at least 99% sequence identity to the sequence of interest, for example the PSM peptide of interest.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, at least 98%, or at least 99% sequence identity to the PSM peptide-encoding nucleic acid of interest.

Another indication of sequence identity is hybridization. In certain embodiments, PSM peptide-encoding nucleic acid variants hybridize to a disclosed (or otherwise known) PSM peptide-encoding nucleic acid sequence, for example, under low stringency, high stringency, or very high stringency conditions. Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, although wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

The following are representative hybridization conditions and are not meant to be limiting.
Very High Stringency (Detects Sequences that Share at Least 90% Sequence Identity)
 Hybridization: 5×SSC at 65° C. for 16 hours
 Wash twice: 2×SSC at room temperature (RT) for 15 minutes each
 Wash twice: 0.5×SSC at 65° C. for 20 minutes each
High Stringency (Detects Sequences that Share at Least 80% Sequence Identity)
 Hybridization: 5×-6×SSC at 65° C.-70° C. for 16-20 hours
 Wash twice: 2×SSC at RT for 5-20 minutes each
 Wash twice: 1×SSC at 55° C.-70° C. for 30 minutes each
Low Stringency (Detects Sequences that Share at Least 50% Sequence Identity)
 Hybridization: 6×SSC at RT to 55° C. for 16-20 hours
 Wash at least twice: 2×-3×SSC at RT to 55° C. for 20-30 minutes each.

One of ordinary skill in the art will appreciate that PSM peptide-encoding nucleic acid sequences of various lengths are useful for a variety purposes, such as for use as PSM peptide probes and primers. In some embodiments, an oligonucleotide can include at least 15, at least 20, at least 23, at least 25, at least 30, at least 35, at least 40, at least 45, at least 50 or more consecutive nucleotides of a PSM peptide-encoding nucleic acid sequence.

D. Therapeutic Methods and Pharmaceutical Compositions

An immunogenic PSMα peptide, PSM-mec peptide, combination of two or more PSMα peptides, combination of PSMα and PSM-mec peptides, or a combination of PSMα and/or PSM-mec and PSMβ peptides as disclosed herein can be administered to a subject in order to generate an immune response.

In some exemplary applications, compositions are administered to a subject who is at risk for exposure to MRSA, who has been exposed to MRSA, or who has a MRSA infection, in an amount sufficient to raise an immune response to *S. aureus* bacteria. Administration induces a sufficient immune response to inhibit infection with MRSA, slow the proliferation of the bacteria, inhibit their growth, or to reduce a sign or a symptom of a MRSA infection. Amounts effective for this use will depend upon the extent of exposure to MRSA bacteria, the route of entry of the bacteria into the body of the subject, the general state of the subject's health, and the robustness of the subject's immune system. A therapeutically effective amount of the compound is that which provides an objectively identifiable improvement in resistance to infection with MRSA.

In additional exemplary applications, compositions including PSM-mec peptides are administered to a subject who is at risk for exposure methicillin-resistant *staphylococcus*, who has been exposed to methicillin-resistant *staphylococcus*, or who has a methicillin-resistant *staphylococcus* infection, in an amount sufficient to raise an immune response to methicillin-resistant *staphylococcus* bacteria. Administration induces a sufficient immune response to inhibit infection with methicillin-resistant *staphylococcus*, slow the proliferation of the bacteria, inhibit their growth, or to reduce a sign or a symptom of a methicillin-resistant *staphylococcus* infection. Amounts effective for this use will depend upon the extent of exposure to methicillin-resistant *staphylococcus* bacteria, the route of entry of the bacteria into the body of the subject, the general state of the subject's health, and the robustness of the subject's immune system. A therapeutically effective amount of the compound is that which provides an objectively identifiable improvement in resistance to infection with methicillin-resistant *staphylococcus*. In particular examples, the methicillin-resistant *staphylococcus* is MRSA or MRSE.

An immunogenic PSMα peptide or PSM-mec peptide (or combination of PSM peptides) can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, or intravenous injection, but even oral, nasal, or anal administration is contemplated. In one embodiment, administration is by subcutaneous or intramuscular injection. To extend the time during which the protein is available to stimulate a response, the protein can be provided as an implant, an oily injection, or as a particulate system. The particulate system can be a microparticle, a microcapsule, a microsphere, a nanocapsule, or similar particle. (see, for instance, Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as interleukin (IL)-2, IL-6, IL-12, IL-15, RANTES, granulocyte macrophage colony stimulating factor (GM-CSF), tumor necrosis factor (TNF)-α, interferon (IFN)-α or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., (1998) *J. Surg. Oncol.* 68(2):122-38; Lotze et al., (2000), *Cancer J Sci. Am.* 6(Suppl 1):S61-6; Cao et al., (1998) *Stem Cells* 16(Suppl 1):251-60; Kuiper et al., (2000) *Adv. Exp. Med. Biol.* 465:381-90). These molecules can be administered systemically (or locally) to the host.

Some embodiments are pharmaceutical compositions including an immunogenic PSMα peptide, an immunogenic PSM-mec peptide, a combination of two or more PSMα peptides, a combination of PSMα and PSM-mec peptides, or a combination of PSMα and/or PSM-mec peptides and PSMβ peptides. In one specific embodiment, the immunogenic PSMα peptide, PSM-mec peptide (or combination of PSM peptides) is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for instance, Schmolka, (1977) *J. Am. Oil. Chem. Soc.* 54:110, and Hunter et al., (1981) *J. Immunol* 129:1244, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, (1984) *J. Immun.* 133:3167. The agent can be provided in an effective amount, for example between 0.5 and 10%, or in an amount between 1.25 and 5%.

The oil included in the composition is chosen to promote the retention of the antigen in oil-in-water emulsion, for example, to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include tetratetracontane and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

In one specific, non-limiting example, a pharmaceutical composition for intravenous administration would include about 0.1 ng to about 1000 mg of PSMα or PSM-mec peptide per dose, for instance 10 ng, 100 ng, 1 mg, 10 mg, or 100 mg. In another specific, non-limiting example, a pharmaceutical composition for intravenous administration would include a total of about 0.1 ng to about 1000 mg of a combination of PSMα peptides, PSMα and PSM-mec peptides, or a combination of PSMα and/or PSM-mec and PSMβ peptides per dose, for instance 10 ng, 100 ng, 1 mg, 10 mg, or 100 mg. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. For instance, in one embodiment the vaccine is administered in at least two doses, for instance 3, 4, 5, or 6 or more, with the second and subsequent doses administered at least a week after the first dose, for instance, one month, two months, three months or six months or more after the first dose. Generally, the dose is sufficient to inhibit infection with methicillin-resistant *staphylococcus* (such as MRSA or MRSE) without producing unacceptable toxicity to the subject.

E. Diagnostic Methods

Methods are disclosed herein wherein the disclosed PSM-mec peptide or a variant or fragment thereof is used to diagnose methicillin-resistant *staphylococcus* in a subject, and in particular MRSA or MRSE infection. In these embodiments, methods are provided for detecting methicillin-resistant *staphylococcus* in a biological sample, using one or more PSM-mec peptides. The PSM-mec peptide is used in an assay to determine the presence or absence of antibodies to the PSM-mec peptide in a biological sample (such as, but not limited to, whole blood, sputum, serum, plasma, saliva, cerebrospinal fluid, tissue sample, or oral or nasal swab) relative to a control. The presence of such antibodies indicates methicillin-resistant *staphylococcus* in the subject, and in particular MRSA or MRSE (such as MRSA or MRSE that includes a type II, III, or VIII SCCmec mobile genetic element). In some examples, the presence of anti-PSM-mec antibodies indicates the presence of methicillin-resistant *staphylococcus* (such as methicillin-resistant *S. aureus, S. epidermidis, S. saprophyticus, S. pseudintermedius,* or *S. sciuri*).

There are a variety of assay formats that can be used to detect antibodies in a sample (see, for example, Harlow and Lane, Antibodies: A Laboratory Manual, Cold Spring Harbor Laboratory (1988), which is incorporated herein by reference). In general, the presence or absence of methicillin-resistant *staphylococcus* in a subject may be determined by (a) contacting a biological sample obtained from a subject with one or more PSM-mec peptide; (b) detecting in the sample the presence (or absence) of an antibody that binds to the PSM-mec peptide; and (c) comparing the level of antibody with a control. The control can be a standard value, such as a pre-determined cut-off value. The control can be the amount of antibodies that specifically bind the PSM-mec peptide in a subject known to be infected with methicillin-resistant *staphylococcus*, or the amount of antibodies that specifically bind the PSM-mec peptide in a subject known not to be infected with methicillin-resistant *staphylococcus*.

In several embodiments, the assay involves the use of one or more PSM-mec peptides immobilized on a solid support. Antibodies that specifically bind the PSM-mec peptide bind to the solid support. The bound antibody can then be detected using a detection reagent that includes a detectable label. Suitable detection reagents include labeled antibodies that bind to the antibody/peptide complex. Suitable detection reagents also include second unlabeled antibodies that bind to the antibody/peptide complex and a third antibody that specifically binds the second antibody. Suitable detection reagents also include unbound peptide labeled with a reporter group (such as in a semi-competitive assay).

Alternatively, a competitive assay may be utilized, in which an antibody that binds to the peptide of interest is labeled with a reporter group is incubated with the sample. Following incubation, the antibody is then allowed to bind to the immobilized antigen after incubation of the antigen with the sample. The extent to which components of the sample inhibit the binding of the labeled antibody to the immobilized peptide is indicative of the reactivity of the sample with the immobilized peptide.

A solid support used in an assay disclosed herein can be any solid material to which the antigen may be attached. For example, the solid support can be a test well in a microtiter plate or a nitrocellulose or other suitable membrane. Alternatively, the solid support may be a bead or disc, such as glass, fiberglass, latex or a plastic material such as polystyrene or polyvinylchloride. The support can also be a magnetic particle or a fiber optic sensor, such as those disclosed, for example, in U.S. Pat. No. 5,359,681.

The peptide can be bound to the solid support using a variety of techniques known in the art. The binding of the peptide can be accomplished by a non-covalent association, such as adsorption, or covalent attachment, such as a direct linkage between the antigen and functional groups on the support or a linkage through a cross-linking agent.

In certain embodiments, the assay is an enzyme linked immunosorbent assay (ELISA). This assay can be performed by first contacting a PSM-mec peptide that has been immobilized on a solid support (such as in the well of a microtiter plate) with a sample in a manner such that that antibodies present within the sample that specifically bind the PSM-mec peptide bind the immobilized peptide. Unbound sample is then removed and a detection reagent capable of binding to the immobilized antibody/peptide complex is added. The amount of detection reagent that remains bound is determined using a method appropriate for the specific detection reagent. For example, the detection method can detect fluorescence or the presence of an enzymatic activity.

To determine the presence or absence of anti-PSM-mec peptide antibodies in the sample, the signal detected from the label that bound to the solid support is generally compared to a control. In one embodiment, the control is a standard value, such as the average mean signal obtained when the immobilized PSM-mec peptide is incubated with samples from an uninfected patient. In general, a sample generating a signal that is two or three standard deviations above the control is considered positive for methicillin-resistant *staphylococcus* infection. In another embodiment, the control value is determined using a Receiver Operator Curve, according to the method of Sackett et al., Clinical Epidemiology: A Basic Science for Clinical Medicine, Little Brown and Co., pp. 106 107 (1985). Briefly, in this embodiment, the control value is determined from a plot of pairs of true positive rates (sensitivity) and false positive rates (100% specificity) that correspond to each possible control value for the diagnostic test result. The control value on the plot that encloses the largest area is the most accurate cut-off value, and a sample generating a signal that is higher than the cut-off value determined by this method is considered positive. Alternatively, the cut-off value may be shifted to minimize the false positive rate, or to minimize the false negative rate. In general, a sample generating a signal that is higher than the cut-off value determined by this method is considered positive for methicillin-resistant *staphylococcus*.

In a related embodiment, the assay is performed in a rapid flow-through or strip test format, wherein the PSM-mec peptide is immobilized on a membrane, such as, but not limited to, nitrocellulose. In a flow-through test, antibodies within the sample bind to the immobilized peptide as the sample passes through the membrane. A detection reagent (for example, protein A-colloidal gold) binds to the antibody-polypeptide complex as the solution containing the detection reagent flows through the membrane. The detection of bound detection reagent can be performed as described above.

EXAMPLES

Example 1

PSMα Peptides as Vaccine Targets Against Methicillin-Resistant *Staphylococcus Aureus*

This Example demonstrates that PSMα peptides are major virulence determinants of *S. aureus*, and that their increased production in CA-MRSA contributes to the enhanced virulence of those strains compared to traditional HA-MRSA.

Among several putative determinants of CA-MRSA virulence, the Panton-Valentine leukocidin (PVL) has received most attention (Baba et al., *Lancet* 359, 1819-27, 2002; Diep et al., *Lancet* 367, 731-9, 2006; Vandenesch et al., *Emerg. Infect. Dis.* 9, 978-84, 2003; Gillet et al., *Lancet* 359, 753-9, 2002). A role of this lytic toxin as a virulence factor in cutaneous infection was suggested early (Grojec & Jeljaszewicz, *Zentralbl. Bakteriol. Mikrobiol. Hyg.* [A] 250, 446-55. 1981; Cribier et al., *Dermatology* 185, 175-80, 1992) and results from a mouse infection model indicate that purified PVL or heterologous over-expression of PVL contributes to the development of necrotizing pneumonia in laboratory strains of *S. aureus* (Labandeira-Rey et al., *Science* 315(5815):1130-3, 2007). This type of disease is rare among CA-MRSA infections (less than 2%; Fridkin et al., *N. Engl. J. Med.* 352, 1436-44, 2005), and whether PVL contributes to necrotizing pneumonia caused by CA-MRSA remains to be demonstrated. In contrast, results obtained using CA-MRSA isogenic PVL deletion strains and the respective murine infection models indicate that PVL does not play a significant role in CA-MRSA skin and soft tissue infections, which represent the most frequent manifestations of CA-MRSA disease, or in bacteremia (Voyich et al., *J. Infect. Dis.* 194, 1761-70, 2006). Thus, prior to this disclosure, the basis of virulence of CA-MRSA remained undefined.

Figure 1B:
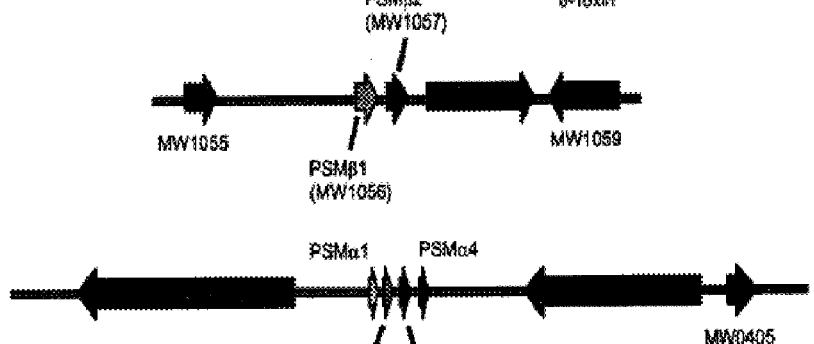
FIG. 1 includes three panels showing phenol-soluble modulins (PSMs) in *S. aureus*.
FIG. 1C shows production of PSMs (by RP-HPLC/ESI-MS) in 8-hour stationary phase cultures and RNAIII (by quantitative RT-PCR, in 4-hour late exponential phase cultures, at maximal expression of agr) of standard CA- and HA-MRSA strains. *, *S. aureus* strain whose genome has been sequenced.

As described herein, a group of peptides was identified in *S. aureus* using analytical reversed-phase HPLC/electrospray mass spectrometry and preparative reversed-phase chromatography with subsequent N-terminal peptide sequencing (FIG. 6). *S. aureus* was found to secrete 4 shorter (~20 amino acids, α-type) and 2 longer (~40 amino acids, β-type) PSM-like peptides (FIG. 1A), whose genes are arranged in 2 gene clusters (FIG. 1B). In addition, *S. aureus* produces δ-toxin, which is similar to the α-type PSMs. Of note, the PSMα genes have not been described previously, owing to the lack of similarity to PSM genes of *S. epidermidis* and the failure to exceed the threshold length for gene annotation.

Figure 1C:
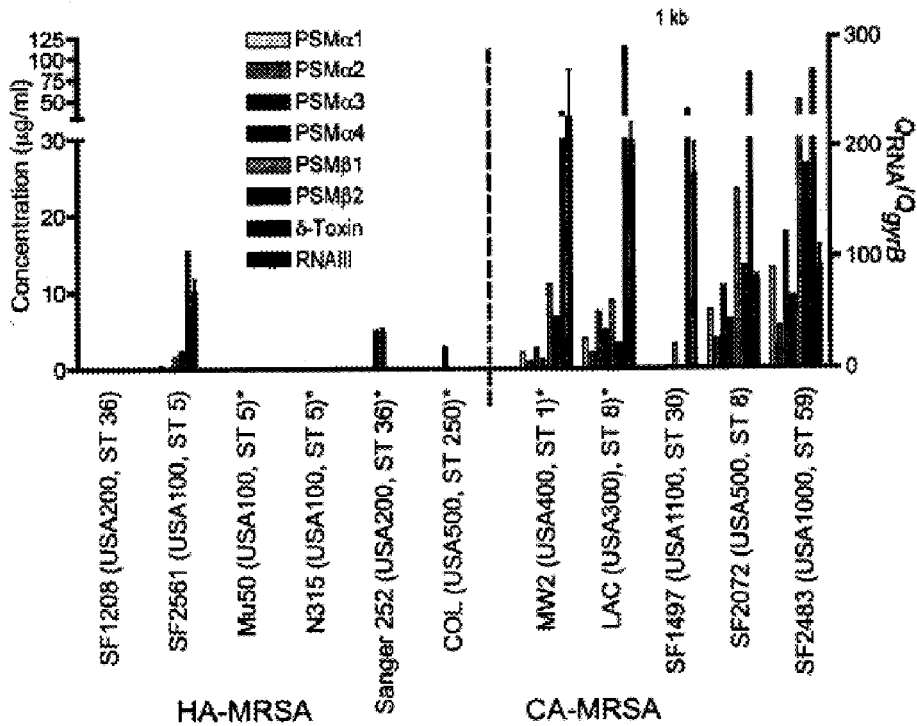

To demonstrate that PSMs determine the virulence of CA-MRSA, production of PSMs was compared in representative hospital-associated (HA)- and CA-MRSA strains. While the PSM genes occur in all sequenced *S. aureus* strains, dramatically higher in vitro PSM production was detected in the most prominent CA-MRSA compared to HA-MRSA (FIG. 1C), indicating that PSMs contribute to the enhanced virulence of CA-MRSA (Voyich et al., *J. Immunol.* 175, 3907-19, 2005). Isogenic gene deletion strains of the PSMα and PSMβ gene loci were constructed, and of the hld gene coding for the δ-toxin, in the CA-MRSA strains MW2 (USA400; Baba et al., *Lancet* 359, 1819-27, 2002) and LAC (USA300; Diep et al., *Lancet* 367, 731-9, 2006). MW2 was the first reported and sequenced CA-MRSA strain (Baba et al., *Lancet* 359, 1819-27, 2002) and USA300 currently accounts for most CA-MRSA infections in the US (Diep et al., *Lancet* 367, 731-9, 2006). RP-HPLC-ESI/MS analysis confirmed the specific absence of the particular PSM peptide(s) in the respective gene deletion strains (FIG. 6).

Figure 2A:
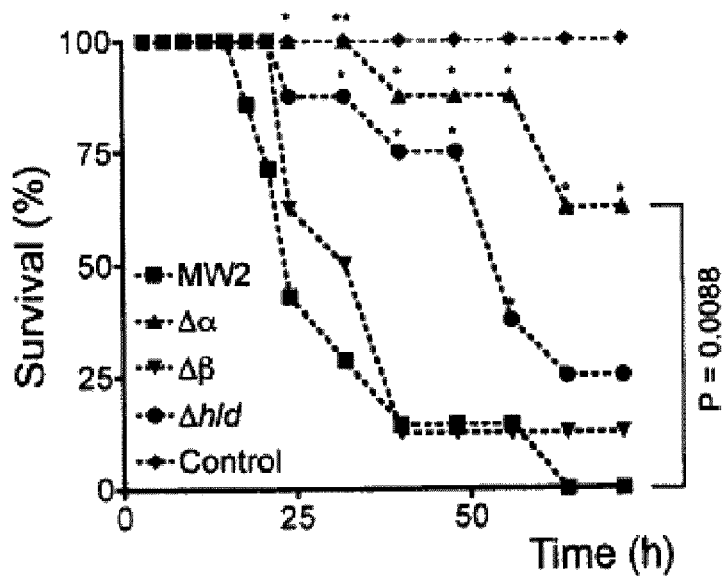
FIG. 2A shows a bacteremia model survival curve. CD1 Swiss female mice (n=7, wild-type, n=8, all others) were injected with $10^8$ CFUs of live *S. aureus* MW2 or isogenic PSM deletion mutant strains in 0.1 ml sterile saline via the tail vein. Control animals received sterile saline. Statistical analysis was performed using Fisher's exact test at each time point and the Kaplan-Meier test for survival curves (shown at the right).
Figure 2B:
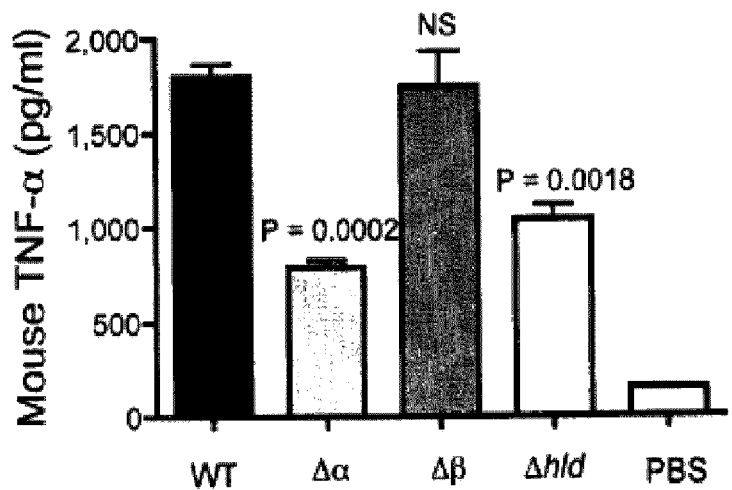
FIG. 2B is a graph showing the production of TNF-α in sera of mice in the bacteremia model at the end of the experiment. Sera of each group were pooled and TNF-α measurement was performed in triplicate.
Figure 2C:
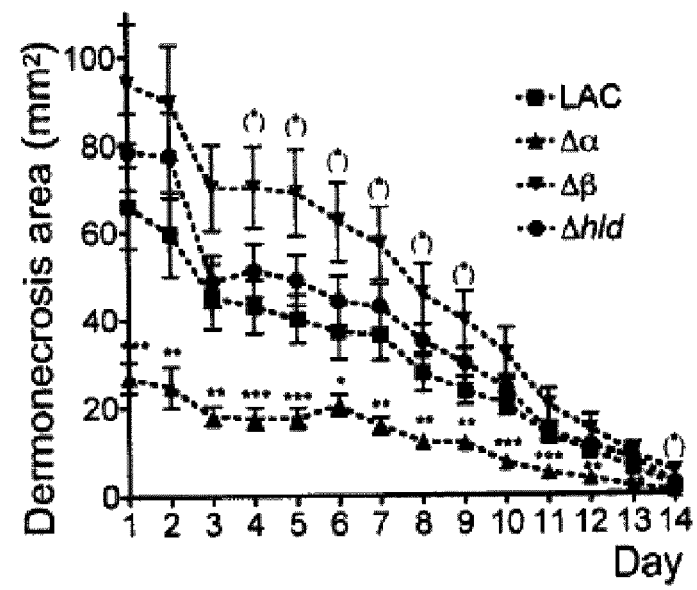
FIG. 2C is a graph showing results in a skin and soft tissue infection model. Crl: SKH1-hrBR mice (n=15 for all strains) were inoculated with 50 μl of $10^7$ live *S. aureus* LAC, isogenic PSM deletion mutant strains, or saline as control, in the right flank by subcutaneous injection. Skin lesion area dimensions were measured daily with a caliper.

The virulence of the PSM deletion strains was compared to the wild-type strains in murine abscess and bacteremia models (Voyich et al., *J. Infect. Dis.* 194, 1761-70, 2006). These models were selected based on the prevalence of CA-MRSA in skin and soft tissue infections (Moran et al., *N. Engl. J. Med.* 355, 666-74, 2006) and severe sepsis (Adem et al., *N. Engl. J. Med.* 353, 1245-51, 2005; Kravitz et al., *Clin. Infect. Dis.* 40, 941-7, 2005). MW2 (USA400), which typically causes sepsis in humans (Adem et al., *N. Engl. J. Med.* 353: 1245-51, 2005; Kravitz et al., *Clin. Infect. Dis.* 40, 941-7, 2005) was used for the bacteremia model. LAC (USA300), by far the most prominent cause of community-associated skin and soft tissue infection in the US (Moran et al., *N. Engl. J. Med.* 355:666-74, 2006), was used in a skin and soft tissue infection model. In the bacteremia model, there was significantly reduced mortality in the mice infected with the PSMα deletion strain and to a lesser extent, the δ-toxin-negative strain (FIG. 2A). Consistent with the sepsis data, levels of the inflammatory cytokine TNF-α were significantly reduced in blood samples of mice infected with those mutant strains (FIG. 2B). Additionally, there was a significantly decreased ability of the LAC PSMα deletion strain, but not of the other PSM deletion strains, to cause skin lesions in mice (FIGS. 2C, 2D). Together, these data demonstrate that α-type PSMs have an essential role in the most important manifestations of CA-MRSA induced disease.

Figure 3A:
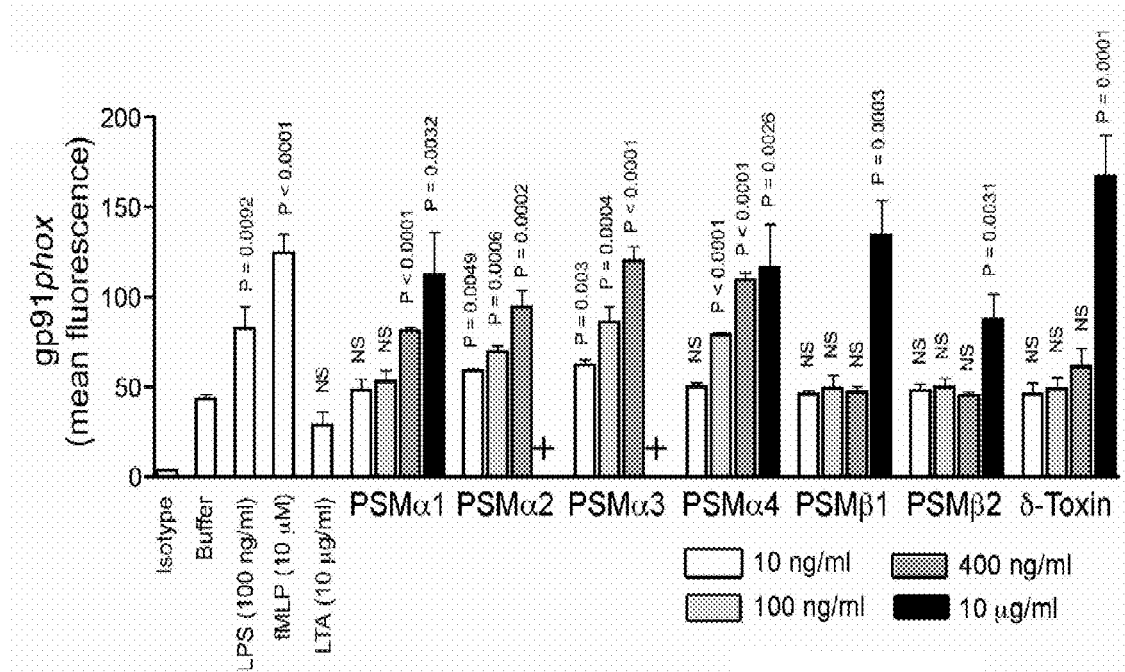
FIG. 3A is a graph showing surface expression of gp91phox, the heme-containing subunit of NADPH oxidase, a major component of the respiratory burst, with synthetic PSM peptides. (+, lysis of neutrophils occurred). P values are versus buffer.
Figure 3B:
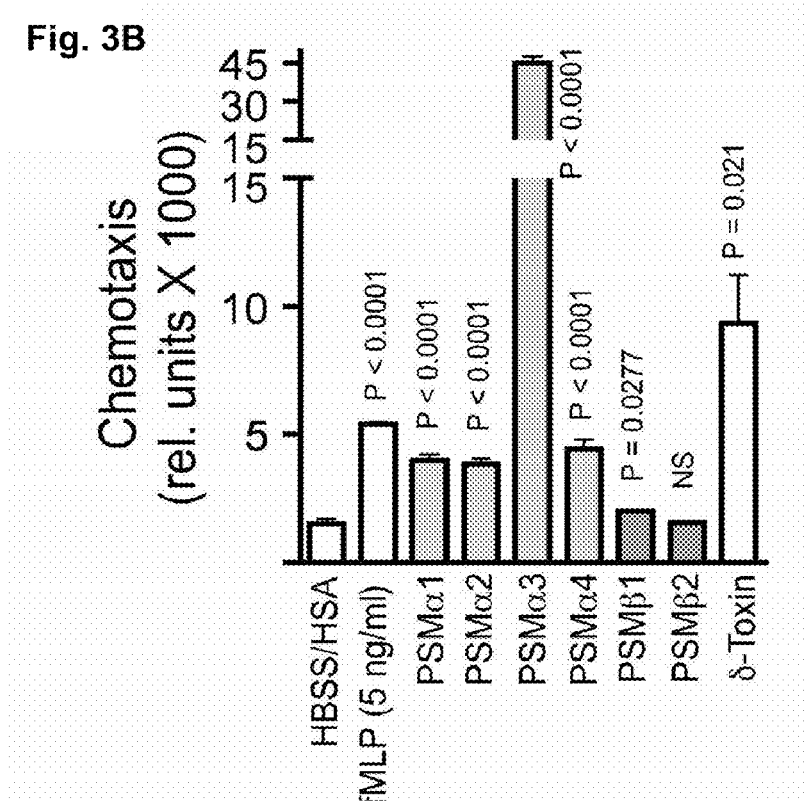
FIG. 3B is a graph showing chemotaxis with synthetic PSM peptides. PSM peptides were used at different concentrations (PSMα1, 5 μg/ml; PSMα2, 5 μg/ml; PSMα3, 500 ng/ml; PSMα4, 5 μg/ml; PSMβ1, 10 μg/ml; PSMβ2, 10 μg/ml; δ-toxin 2 μg/ml). To compare results, values were calculated for a theoretical concentration of 5 μg/ml. P values are versus HBSS/HSA (0.05%) control.
Figure 3C:
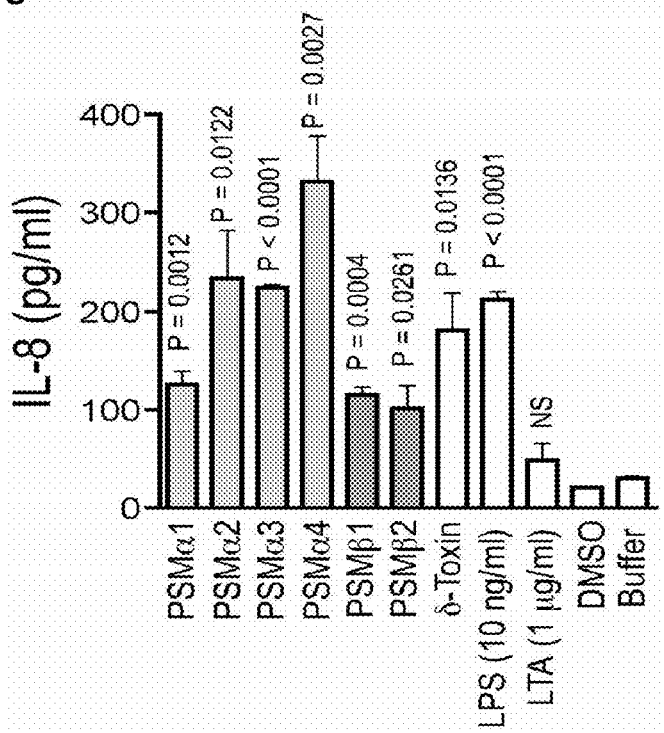
FIG. 3C is a graph showing secretion of IL-8 with synthetic PSM peptides at 10 μg/ml.
Figure 7:
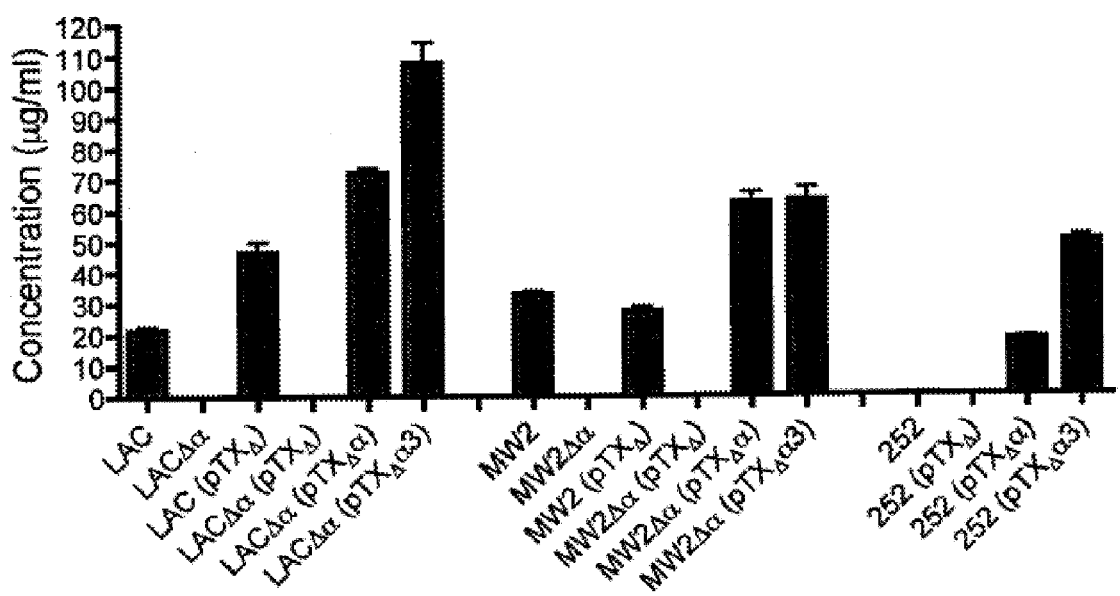
FIG. 7 is a graph showing production levels of PSMα3 in PSMα- and PSMα3-complemented, and control strains. Concentrations of PSMα3 were determined by RP-HPLC/ESI-MS and calibration was performed with synthetic PSMα3. The relative production of the other α-type PSMs in the PSMα-complemented strains (complemented with the entire PSMα locus) was equivalent to the relations shown in FIG. 1 and similar to PSMα3 in absolute concentrations. All strains were grown with the addition of tetracycline (12.5 μg/ml). Production levels of the PSMs encoded on the complementation plasmids were not decreased when strains were grown without tetracycline, indicating that the plasmids are stable under the used conditions (growth with shaking for 16 hours at 37° C.).

To demonstrate the mechanism by which PSM peptides promote virulence, the ability of these molecules to alter phagocyte function was tested, focusing on neutrophils as the most important cell type responsible for the elimination of invading bacteria. Synthetic PSMs primed neutrophils for activation (as determined by expression of gp91phox and CD11b, FIG. 3A and FIG. 7), provoked neutrophil chemotaxis and $Ca^{2+}$ flux (FIG. 3B and FIG. 7), and induced release of the cytokine IL-8 (FIG. 3C), but not TNF-α or IL-1β. PSMα peptides, particularly PSMα3, generally showed the most pronounced pro-inflammatory activity. In contrast, PSMs failed to increase expression of IL-8, TNF-α or IL-1β in PBMCs (peripheral blood mononuclear cells), or Mono Mac 6 cells. Thus, the pro-inflammatory activity of the PSMs is very specific and the increased levels of TNF-a as a general indicator of inflammation that was observed in the bacteremia model likely are secondary effects of immune cell cross-activation. Changes in IL-8 production by neutrophils after interaction with the HA- and CA-MRSA wild-type, PSM deletion, and PSM complemented strains (for production levels of complemented strains see FIG. 8) were consistent with the results obtained using synthetic PSMs (FIG. 7C, FIG. 3C), indicating that α-type PSMs, particularly PSMα3, have a pronounced influence on the pro-inflammatory activity of CA-MRSA. Taken together, these results demonstrate that *S. aureus* PSMα peptides (i) efficiently activate and trigger an inflammatory response in human neutrophils, and (ii) contribute dramatically to staphylococcal virulence.

Figure 4A:
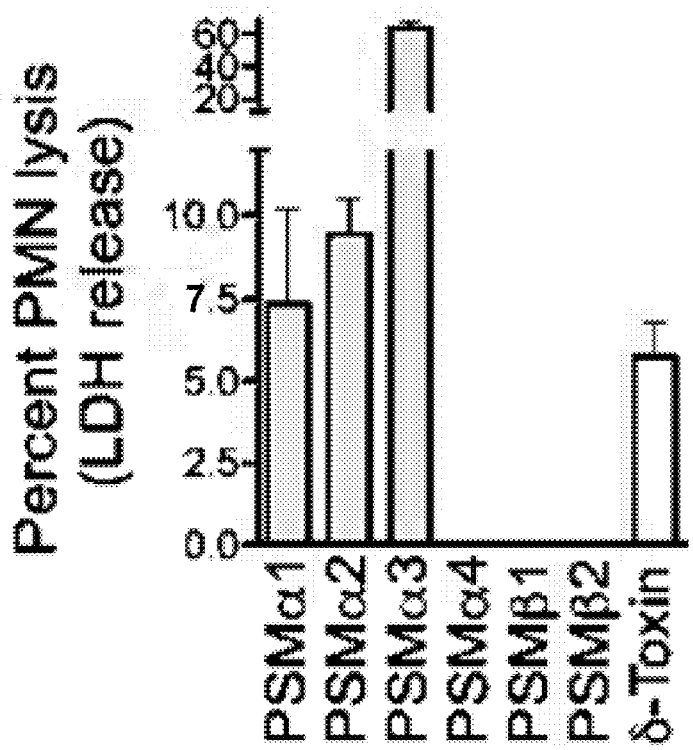
FIG. 4A is a graph showing human neutrophil lysis, measured by release of lactate dehydrogenase (LDH) activity, with synthetic PSM peptides at 10 μg/ml.
Figure 4B:
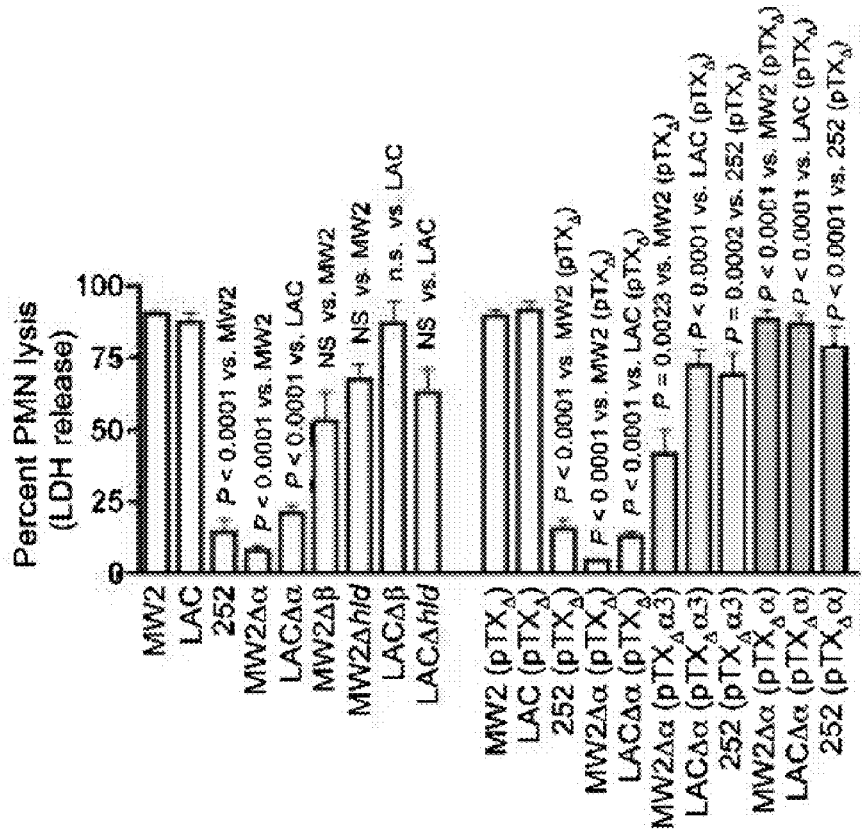
FIG. 4B is a graph showing human neutrophil lysis, measured by release of LDH activity, with culture filtrates of wild-type, PSM gene deletion and complemented CA- and HA-MRSA strains. Data represent means±SEM of at least three independent measurements.
Figure 4C:
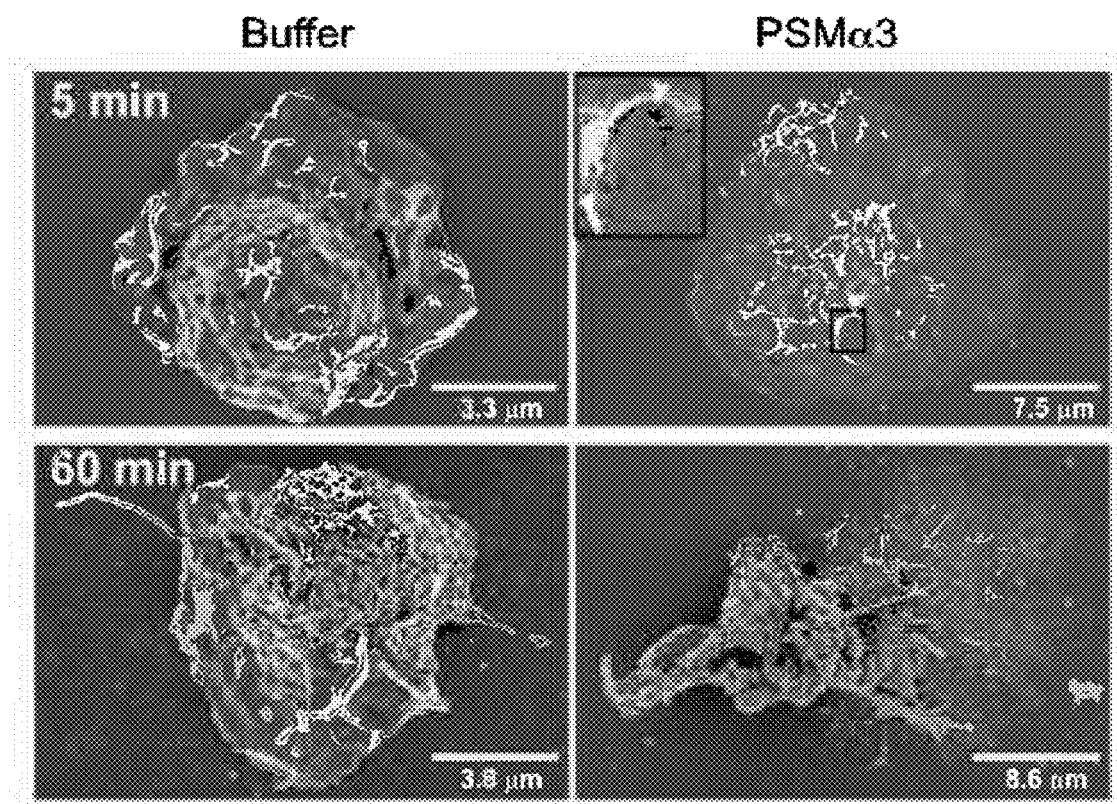
FIG. 4C is a series of digital images showing in vitro lysis of human neutrophils with synthetic PSMα3. Neutrophils were incubated with PSMα3 (10 μg/ml) and observed by scanning electron microscopy at the time intervals indicated, in comparison to untreated controls.

Inasmuch as enhanced virulence of CA-MRSA has been linked to leukolytic activity (Voyich et al., *J. Immunol.* 175, 3907-19, 2005), it was then shown that PSMαs lyse human neutrophils in vitro using synthetic PSMs. PSMs of the α-type caused significant lysis, particularly PSMα3 (FIG. 4A). Accordingly, clarified culture media from CA-MRSA PSMα deletion and HA-MRSA strains had dramatically reduced capacity to cause lysis of human neutrophils (FIG. 4B). Lytic activity of these strains was entirely restored by genetic complementation with a plasmid expressing all α-type PSMs, and almost completely restored with a plasmid expressing PSMα3 alone, indicating that most of the noted cytolytic activity of CA-MRSA is due to this peptide. In contrast, the PSMβ and δ-toxin-negative strains did not show significantly reduced lysis of human neutrophils. When monitored by scanning electron microscopy, neutrophils showed signs of priming (for instance, flattening) and structures indicating that the integrity of the plasma membrane was compromised within 5 minutes of exposure to PSMα3 (FIG. 4C). After 60 minutes, many neutrophils were completely destroyed. PSMs, mainly those of the α-type, also caused lysis of erythrocytes, which may contribute to the development of disease (FIG. 9).

Figure 4D:
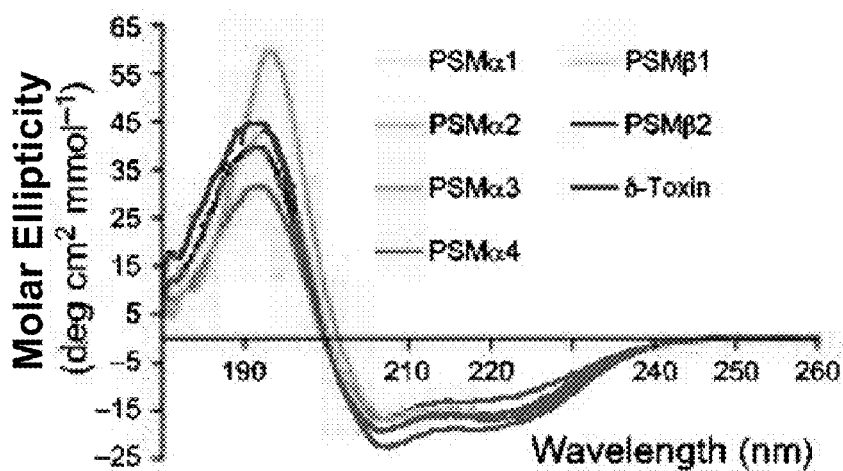
FIG. 4D shows the circular dichroism spectra of synthetic PSM peptides with N-formyl-methionine taken in 50% trifluorethanol. The peak at ~190 nm is indicative of α-helicity.
Figure 4E:
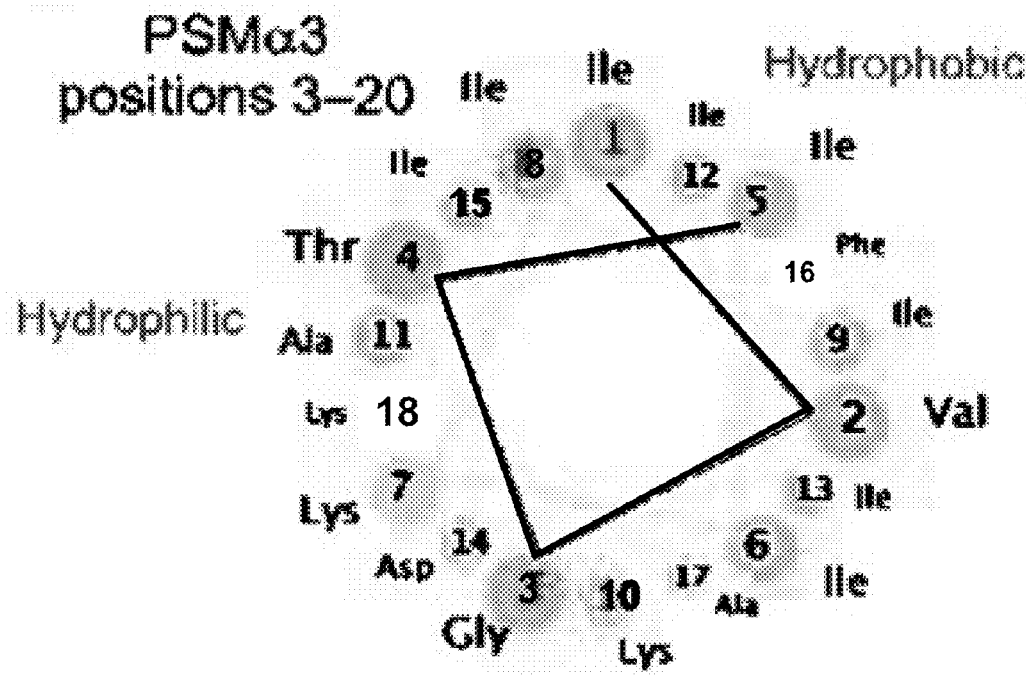
FIG. 4E shows the helical wheel computation for PSMα3.
Figure 4F:
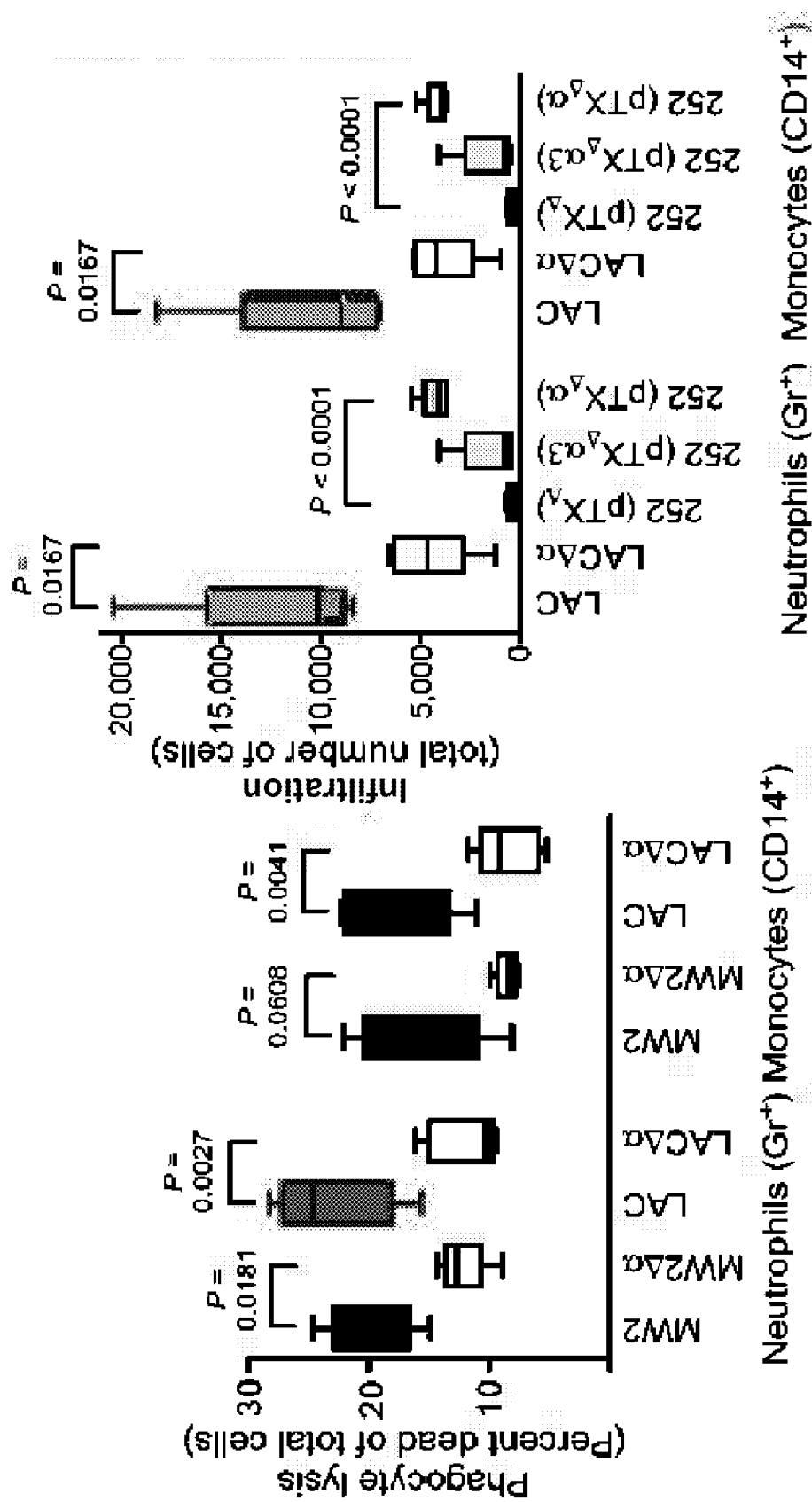
FIG. 4F is a pair of graphs showing the infiltration and killing of human leukocytes in a murine peritonitis model. Two hours after infection with the bacteria, neutrophils and monocytes were counted in peritoneal exudates, and dead and live cells were distinguished, using flow cytometry. The number of mice was n=5 for all samples except n=4 for MW2 samples (the results from one mouse in the MW2 wild-type and PSMα deletion strain samples were not included because of extensive bleeding).
Figure 4G:
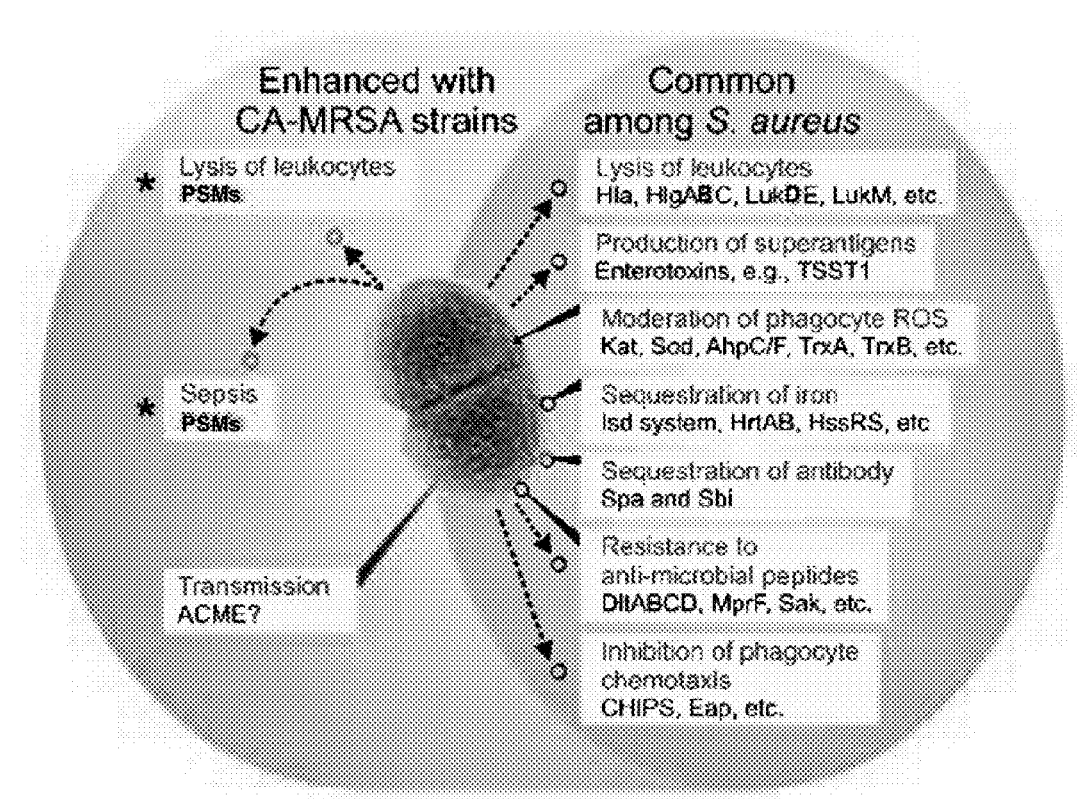
FIG. 4G shows the interaction of *S. aureus* with mechanisms of innate host defenses (shown on the right). Enhanced development of bacterial sepsis and leukocyte lysis by PSMs (*), as shown herein, contributes to the exceptional virulence of CA-MRSA.
Figure 5A:
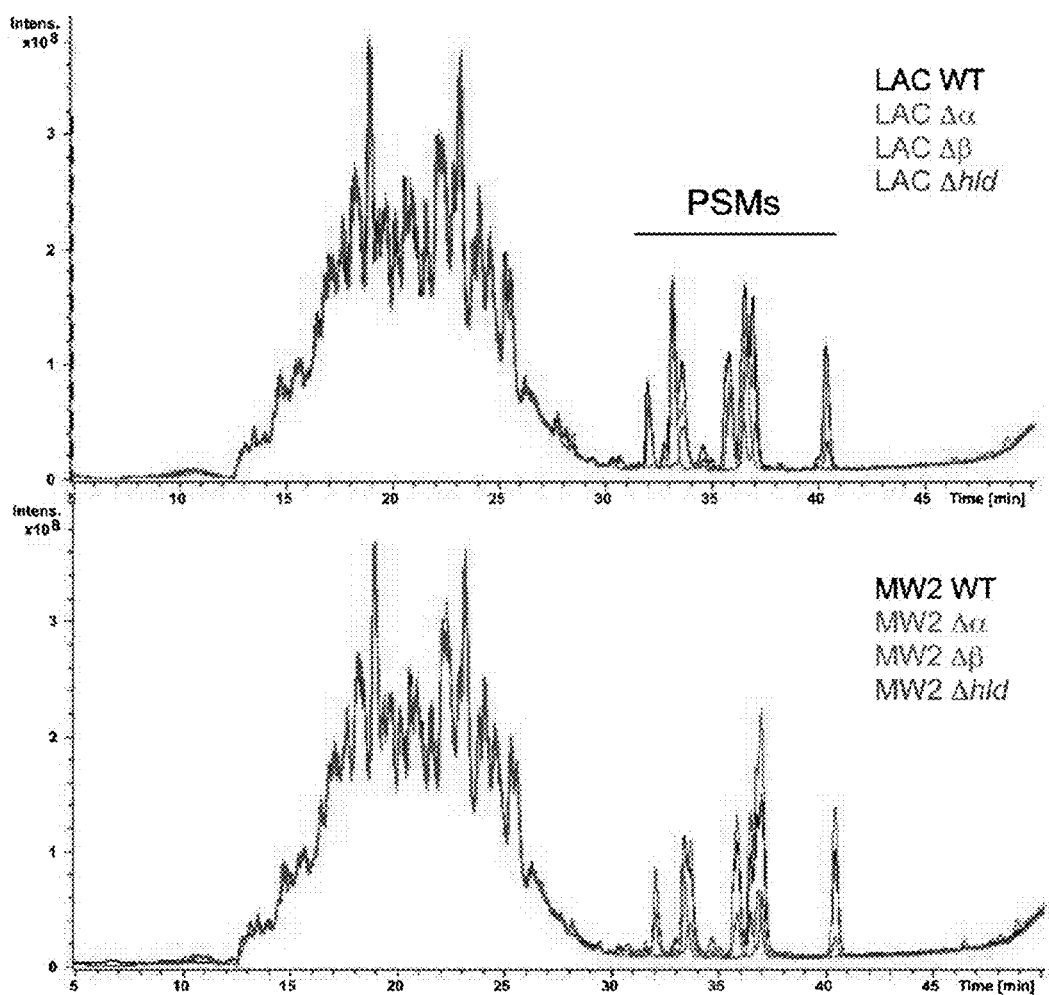
FIG. 5A shows RP-HPLC/ESI-MS of culture filtrates as total ion chromatograms. Chromatography was performed using a Pharmacia SOURCE 5 μRPC ST 4.6/150 column and a water/acetonitrile gradient in 0.1% trifluoroacetic acid from 0 to 100% acetonitrile in 50 minutes at a flow rate of 1 ml/minute.
Figure 5B:
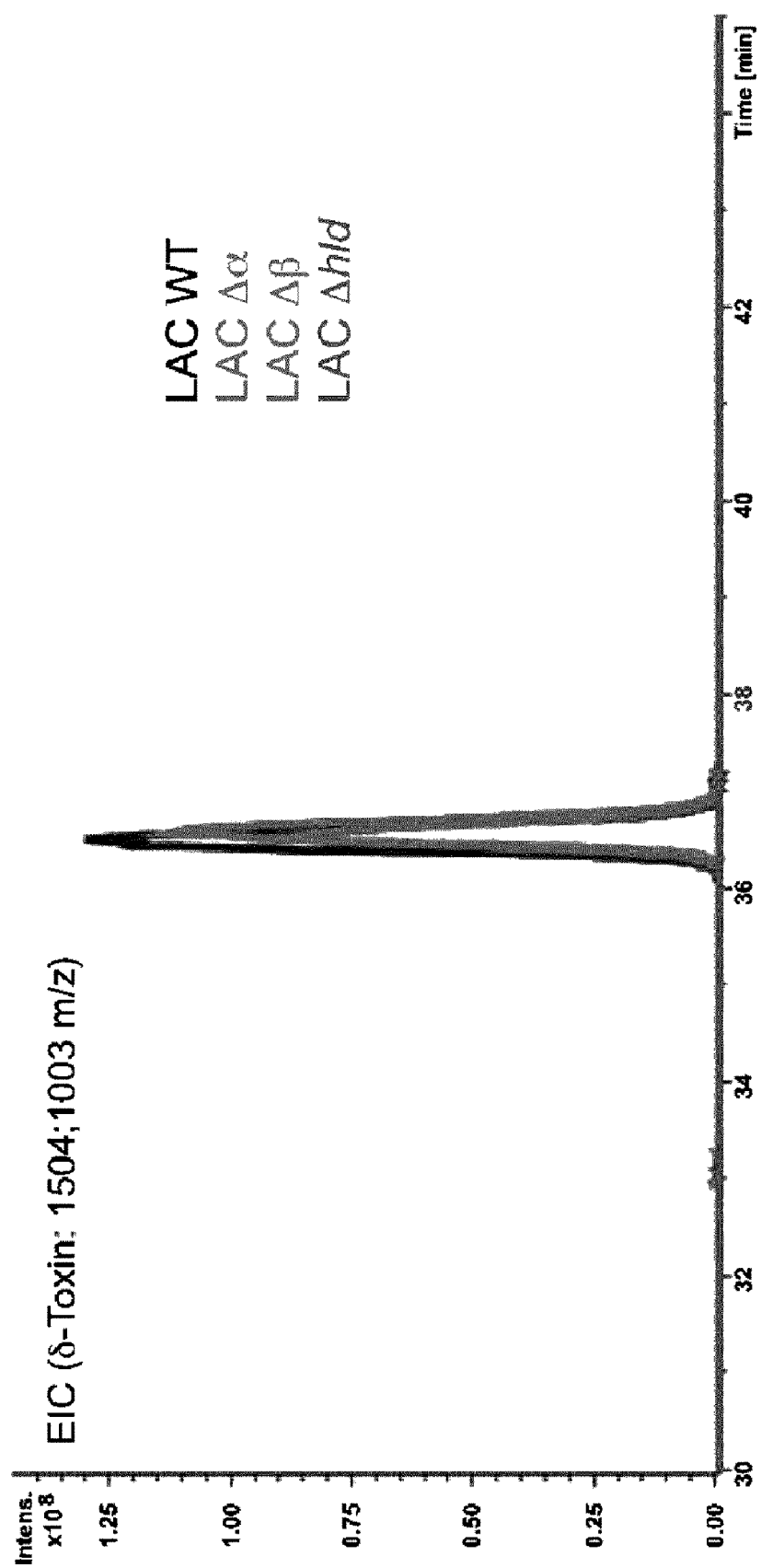
FIG. 5B shows extracted ion chromatograms (EIC). Chromatography was performed as described in Example 3. In addition to verifying the absence of the respective deleted gene products, these analyses demonstrated that in the PSM gene deletion strains, the concentrations of the respective other PSM peptides were not significantly altered. EICs for the δ-Toxin of LAC wild-type and PSM gene deletion strains are shown as an example. For the very late eluting PSMα4, according to the HPLC results, the concentration in the Δhld strain was lower than in the wild-type. However, as all α-type PSMs are encoded in a putative operon, this discrepancy is likely due to physico-chemical interaction with the column material rather than to different production levels. Accordingly, it has been previously observed that the later eluting peptides require the presence of δ-Toxin to elute completely.
Figure 5C:
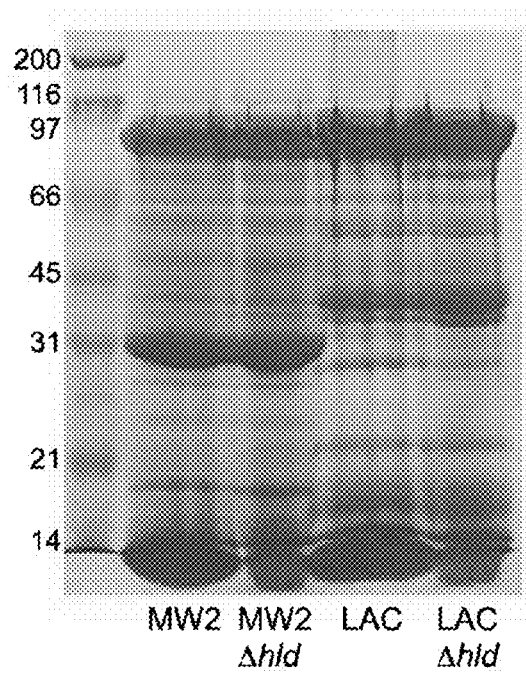
FIG. 5C shows SDS-PAGE of TCA-precipitated exoproteins of CA-MRSA wild-type strains and corresponding hld deletion strains.
Figure 5D:
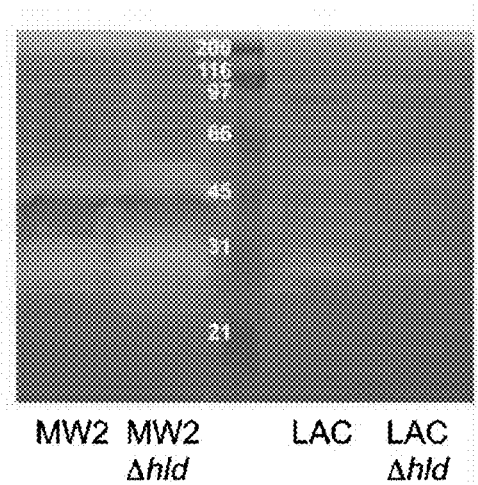
FIG. 5D shows Zymographic analysis of TCA-precipitated exoproteins of CA-MRSA wild-type strains and corresponding hld deletion strains. SDS-polyacrylamide gels (12%) were copolymerized with skim milk at a final concentration of 0.125 mg/ml. These analyses demonstrated that production of secreted proteins was not altered in the hld deletion strains.
Figure 6A:
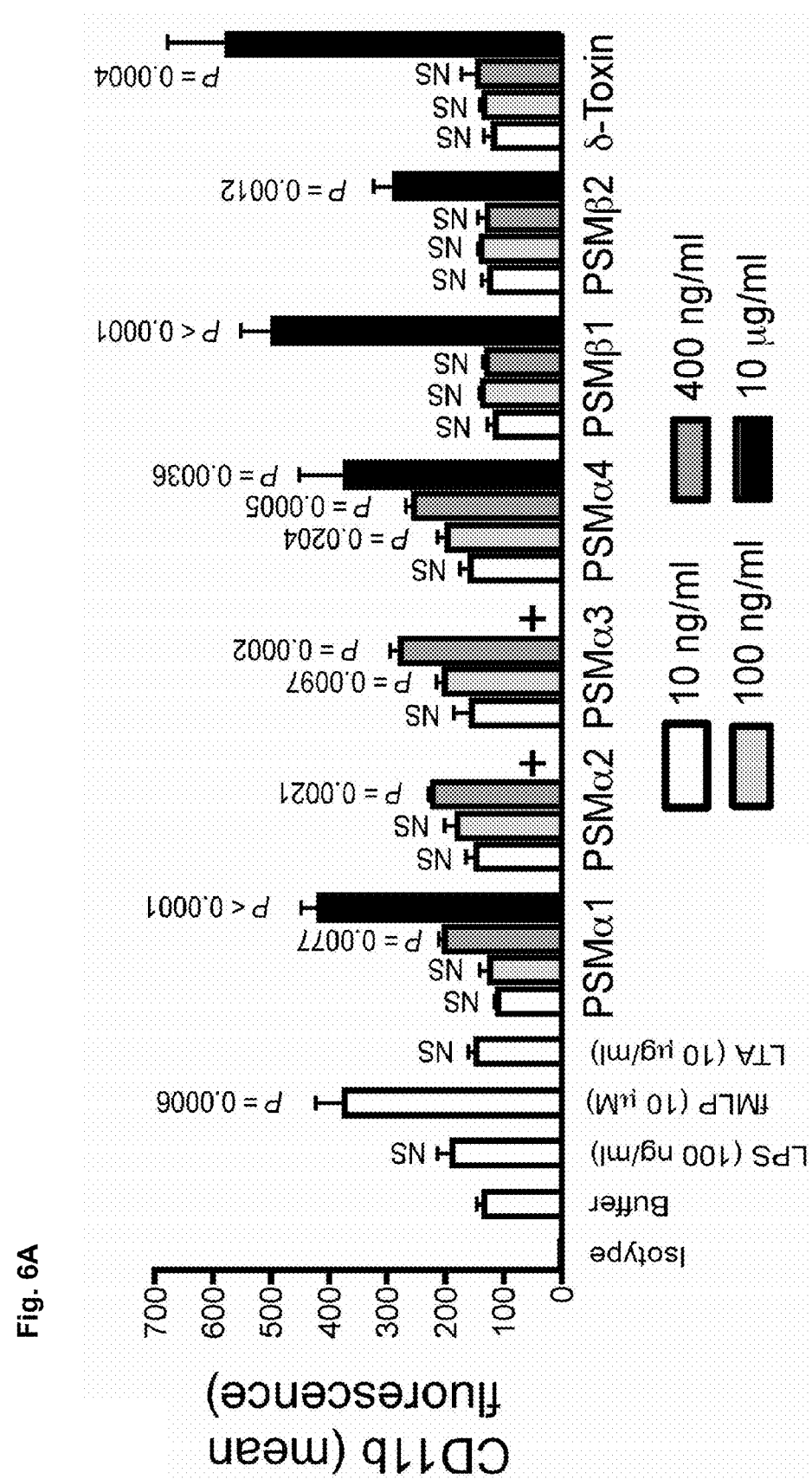
FIG. 6A shows surface expression of CD11b, a β-integrin located in neutrophil secretory vesicles and specific granules, on human neutrophils incubated with synthetic PSM peptides. The symbol "+" indicates that lysis of neutrophils occurred. P values are versus buffer.
Figure 6B:
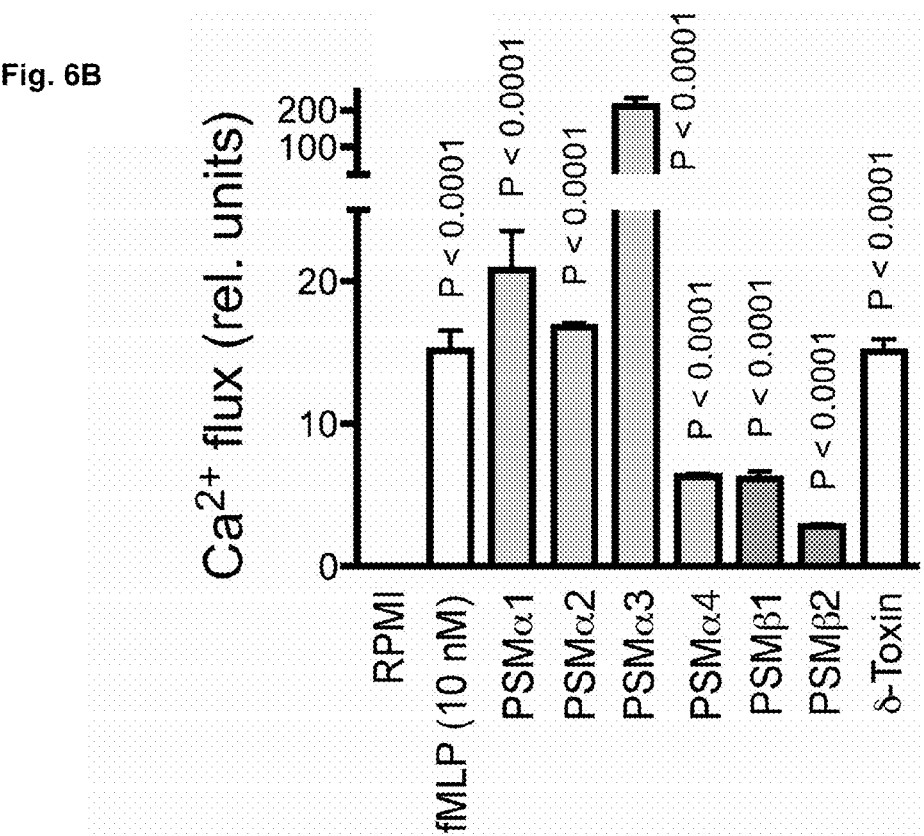
FIG. 6B shows calcium influx in human neutrophils with synthetic PSM peptides. PSM peptides were used at different concentrations (PSMα1, 1 μg/ml; PSMα2, 1 μg/ml; PSMα3, 100 ng/ml; PSMα4, 2.5 μg/ml; PSMβ1, 2.5 μg/ml; PSMβ2, 5 μg/ml; δ-Toxin 1 μg/ml). To compare results, values were calculated for a theoretical concentration of 1 μg/ml. P values are versus RPMI control.
Figure 6C:
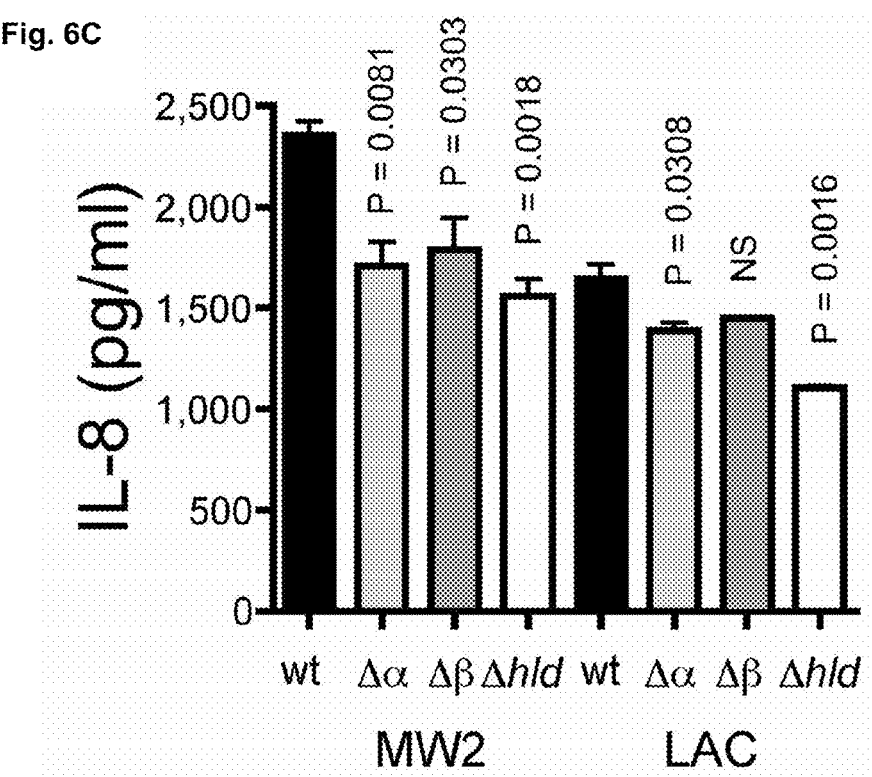
FIGS. 6C and 6D show secretion of IL-8 with culture filtrates of wild-type in comparison to PSM deletion strains (FIG. 6C), and complemented CA- and HA-MRSA and corresponding wild-type and PSMα deletion control strains (FIG. 6D).
Figure 6D:
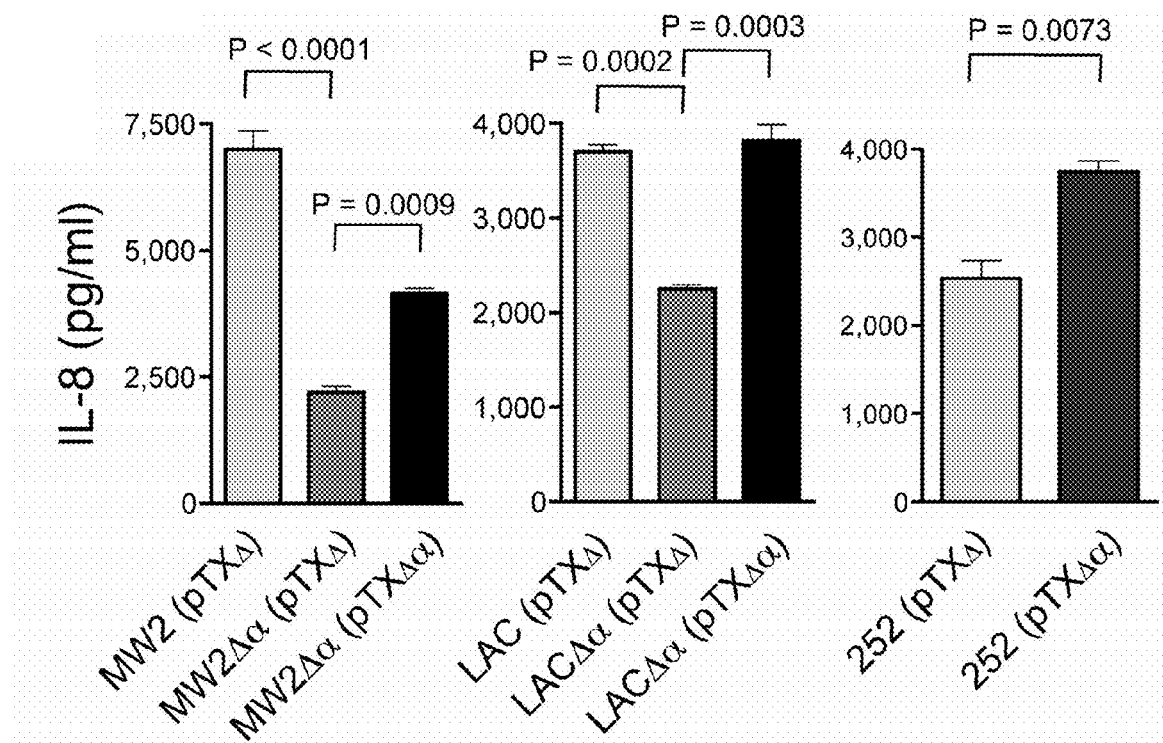
Figure 10A:
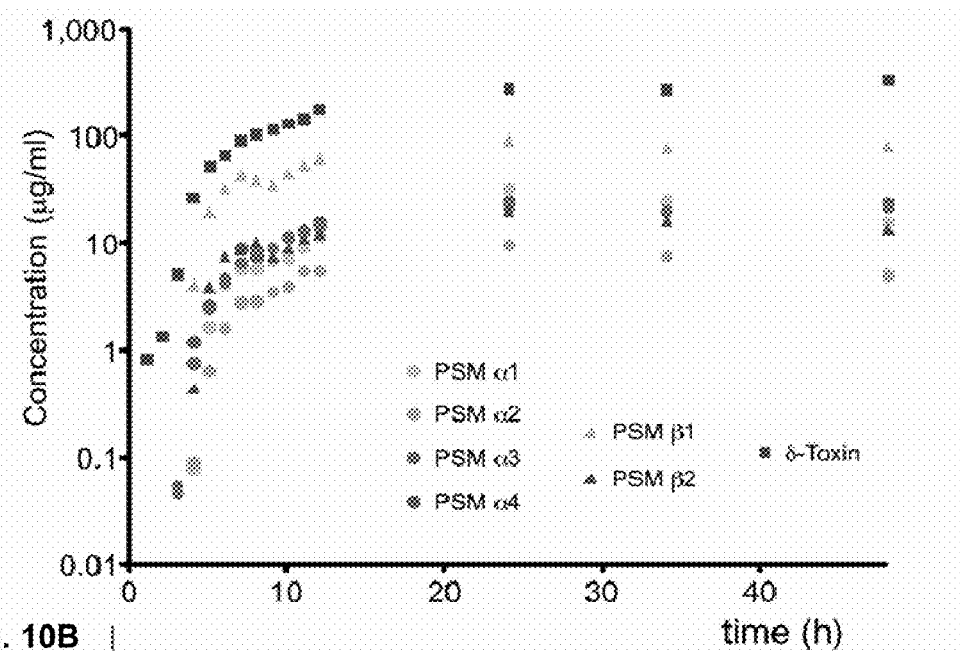
FIG. 10A shows growth-dependent production of PSMs. PSM concentration during growth in TSB in a shaken flask culture was determined by RP-HPLC/ESI-MS. Data are means of three independent measurements.
Figure 10B:
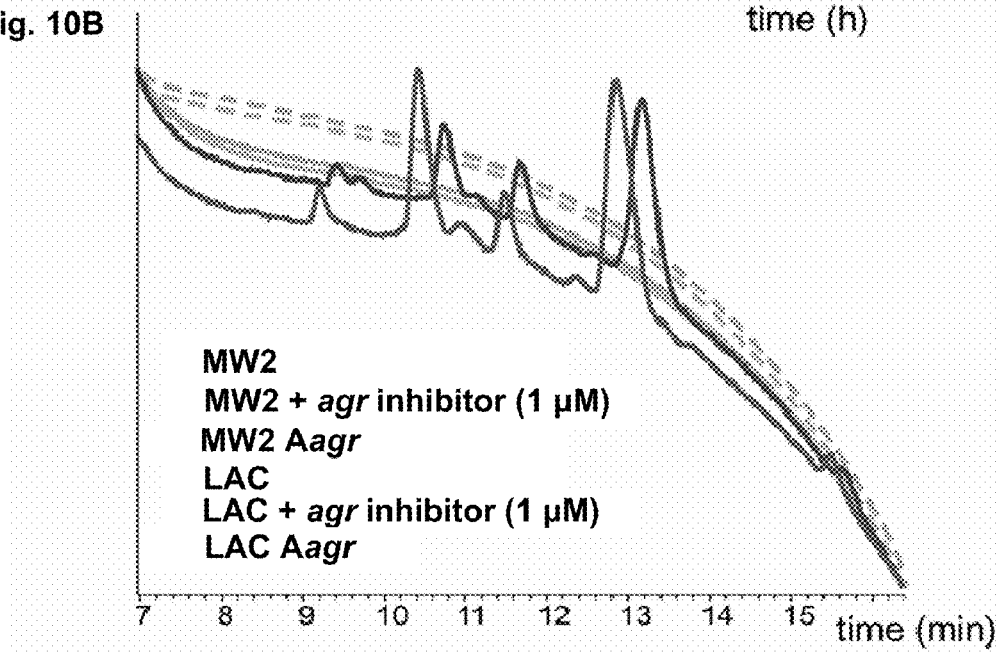
FIG. 10B shows control of PSM production by agr. CA-MRSA wild-type strains were grown to stationary phase (8 hours) with or without addition of 1 µM of agr-specific inhibitor (the cross-inhibiting agr signal of *S. epidermidis*), and compared to isogenic agr deletion strains (dashed curves). Culture filtrate samples were analyzed by RP-HPLC. The UV signal at 214 nm is shown.

Without being bound by theory, the membrane-damaging activity of PSMαs most likely is due to their strong α-helicity (FIG. 4D) and amphipathy (FIG. 4E), which are typical features of pore-forming peptides (Mellor et al., *Biochim Biophys Acta* 942, 280-94, 1988). Importantly, although *S. aureus* is known to produce factors that may cause neutrophil lysis in vitro, prior to this disclosure it was not understood which molecules are responsible for the elimination of neutrophils in vivo. In a murine peritonitis model, neutrophil and monocyte infiltration and lysis was significantly increased after infection with CA-MRSA wild-type strains compared to the isogenic PSMα deletion strains. In addition, significantly increased neutrophil and monocyte infiltration was observed with the PSMα-complemented HA-MRSA strain 252 compared to the parental strain (FIG. 4F, FIG. 10). These findings demonstrate that α-type PSMs contribute significantly to the lysis of leukocytes in vitro and in vivo, and to a large extent are responsible for the enhanced cytolytic activity of CA-MRSA strains.

Figure 11:
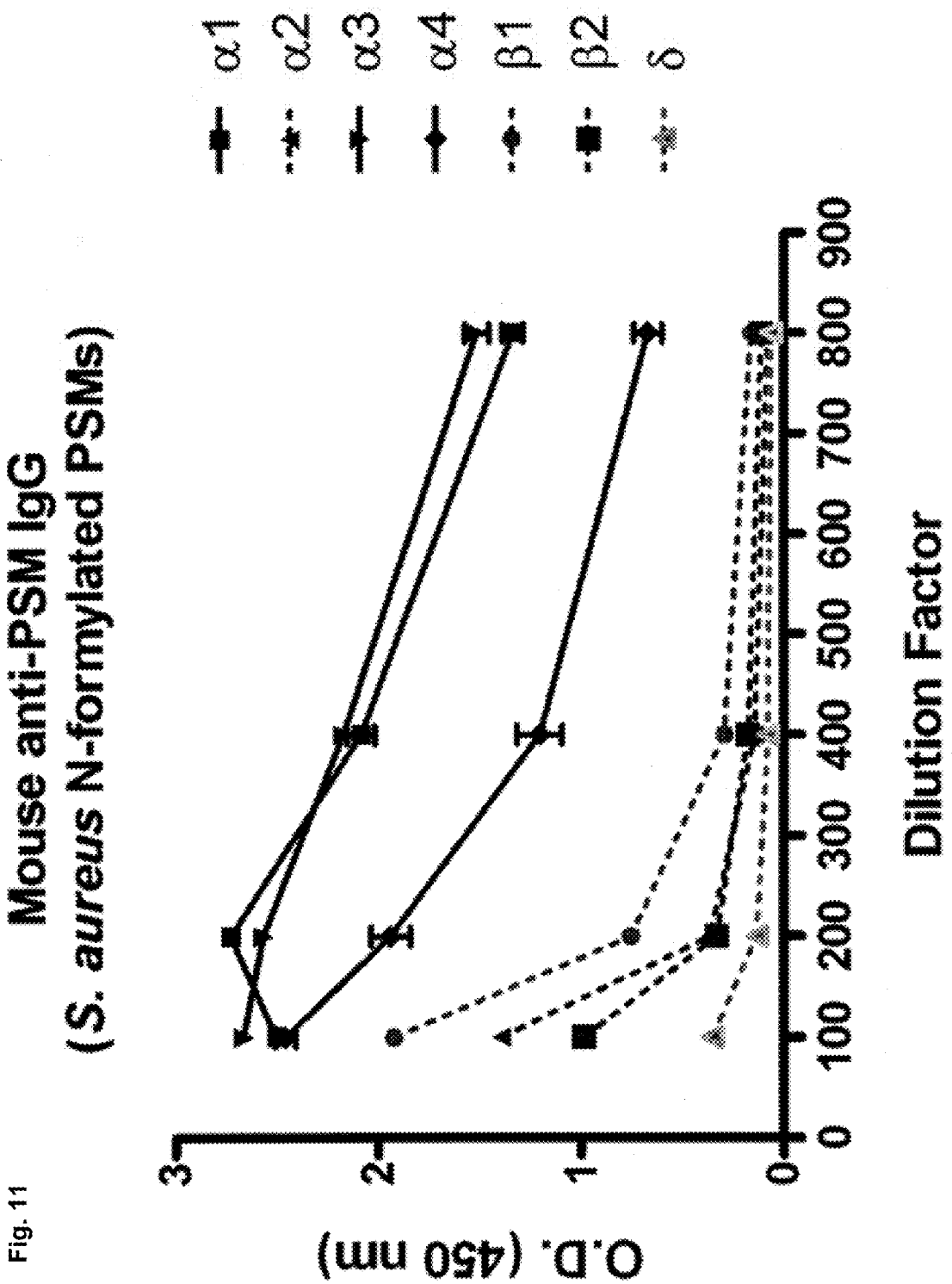
FIG. 11 is a graph showing that immunization with N-formylated synthetic PSM peptides triggers antibody production in vivo.

Collectively, these results indicate that a primary role of PSMαs in pathogenesis is to destroy leukocytes and thus, PSMαs play a key role in the evasion of innate host defense by *S. aureus* (FIG. 5). However, as PSMαs also trigger the inflammatory response, the bacteria must be able to limit PSMα secretion to times at which these cells can be efficiently inactivated. Using isogenic agr deletion strains in CA-MRSA and agr-specific inhibitor peptides, we found that all *S. aureus* PSMs are under tight control of the agr quorum-sensing system (FIG. 11). This mechanism links gene expression to bacterial cell density via a secreted bacterial signal, limiting the production of target genes to a time when the signal molecules achieve a high concentration, such as by confinement in the neutrophil phagosome (Kong et al., *Int J Med Microbiol* 296, 133-9, 2006; Redfield, *Trends Microbiol* 10, 365-70, 2002). Thus, it is presumably due to control by agr that PSMs are produced at the right time to fulfill their task in pathogenesis and are repressed when production would jeopardize bacterial survival. Furthermore, strain-to-strain differences in PSM production appear to be in part caused by differential agr activity. Production of RNAIII, the regulatory molecule of the agr system, was in general lower in HA-MRSA compared to CA-MRSA. However, the production of PSMs, especially α-type PSMs, was not entirely correlated with RNAIII levels (FIG. 1C), indicating that agr-independent regulation also contributes to the low PSMα levels observed in HA-MRSA. Notably, these findings highlight the importance of gene expression and regulation in the endeavor to understand the basis of CA-MRSA virulence.

Taken together, PSMα peptides are major virulence determinants of *S. aureus* and their increased production in CA-MRSA contributes to the enhanced virulence of those strains compared to traditional HA-MRSA (Voyich et al., *J Immunol* 175, 3907-19, 2005) Importantly, the newly identified peptides encoded by the PSMα gene cluster represent the first molecules for which a significant effect has been demonstrated on the ability of CA-MRSA strains to cause disease in animal infection models.

Example 2

Methods for FIGS. 1-5

This Example describes the methods used in generating the data shown in FIGS. 1-5.

A. Bacterial Strains

HA- and CA-MRSA were standard strains whose genomes have been sequenced (Baba et al., *Lancet* 359, 1819-27, 2002; Diep et al., *Lancet* 367, 731-9, 2006; Holden et al., *Proc Natl Acad Sci USA* 101, 9786-91, 2004; Gill et al., *J Bacteriol* 187, 2426-38, 2005; Kuroda et al., *Lancet* 357, 1225-40, 2001) or prototypical strains from a UCSF collection (Diep et al., *J Infect Dis* 193, 1495-503, 2006). Bacteria were grown in tryptic soy broth (TSB).

B. Reversed-Phase Chromatography/Mass Spectrometry

Bacterial strains were inoculated 1:100 from a pre-culture grown overnight, grown for 8 hours in TSB, and culture filtrates were obtained by centrifugation at 10,000×g for 15 minutes. For preparative chromatography, samples were precipitated with trichloroacetic acid, the precipitate was dissolved in 8 M urea, and samples were injected onto a HR 16/10 column packed with SOURCE 15PHE material (GE Healthcare). PSM-containing fractions were collected and injected on a Zorbax SB-C18 9.4 mm×25 cm column (Agilent) for further purification. Columns were run with a water-acetonitrile gradient in 0.1% trifluoroacetic acid as described (Yao et al., *J Infect Dis* 191, 289-98, 2005). After acid removal of the N-terminal formyl group (Shively et al., *Anal Biochem* 120, 312-2, 1982), purified PSMs were analyzed by Edman sequencing. For analytical chromatography, an Agilent 1100 system coupled to an Agilent TrapSL mass spectrometer and a Zorbax SB-C8 2.1×30 mm column (Agilent) were used as described (Vuong et al., *Cell Microbiol* 6, 753-9, 2004). For PSM quantification, culture filtrates were directly injected, and calibration was performed with synthetic PSMs. The two most abundant peaks of the electrospray mass spectra obtained were used for peak integration. Evaluation was performed with Agilent Quant Analysis software.

C. Construction of PSM and agr Gene Deletion Strains and Complementation Plasmids The PSMα and PSMβ deletion strains were constructed by allelic replacement with a spectinomycin resistance cassette as described (Vuong et al., *Infect Immun* 68, 1048-53, 2000). The hld deletion strains were constructed in a way so as not to interfere with the function of the regulatory RNA molecule (RNAIII), in whose encoding DNA it is embedded (Novick et al., *Embo J* 12, 3967-75, 1993). These strains were constructed by alteration of the start codon of the δ-toxin hld gene using the procedure of Bae & Schneewind (*Plasmid* 55, 58-63, 2006). The two PCR fragments used in that procedure were amplified using oligonucleotides that contained an MfeI site at the place of the hld start codon, resulting in a one base change from ATG to ATT and abolishing translation of hld. All PSM deletion strains were confirmed by analytical PCR with genomic DNA and RP-HPLC/ESI-MS of culture filtrates (FIG. 6). In vitro growth of the deletion strains was indistinguishable from the respective wild-type strain. In addition to measuring PSM production, the secreted protein protease profiles of the hld deletion strains were tested by SDS-PAGE and zymographic analysis (Vuong et al., *Infect Immun* 68, 1048-53, 2000) to ensure that the regulatory function of RNAIII was not affected (FIG. 6). Deletion strains in agr were produced by phage transduction from strain RN6911.

Figure 8A:
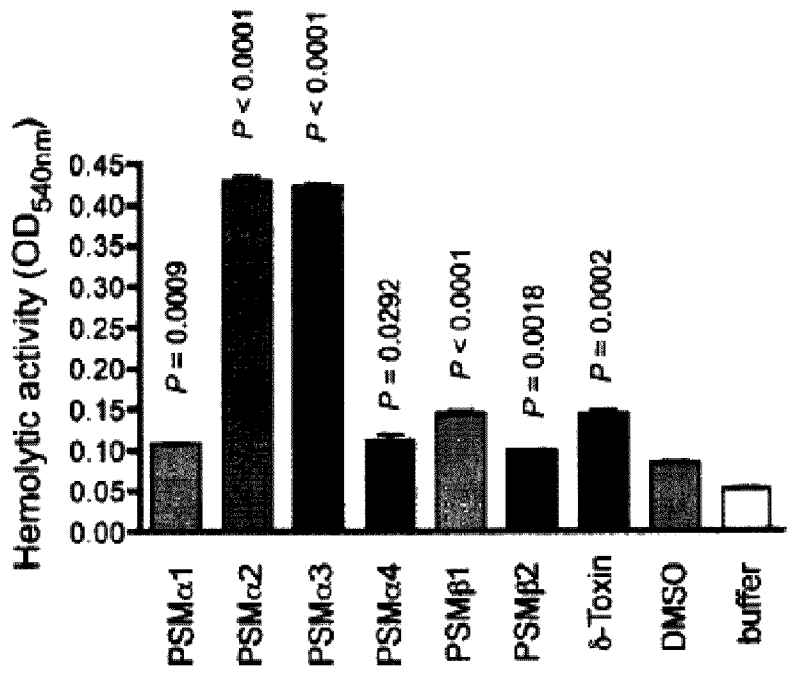
FIG. 8A shows hemolysis with synthetic PSM peptides.
Figure 8B:
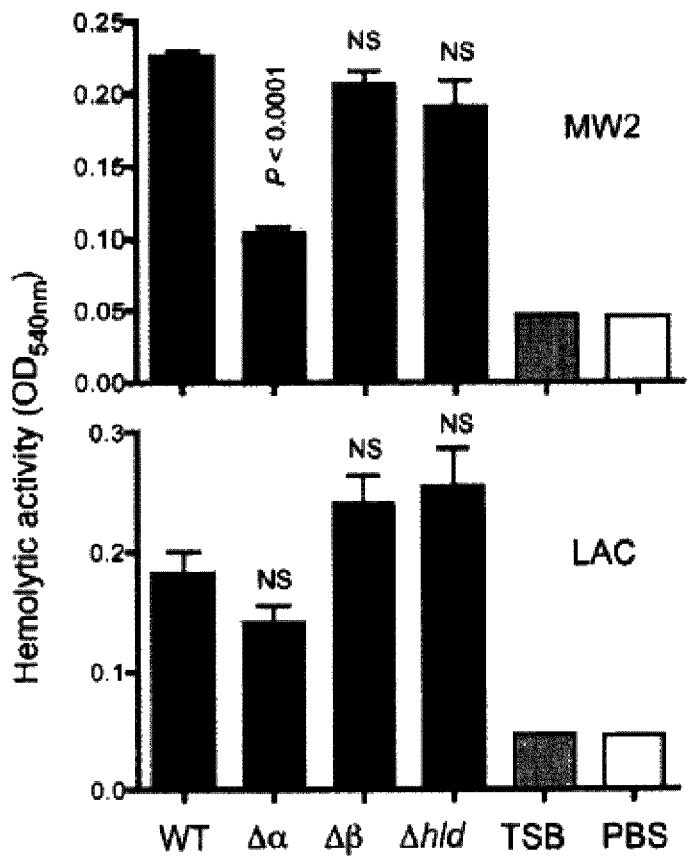
FIG. 8B shows hemolysis with culture filtrates.

The pTX$_A$ plasmids were derived from plasmid pTX15, by deletion of the 5' part of the xylR repressor gene via digestion with NdeI and PstI and re-ligation, to achieve high-level, constitutive expression of genes cloned under control of the xyl promoter (FIG. 8). The PSMα gene locus or the PSMα3 gene were PCR-amplified using chromosomal DNA of strain MW2 as template, digested with BamHI/MluI, ligated into BamHI/MluI digested pTX$_A$ and transformed into *S. aureus* RN4220 and subsequently in the target strains. These plasmids confer resistance to tetracycline, which was added to cultures at 12.5 μg/ml. In vitro growth of PSM-expressing strains with pTX$_A$ derivatives was indistinguishable from that of the respective control strains.

D. Quantitative Reverse-Transcription (RT) Polymerase Chain Reaction (PCR)

Oligonucleotide primers and probes were designed with Primer Express software (version 2.0; Applied Biosystems) and synthesized by Applied Biosystems. The experiments were performed in triplicate as described (Yao et al., *J Infect Dis* 193, 841-848, 2006), with 16S rRNA as a control.

E. Circular Dichroism (CD) Measurement

The structures of synthetic PSM peptides were analyzed by CD spectroscopy on a Jasco spectropolarimeter model J-720 instrument. Solutions of PSM peptides, each at 1.0 mg/ml, were prepared in 50% trifluoroethanol. Measurements were performed in triplicate and the resulting scans were averaged, smoothed, and the buffer signal was subtracted.

F. Human Neutrophil Isolation

PMNs were isolated from venous blood of healthy volunteers in accordance with protocols approved by the Institutional Review Board for Human Subjects, NIAID, and the University of Tubingen, Germany, as described (Voyich et al., *J Infect Dis* 194, 1761-70, 2006; de Haas et al., *J Exp Med* 199, 687-95, 2004).

G. Neutrophil Chemotaxis and Calcium Ion Fluxes

Neutrophils were subjected to a brief hypotonic shock with pyrogen-free water (Sigma), washed, and suspended at $5 \times 10^6$ cells/ml in HBSS containing 0.05% human serum albumin (HSA; CLB). Chemotaxis of neutrophils was determined by using fluorescently-labeled neutrophils that migrated through a membrane fitted into an insert of a 24-well microtiter plate transwell system (Costar) containing a prewetted 3-µm-pore-size polycarbonate filter as described (de Haas et al., *J Exp Med* 199, 687-95, 2004). For measurement of calcium ion fluxes, $5 \times 10^6$ neutrophils/ml were loaded with 2 µM Fluo-3-AM (Molecular Probes) in RPMI containing 0.05% HSA (RPMI-HSA) for 20 minutes at room temperature under agitation, washed twice with buffer, and resuspended in RPMI-HSA at $10^6$ cells/ml. Calcium fluxes were analyzed with a FACScalibur (Becton Dickinson).

H. Priming of Human Neutrophils

Priming of PMNs by synthetic PSMs was determined by increased surface expression of CD11b and gp91phox (granule exocytosis). PMNs were incubated with 10-10,000 ng/ml PSM, 10 µM fMLP, 10 ng/ml lipopolysaccharide, or 10 µg/ml lipoteichoic acid in 96-well tissue culture plates at 37° C. with rotation for 60 minutes. The assay was terminated by centrifuging cells at 4° C. for 8 minutes at 350×g. Cells were washed twice in cold Dulbecco's phosphate-buffered saline and stained with and isotype control antibody (BD Biosciences) or those specific for CD11b (mAb 44, BD Biosciences) or gp91phox (mAb 7D533). Propidium iodide (0.5 µg/ml) was used to identify dead cells. PMNs were analyzed on a FACSCalibur flow cytometer (Becton Dickinson) and dead cells were excluded with a single gate. Percent positive neutrophils were determined with a marker defined by the boundary of the isotype-matched control antibody.

I. Lysis of Human Neutrophils

Lysis of PMNs by synthetic PSMs or clarified *S. aureus* culture media was determined essentially as described (Voyich et al., *J Infect Dis* 194, 1761-70, 2006; Voyich et al., *J Immunol* 175, 3907-19, 2005). Synthetic PSMs (1 or 10 µg/ml) were added to wells of a 96-well tissue culture plate containing $10^6$ PMNs and plates were incubated at 37° C. for up to 3 hours. At the desired times, PMN lysis was determined by release of lactate dehydrogenase (LDH; Cytotoxicity Detection Kit, Roche Applied Sciences). Alternatively, wild-type and isogenic mutant *S. aureus* strains were cultured for 18 hours at 37° C. in 50 ml TSB with shaking using a 100 ml flask. Bacteria were removed by centrifugation and culture media were sterilized by filtration and stored at −80° C. in aliquots until used. Culture medium was diluted 1:10 in RPMI/H, mixed with human PMNs ($10^6$) and tested for its ability to cause PMN lysis.

J. Scanning Electron Microscopy

For scanning electron microscopy, PMNs were fixed, washed, and mounted on stubs as described previously (Voyich et al., *J Immunol* 175, 3907-19, 2005). After mounting on stubs, samples were coated lightly with chromium using an ion beam sputterer (South Bay Technology, Inc.), and examined with a Hitachi S5200 field emission scanning electron microscope (Hitachi High Technologies America). Digital images were collected and adjusted for brightness and contrast with Photoshop CS (Adobe Systems).

K. Measurement of Cytokine Production

After isolation and washing, PMN or PBMC were resuspended in RPMI 1640 medium (Sigma) supplemented with 10% human serum, 2 mM L-glutamine, 100 U/ml penicillin, 100 µg/ml streptomycin, 2 mM sodium pyruvate, and 10 mM HEPES. Cells were distributed to a 96-well culture plate at 200 µl and $5 \times 10^5$ cells per well. Synthetic PSM peptides or filtered bacterial culture supernatants were diluted in fresh culture medium and added to the plate at 100 µl/well. Plates were incubated at 37° C. in a 5.5% $CO_2$ incubator for 5 hours. Then, the plate was centrifuged at 1500 rpm for 10 minutes, and supernatant was harvested from each well. Mono Mac 6 cells were obtained from DSMZ (Germany), and were grown in RPMI 1640 plus 10% heat inactivated fetal bovine serum (HyClone), 2 mM L-glutamine, 10.0 units/ml penicillin, 10.0 µg/ml streptomycin, 0.2× non-essential amino acid solution, and OPI medium supplement (Sigma). Cells were grown in T75 culture flasks in a 37° C. $CO_2$ incubator and harvested by centrifugation. After removal of supernatant, cells were resuspended in fresh culture medium, counted, and distributed into a 96-well cell culture plate at 100 µl and $2.5 \times 10^5$ cells per well. Phorbol 12-myristate 13-acetate (Sigma) was added to a final concentration of 2.5 ng/ml for cell pre-stimulation. The plate was incubated in a 37° C. $CO_2$ incubator for 3 hours. At the end of the pre-stimulation period, synthetic PSM peptides were diluted in culture medium and added to the cells at 100 µl/well. Cells were incubated in a 37° C. $CO_2$ incubator for 20-22 hours, and the plate was centrifuged at 1500 rpm for 10 minutes. Human TNF-α, IL-1β, IL-8, and mouse TNF-α were measured in the culture supernatants with commercial ELISA assay kits (R&D systems) according to the manufacturer's instructions.

L. Murine Bacteremia, Skin Abscess, and Peritonitis Models

CD1 Swiss female mice and Crl: SKH1-hrBR hairless mice (outbred, immunocompetent) were obtained from Charles River Laboratories and were between 4 and 6 weeks of age at the time of use. *S. aureus* strains were grown to mid-exponential phase, washed once with sterile PBS, then resuspended in PBS at $1 \times 10^8$ CFUs/100 µl (bacteremia model) or $1 \times 10^7$ CFUs/50 µl (abscess model) as described (Voyich et al. (2006) *J Infect Dis* 194, 1761-70). For the bacteremia model, each mouse was injected with $10^8$ CFUs of live *S. aureus* in 0.1 ml sterile saline via the tail vein. Control animals received sterile saline only. After inoculation, animal health and disease advancement were monitored every 3 hours for the first 24 hours, then every 8 hours for up to 72 hours Animals were euthanized immediately if showing signs of respiratory distress, mobility loss, or inability to eat and drink. All surviving animals were euthanized at 72 hours. At the time of death, serum samples were harvested from test animals for mouse TNF-α ELISA tests.

For the abscess model, Crl: SKH1-hrBR mice were anesthetized with isoflurane, and inoculated with 50 µl of $10^7$ live *S. aureus* strains or saline in the right flank by subcutaneous injection. Test animals were examined at 24-hour intervals for a total of 14 days. Skin lesion dimensions were measured daily with a caliper. Length (L) and width (W) values were applied to calculate the area of lesions using the formula of L×W. All animals were euthanized after completion of the entire procedure.

For the peritonitis model, CD1 Swiss female mice were injected intraperitoneally with 0.1 ml of $10^7$ live *S. aureus*. Two hours after the inoculation, animals were euthanized by an isoflurane overdose, and 6.0 ml of RPMI medium containing 10% FBS was injected into the abdominal cavities. Mice were surgically opened and 4.0 ml of exudates were collected with 23 G needles. The collected exudates were aliquoted to 0.4 ml per sample, centrifuged at 1500 rpm for 5 minutes, and cell pellets were resuspended in 100 ml of staining buffer (PBS containing 1% goat serum). Samples were stained with fluorescein isothiocyanate (FITC)-conjugated anti-mouse Ly-6G (clone 1A8, BD Biosciences) as neutrophil marker and allophycocyanin (APC)-conjugated anti-mouse CD14 (clone Sa2-8, eBioscience) as a marker for monocytes and macrophages, or with appropriate isotype control antibodies. Propidium iodide (0.5 µg/ml, BD Biosciences) was used to identify dead cells. Samples were analyzed on a FACSCalibur flow cytometer (Becton Dickinson) using CELLQUEST PRO software, collecting events of 20 seconds for each sample.

All animals were housed and maintained under pathogen-free conditions at the Rocky Mountain Laboratory animal facility.

M. Statistical Analysis

Unless noted otherwise, unpaired t-tests were used to calculate 2-tailed P values using Graph Pad Prism 4 software.

Example 3

Methods for FIGS. 5-10

This Example describes the methods used in generating the data shown in FIGS. 5-10.

A. Quantitative Reverse-Transcription (RT) Polymerase Chain Reaction (PCR)

Oligonucleotide primers and probes were designed with Primer Express software (version 2.0; Applied Biosystems) and synthesized by Applied Biosystems. The protocols were performed in triplicate, with 16S rRNA as a control.

B. Human Neutrophil Isolation

PMNs were isolated from venous blood of healthy volunteers in accordance with protocols approved by the Institutional Review Board for Human Subjects, NIAID, and the University of Tubingen, Germany.

C. Neutrophil Chemotaxis and Calcium Ion Fluxes

Neutrophils were subjected to a brief hypotonic shock with pyrogen-free water (Sigma), washed, and suspended at $5 \times 10^6$ cells/ml in HBSS containing 0.05% human serum albumin (HAS; CLB). Chemotaxis of neutrophils was determined by using fluorescently-labeled neutrophils that migrated through a membrane fitted into an insert of a 24-well microtiter plate transwell system (Costar) containing a prewetted 3-µm-pore-size polycarbonate filter. For measurement of calcium ion fluxes, $5 \times 10^6$ neutrophils/ml were loaded with 2 µM Fluo-3-AM (Molecular Probes) in RPMI containing 0.05% HSA (RPMI-HSA) for 20 minutes at room temperature under agitation, washed twice with buffer, and resuspended in RPMI-HSA at $10^6$ cells/ml. Calcium fluxes were analyzed with a FACSCalibur (Becton Dickinson).

D. Priming of Human Neutrophils

Priming of PMNs by synthetic PSMs was determined by increased surface expression of CD11b and gp91phox (granule exocytosis). PMNs were incubated with 10-10000 ng/ml PSM, 10 µM fMLP, 10 ng/ml lipopolysaccharide, or 10 µg/ml lipoteichoic acid in 96-well tissue culture plates at 37° C. with rotation for 60 minutes. The assay was terminated by centrifuging cells at 4° C. for 8 minutes at 350×g. Cells were washed twice in cold Dulbecco's phosphate-buffered saline and stained with and isotype control antibody (BD Biosciences) or those specific for CD11b (mAb 44, BD Biosciences) or gp91phox (mAb 7D5). Propidium iodide (0.5 µg/ml) was used to identify dead cells. PMNs were analyzed on a FACSCalibur flow cytometer (Becton Dickinson) and dead cells were excluded with a single gate. Percent positive neutrophils were determined with a marker defined by the boundary of the isotype-matched control antibody.

E. Lysis of Human Neutrophils

Lysis of PMNs by synthetic PSMs or clarified *S. aureus* culture media was determined essentially as described above in Example 2. Synthetic PSMs (1 or 10 µg/ml) were added to wells of a 96-well tissue culture plate containing $10^6$ PMNs and plates were incubated at 37° C. for up to 3 hours. At the desired times, PMN lysis was determined by release of lactate dehydrogenase (LDH; Cytotoxicity Detection Kit, Roche Applied Sciences). Alternatively, wild-type and isogenic mutant *S. aureus* strains were cultured for 18 hours at 37° C. in 50 ml TSB with shaking using a 100 ml flask. Bacteria were removed by centrifugation and culture media were sterilized by filtration and stored at −80° C. in aliquots until used. Culture medium was diluted 1:10 in RPMI/H, mixed with human PMNs ($10^6$) and tested for its ability to cause PMN lysis.

F. Measurement of Cytokine Production

After isolation and washing, PMN or PBMC were resuspended in RPMI 1640 medium (Sigma) supplemented with 10% human serum, 2 mM L-glutamine, 100 U/ml penicillin, 100 µg/ml streptomycin, 2 mM sodium pyruvate, and 10 mM HEPES. Cells were distributed to a 96-well culture plate at 200 µl and $5 \times 10^5$ cells per well. Synthetic PSM peptides or filtered bacterial culture supernatants were diluted in fresh culture medium and added to the plate at 100 µl/well. Plates were incubated at 37° C. in a 5.5% $CO_2$ incubator for 5 hours. Then, the plate was centrifuged at 1500 rpm for 10 minutes, and supernatant was harvested from each well. Mono Mac 6 cells were obtained from DSMZ (Germany), and were grown in RPMI 1640 plus 10% heat inactivated fetal bovine serum (HyClone), 2 mM L-glutamine, 10.0 units/ml penicillin, 10.0 µg/ml streptomycin, 0.2× non-essential amino acid solution, and OPI medium supplement (Sigma). Cells were grown in T75 culture flasks in a 37° C. $CO_2$ incubator and harvested by centrifugation. After removal of supernatant, cells were resuspended in fresh culture medium, counted, and distributed into a 96-well cell culture plate at 100 µl and $2.5 \times 10^5$ cells per well. Phorbol 12-myristate 13-acetate (Sigma) was added to a final concentration of 2.5 ng/ml for cell pre-stimulation. The plate was incubated in a 37° C. $CO_2$ incubator for 3 hours. At the end of the pre-stimulation period, synthetic PSM peptides were diluted in culture medium and added to the cells at 100 µl/well. Cells were incubated in a 37° C. $CO_2$ incubator for 20-22 hours, and the plate was centrifuged at 1500 rpm for 10 minutes. Human TNF-α, IL-1β, IL-8, and mouse TNF-α were measured in the culture supernatants with commercial ELISA assay kits (R&D systems) according to the manufacturer's instructions.

G. Circular Dichroism (CD) Measurement

The structures of synthetic PSM peptides were analyzed by CD spectroscopy on a Jasco spectropolarimeter model J-720 instrument. Solutions of PSM peptides, each at 1.0 mg/ml, were prepared in 50% trifluoroethanol. Measurements were performed in triplicate and the resulting scans were averaged, smoothed, and the buffer signal was subtracted.

H. Scanning Electron Microscopy

For scanning electron microscopy, PMNs were fixed, washed, and mounted on stubs as described above in Example 2. After mounting on stubs, samples were coated lightly with chromium using an ion beam sputterer (South Bay Technology, Inc.), and examined with a Hitachi S5200 field emission scanning electron microscope (Hitachi High Technologies America). Digital images were collected and adjusted for brightness and contrast with Photoshop CS (Adobe Systems).

I. Statistical Analysis

Unless noted otherwise, unpaired t-tests were used to calculate 2-tailed P values using Graph Pad Prism 4 software.

Example 4

Administration of PSM Peptides to a Human Subject

This Example demonstrates a method of administering a PSM peptide to a subject, for example, for the treatment, amelioration, or prevention of methicillin-resistant *staphylococcus* (for instance MRSA (such as CA-MRSA) or MRSE) in the subject. A suitable subject for receiving the PSM peptide vaccine is one who is at risk for exposure to methicillin-resistant bacteria, for instance a subject who deals closely with the public or who lives in close quarters with other people, such as a nursing home or other long-term care facility, particularly if the individuals residing there having chronic illnesses or impaired immunity, or a subject with an indwelling medical device.

The PSM peptide vaccine is, in one example, PSMα3 provided as a pharmaceutical composition, and is administered subcutaneously in a dose that includes about 0.1 μg to 10 mg of immunogenic PSMα peptide. A second dose is administered in the same fashion approximately three days to three months after the first dose, and the efficacy of protection against MRSA infection is assessed by measuring antibody titers using standard laboratory protocols.

The PSM peptide vaccine is, in another example, PSM-mec provided as a pharmaceutical composition, and is administered subcutaneously in a dose that includes about 0.1 μg to 10 mg of immunogenic PSM-mec peptide. A second dose is administered in the same fashion approximately three days to three months after the first dose, and the efficacy of protection against methicillin-resistant *staphylococcus* infection is assessed by measuring antibody titers using standard laboratory protocols.

Example 5

Immunization with Synthetic PSM Peptides Triggered Specific Antibody Productions In Vivo This Example demonstrates the immunogenicity of specific synthetic PSM peptides. In order to determine the immunogenicity of synthetic PSM peptides, mice (BALB/c, female, 6-8 weeks) were injected subcutaneously with 50 μg (100 μL) of each PSM peptide in sterile PBS emulsified with complete Freund's adjuvant (CFA) for primary immunization. A booster injection containing incomplete Freund's adjuvant (IFA) instead of CFA was given to the animals 14 days after the primary immunization. The control group of animals received injections of sterile PBS and adjuvants only. Three blood withdrawals were performed on each mouse. The first two blood samples were collected via retro-orbital route immediately before primary injection and before booster injection, respectively. All animals were sacrificed 21 days after booster injection for the terminal blood samples.

PSM-specific antibodies in mouse serum were determined by ELISA assays. Microtiter plates (Nunc 96-well flat-bottom MaxiSorp plates) were coated with 20 μg/ml of each synthetic PSM peptides in PBS plus 0.05% NaN$_3$, and incubated overnight at 4° C. The plates were washed with PBS containing 0.05% Tween-20, and blocked for 1 hour at room temperature with 1% BSA (Sigma) and 0.05% NaN$_3$ in PBS. Serum samples were diluted in assay diluent (Tris-buffered saline containing 0.1% BSA and 0.05% Tween-20, pH 7.2), and added to the washed wells at 100 μl/well for an incubation of 2 hours at room temperature. Plates were washed again and HRP-labeled goat anti-mouse IgG (R&D Systems) and goat anti-mouse IgM (Jackson ImmunoResearch Laboratory) were diluted in assay diluent and added to the plates at 100 μl/well for an incubation of 1 hour at room temperature in order to detect PSM specific mouse IgG and IgM, respectively. Plates were washed again and a substrate solution containing equal volume of Tetramethylbenzidine and H$_2$O$_2$ was added to the plates at 100 μl/well for color development. The reaction was terminated by adding 50 μl of 1 M H$_2$SO$_4$ to each well, and optical density (O.D.) was measured at 450 nm using an ELISA plate reader.

Figure 12:
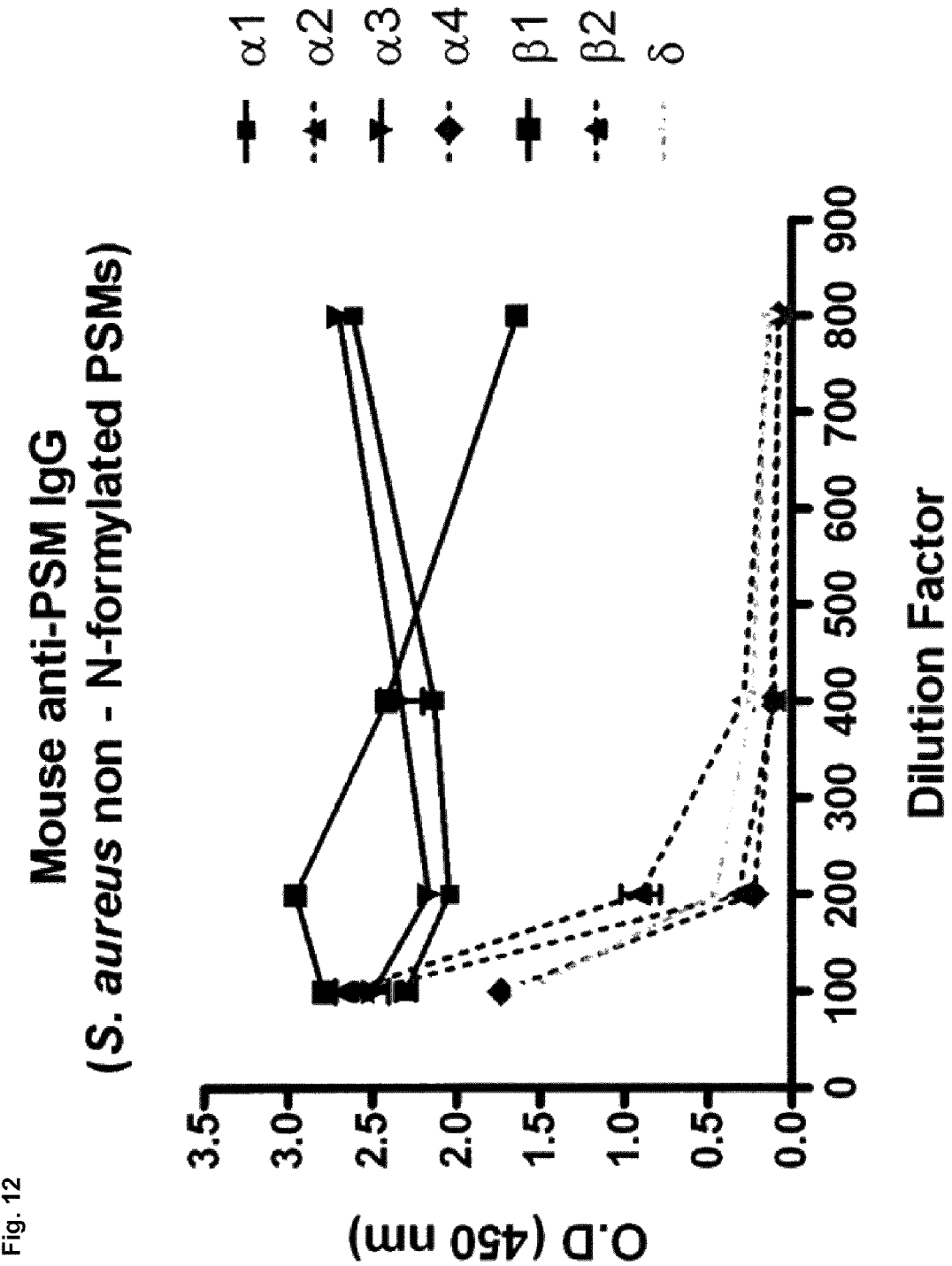
FIG. 12 is a graph showing that immunization with non-N-formylated synthetic PSM peptides triggers antibody production in vivo.

As shown in FIGS. 11 and 12, all of the synthetic PSM peptides were immunogenic, triggering specific antibody productions in vivo. As shown in FIG. 11, of the N-formylated peptides, PSMα1, PSMα3, and PSMα4 generated the most robust antibody production. FIG. 12 shows that, of the non N-formylated PSM peptides, PSMα1, PSMα3, and PSMβ1 generated the strongest response.

Example 6

Neutralizing Effect of PSM-Specific Antiserum on Cytokine Production from Human PMNs Challenged with Bacterial Culture Supernatants This Example demonstrates the neutralizing effect of PSM-specific antiserum on cytokine production from human PMNs challenged with bacterial culture supernatants. For measurement of the neutralizing activity of PSM-specific antisera described above (see Example 5) against cytokine production from human PMNs challenged with bacterial supernatants in vitro, bacterial overnight culture supernatants (strains MW2 and LAC) were pre-incubated with 50% PSM-specific mouse antiserum or control serum at 37° C. for 2 hours with gentle rotation in a 5.5% CO$_2$ incubator.

Human PMNs were isolated from venous blood of healthy volunteers. After isolation and washing, PMNs were resuspended in RPMI 1640 medium (Sigma) supplemented with 10% human serum, 2 mM L-glutamine, 100 U/ml penicillin, 100 μg/ml streptomycin, 2 mM sodium pyruvate, and 10 mM HEPES. Cells were distributed to a 96-well cell culture plate (Costar) at 200 μl and 1×10$^6$ cells per well. Antiserum-pretreated bacterial culture supernatants were diluted in fresh cell culture medium and added to the plate at 100 μl/well to reach a final dilution factor of 1:100. Plates were incubated at 37° C. in a 5.5% CO$_2$ incubator for 5 hours. The plates were then centrifuged at 1500 rpm for 10 min, and supernatants were harvested from each well.

Human IL-8 in the culture supernatant was measured with commercial ELISA assay kits (R&D Systems) according to the manufacturer's instructions. Results were expressed as mean±SEM, and an unpaired two-tailed t-test was applied to determine the significance of the differences in IL-8 production between PSM antiserum pretreated and control serum treated groups.

Figure 13:
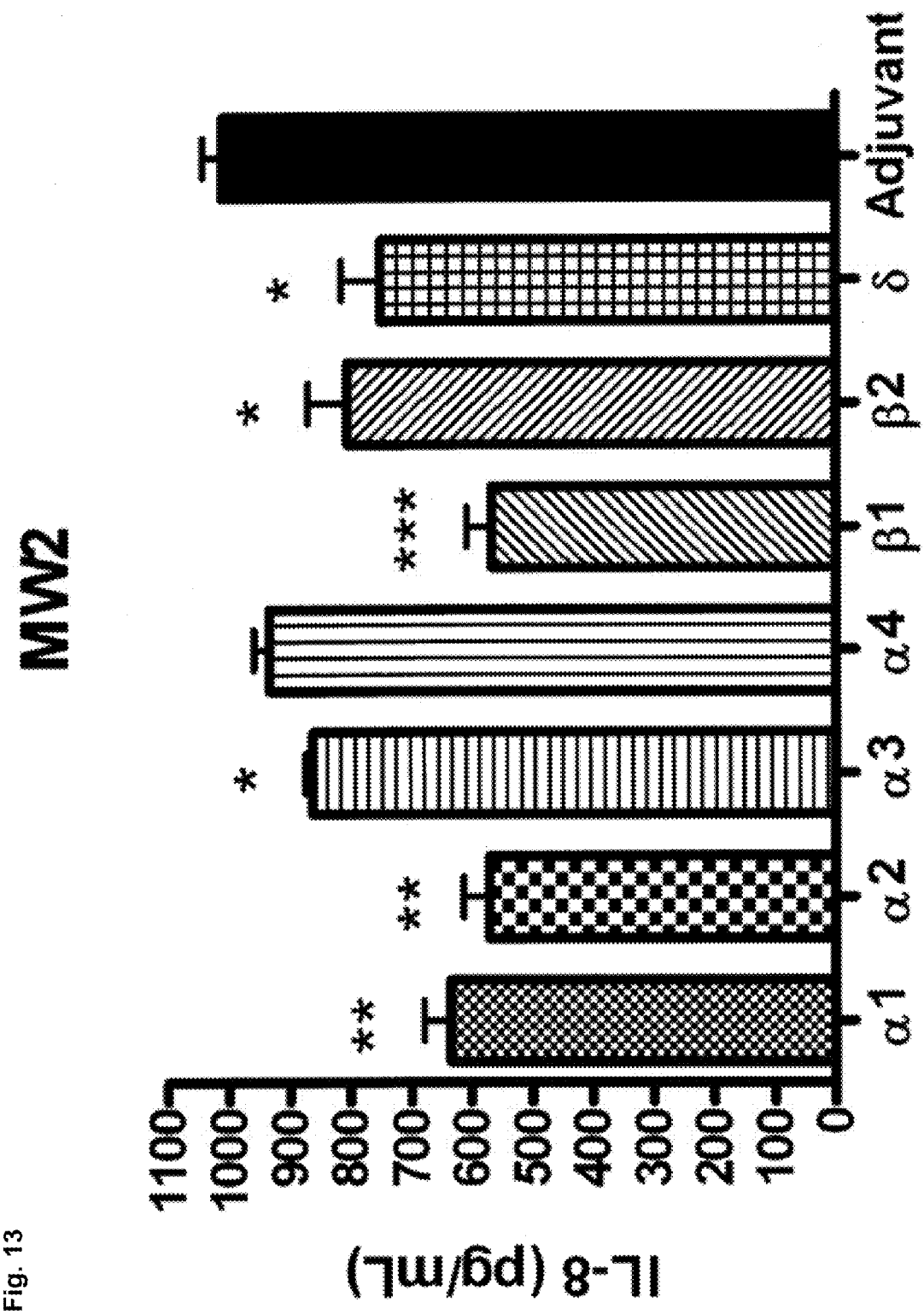
FIG. 13 is a graph showing the neutralizing effect of PSM-specific antiserum on cytokine production from human PMNs challenged with MW2 bacterial culture supernatants.
Figure 14:
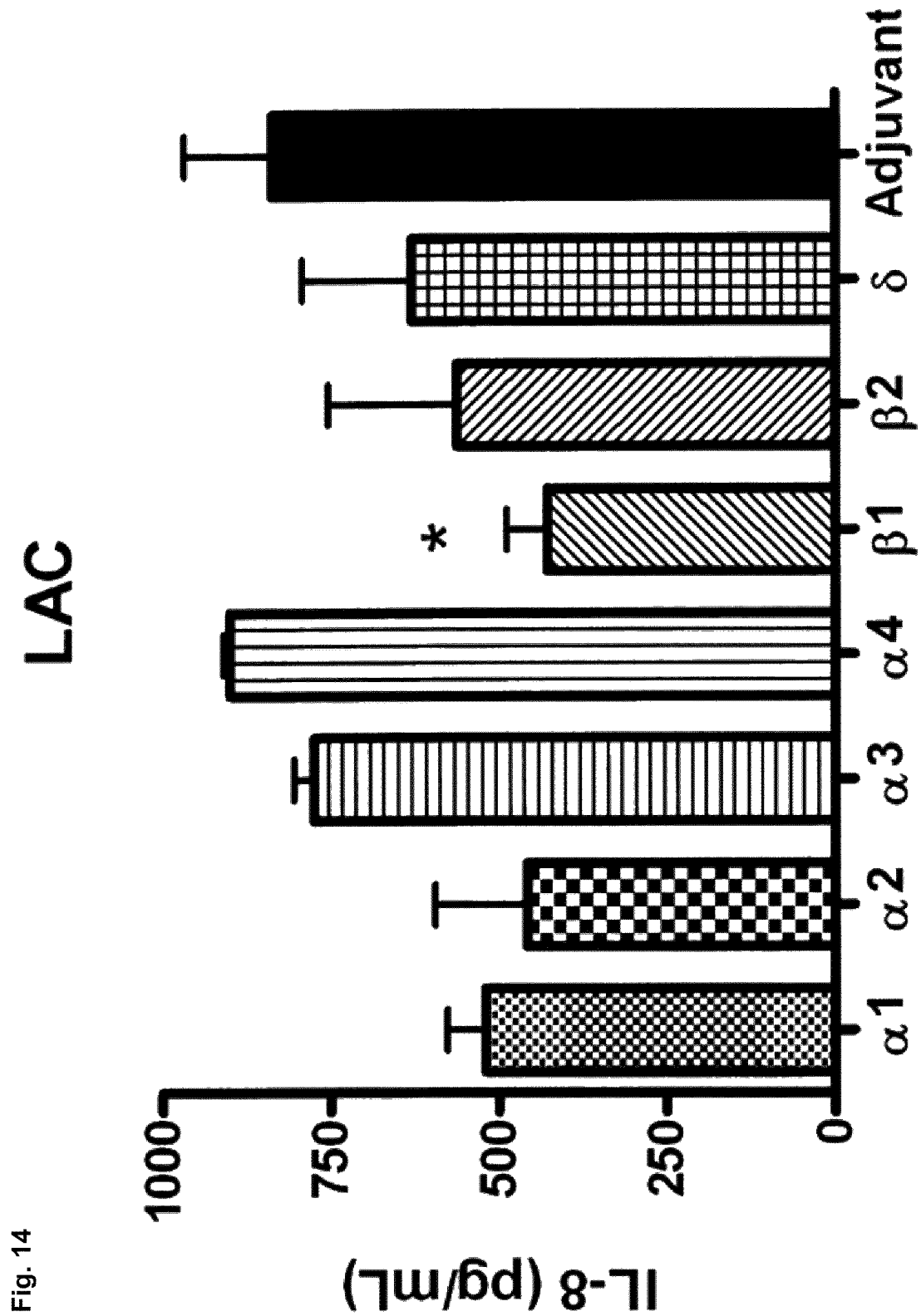
FIG. 14 is a graph showing the neutralizing effect of PSM-specific antiserum on cytokine production from human PMNs challenged with LAC bacterial culture supernatants.

As shown in FIG. 13 (MW2) and FIG. 14 (LAC), PSM-specific antiserum significantly inhibited IL-8 production from human PMNs challenged with community-acquired *S. aureus* culture supernatants.

Example 7

PSM-Specific Antiserum Mediated Opsonophagocytosis and Killing of *S. aureus* by Human PMNs This Example demonstrates that PSM-specific antiserum mediated opsonophagocytosis and killing of *S. aureus* by human PMNs. In order to demonstrate that PSM-specific antisera mediates phagocytosis and killing of S. aureus in vitro, human PMNs were isolated from venous blood of healthy volunteers. After isolation and washing, PMNs were resuspended in Dulbecco's PBS containing 10 mM d-glucose (DPBS/G) and kept on ice. Cell concentration was adjusted to $1\times10^7$ cells/ml.

S. aureus strains MW2, LAC, and 252 were grown to late exponential phase in TSB medium. Bacterial cells ($5\times10^7$ cells/25 µl/sample) were opsonized with 50% PSM-specific mouse antiserum or adjuvant control serum (25 µl/sample) for 30 minutes at 37° C. with gentle rotation. Phagocytosis was then performed by mixing $5\times10^6$ opsonized bacterial cells (5 µl) with $10^6$ freshly isolated human PMNs (100 µl), and gently rotating the mixture for 30 minutes at 37° C. in a 5.5% $CO_2$ incubator. At the end of the incubation period, phagocytosis was terminated by transferring all samples onto ice.

Samples were diluted in TSB medium and plated 100 µl per TSB plate without antibiotics. Phagocytosis activity was determined and compared among groups by number of viable bacterial colonies on the plates. Results were expressed as mean±SEM, and an unpaired two-tailed t-test was applied to determine the significance of the differences in viable bacterial colony number among bacterial groups opsonized with PSM-specific antiserum or control serum.

Figure 15:
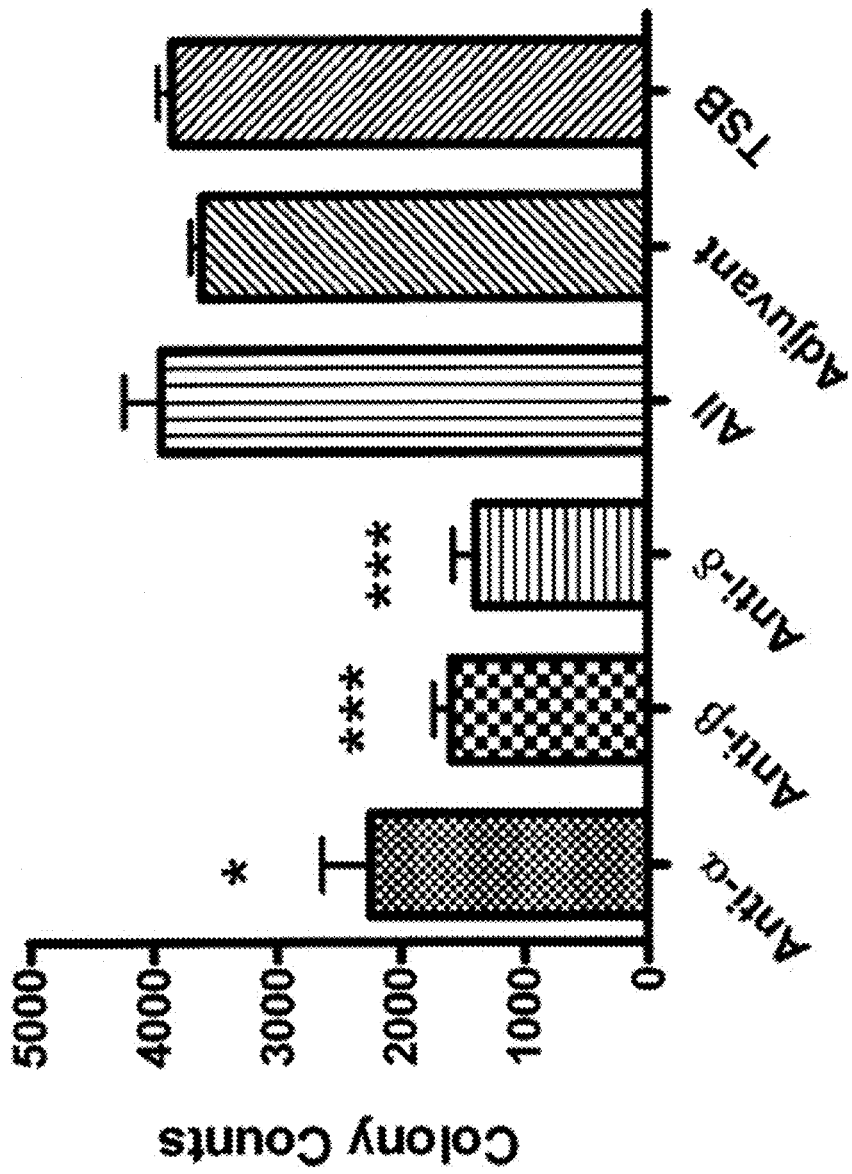
FIG. 15 is a graph showing that anti PSM-α-, -β-, and δ-toxin specific antisera mediated opsonophagocytosis and killing of *S. aureus* (MW2) by human PMNs.
Figure 16:
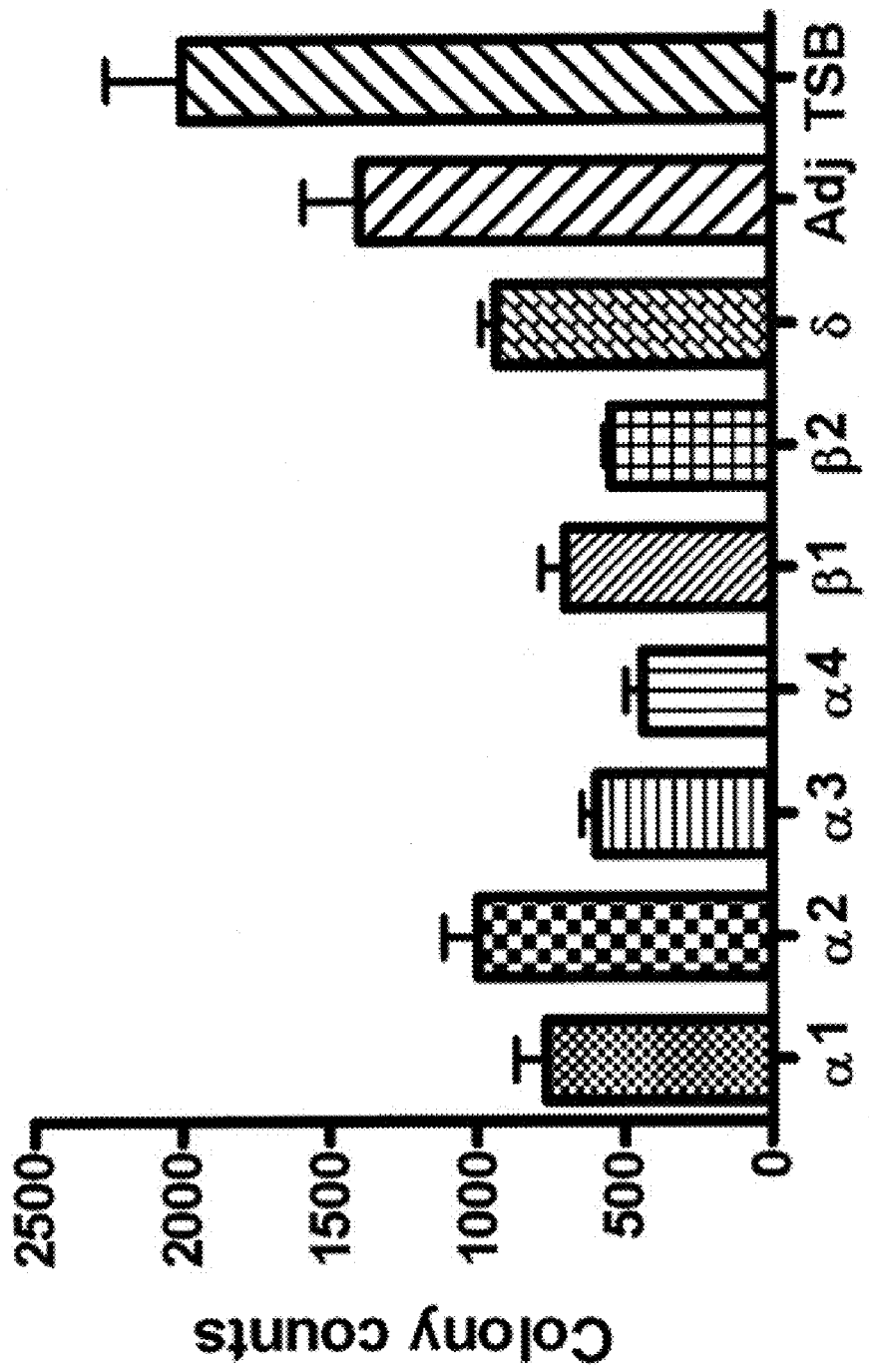
FIG. 16 is a graph showing that anti PSM-α1-, α2-, α3-, β1-, β2-, and δ-toxin specific antisera mediated opsonophagocytosis and killing of *S. aureus* (MW2) by human PMNs.

As shown in FIGS. 15 and 16 (MW2) and FIG. 17 (LAC), viable colony number was significantly reduced from PSM specific antiserum pre-opsonized bacterial groups, indicating that PSM antiserum mediated phagocytosis in vitro by efficiently opsonizing bacterial cells. In FIGS. 15 and 17, although it appears that a combination of all of the PSMs was not effective (see the columns labeled "All"), this is an artifact that resulted from the dilution of the most effective PSMs by the less effective PSMs.

Example 8

PSM-mec Peptide as Vaccine Target Against Methicillin-Resistant *Staphylococcus*

Methods

Strains and growth conditions: S. aureus and S. epidermidis genome sequencing strains (S. epidermidis RP62A and ATCC12228, S. aureus COL, Sanger 252, Sanger 476, N315, Mu50, USA300, and MW2) were acquired from the Network on Antimicrobial Resistance in S. aureus (NARSA). Other methicillin-resistant S. epidermidis (MRSE) and methicillin-sensitive S. epidermidis (MSSE) strains were from Shanghai (~100 strains), Paris (~70), and Norway (~100), and other S. aureus strains were from a San Francisco strain collection (~80, all MRSA) in addition to those published by Fitzgerald et al. (~35, MRSA and MSSA) (Diep et al, J. Infect. Dis. 193:1495-1503, 2006; Pan et al., J. Infect. Dis. 192:811-8181, 2005; Fitzgerald et al., Proc. Natl. Acad. Sci. USA 98:8821-8826, 2001). All strains were grown in tryptic soy broth (TSB). When necessary during cloning of the allelic replacement plasmid, antibiotics were added at appropriate concentrations (ampicillin at 100 mg/ml for cloning in E. coli; chloramphenicol at 10 mg/ml for staphylococci). For strains for which information on methicillin resistance was not available from the literature, methicillin resistance was determined by plating on TSB agar containing 6 mg/ml oxacillin Deletion of psm-mec: Allelic replacement of the psm-mec gene was performed using the procedure described by Bae and Schneewind (*Plasmid* 55:58-63, 2006), which allows for gene deletion without replacement by an antibiotic resistance cassette. Using this procedure, the psm-mec gene was deleted in its entirety. Briefly, two PCR fragments up- and downstream of psm-mec, introducing att1 and att2 recombination sites at the distal ends and an EcoRI site at the psm-mec ends were amplified from genomic DNA of S. aureus Sanger 252. Oligonucleotides used were PSMErev1 (CAAGACTTG-CATTCAGGCTTTCGGTGAATTCTTTC; SEQ ID NO: 10), PSMEatt1 (GGGGACAAGTTTGTACAAAAAAG-CAGGCTGG AAGTTTTGTGCTTTATAATGAACGG-GAGCAAGC; SEQ ID NO: 11), PSMErev2 (CACCAGT-GAATTCCATATGCATACCCTCTTTC; SEQ ID NO: 12), and PSMEatt2 (GGGGACCACTTTGTACAA-GAAAGCTGGGTGTACCACCTAG CAAAGTTG-CAAATTTGAC; SEQ ID NO: 13).

After digestion with EcoRI and ligation, the resulting fragment with flanking att1 and att2 sites was cloned into plasmid pKOR1 using att recombination and a Clonase kit (Invitrogen). The resulting plasmid was electroporated in S. aureus RN4220, isolated from this strain and electroporated in the target strain. Afterwards, the allelic recombination procedure was performed. Fidelity of gene deletion was determined by analytical PCR and RP-HPLC/ESI-MS. The PSM production phenotype of all deletion and wild-type strains was verified regularly and in all precultures grown for key experiments using RP-HPLC/ESI-MS.

SCCmec typing: Typing of S. epidermidis and S. aureus SCCmec was performed using the method by Kondo et al. (Antimicrob. Agents Chemother. 51:264-274, 2007).

Peptide synthesis: Peptides were synthesized with an N-terminal formyl methionine residue in each peptide. Peptide sequence fidelity was determined by the Peptide Synthesis Unit of the NIAID. The structures of synthetic PSM peptides were analyzed by CD spectroscopy as described in Example 2.

Chromatography/mass spectrometry: RP-HPLC/ESI-MS was performed on an Agilent 1100 chromatography system coupled to a Trap SL mass spectrometer using a Zorbax SB-C8 2.3×30 mm column essentially as described in Example 2. Quantification was performed by integration of the UV spectra, if peaks were well separated. Alternatively, quantification was based on extracted ion chromatograms using the most abundant peaks of the electrospray ion mass spectra of the respective PSM peptides, with calibration using synthetic peptides. SEC/ESI-MS was performed using the same equipment as RP-HPLC/ESI-MS with a Superdex Peptide HR 10/30 column (GE Healthcare) applying an isocratic gradient of 0.1% trifluoroacetic acid in 30% acetonitrile at 0.5 ml/min PSM-mec purification and N-terminal sequencing: PSM-mec was purified from S. epidermidis RP62A stationary phase culture using the same procedure as used previously for the large-scale isolation of other PSMs (Yao et al., J. Infect. Dis. 191:289-298, 2005). Briefly, supernatant was precipitated using 10% ice-cold trichloroacetic acid. The pellet was dissolved in 100 mM Tris buffer pH 8.0 and taken to neutral pH with 6 N NaOH. Then, a two-step reversed-phase chromatography protocol was used for purification as described (Yao et al., J. Infect. Dis. 191:289-298, 2005). For N-terminal sequencing at the Peptide Sequencing Unit of the NIAID, the N-terminal formyl group was removed by heating for 2 h at 55° C.

Biofilm assays Semi-quantitative biofilm assays were performed using polystyrene microtiter plates and safranin staining. To assess the impact of PSM-mec on biofilm formation, the peptide was added at the time of inoculation with the indicator strain SA113 from pre-cultures (1:100) at different concentrations. For pre-coating with fibrinogen, a 25 mg/l fibrinogen solution in phosphate-buffered saline (PBS) was filter-sterilized and 100 ml solution was pipetted in each well.

After 18 h at 4° C., wells were washed twice with PBS, blocked with 2% sterile bovine serum albumin (BSA) solution for 2 h at 37° C., and washed 4 times with PBS. Then the biofilm assay was performed as described (Vuong et al., *J. Infect. Dis.* 188:706-718, 2003).

Human neutrophil assays: Human neutrophil isolation, chemotaxis, calcium ion flux, priming, lysis assays, and measurement of IL-8 production were performed as described in Example 2.

Hemolysis: Hemolytic activity of PSM peptides was determined by incubating samples with a 2% (v/v) sheep red blood cells and incubation for 1 h at 37° C. as described (Wang et al., *Nature Med.* 13:1510-1514, 2007). Hemolytic activity of *S. aureus* wild-type and psm-mec deletion strains was assessed by streaking on sheep blood agar plates.

Mouse bacteremia and skin abscess models: Mouse bacteremia and skin abcess experiments were performed as described in Example 2.

Statistics: Statistical analysis was performed using Student's t-tests for 2, or 1-way-ANOVA with Bonferroni post-tests for more than 2 groups, and Graph Pad Prism version 5 software.

Results

Identification of the SCCmec-Encoded PSM-mec

Figure 18A:
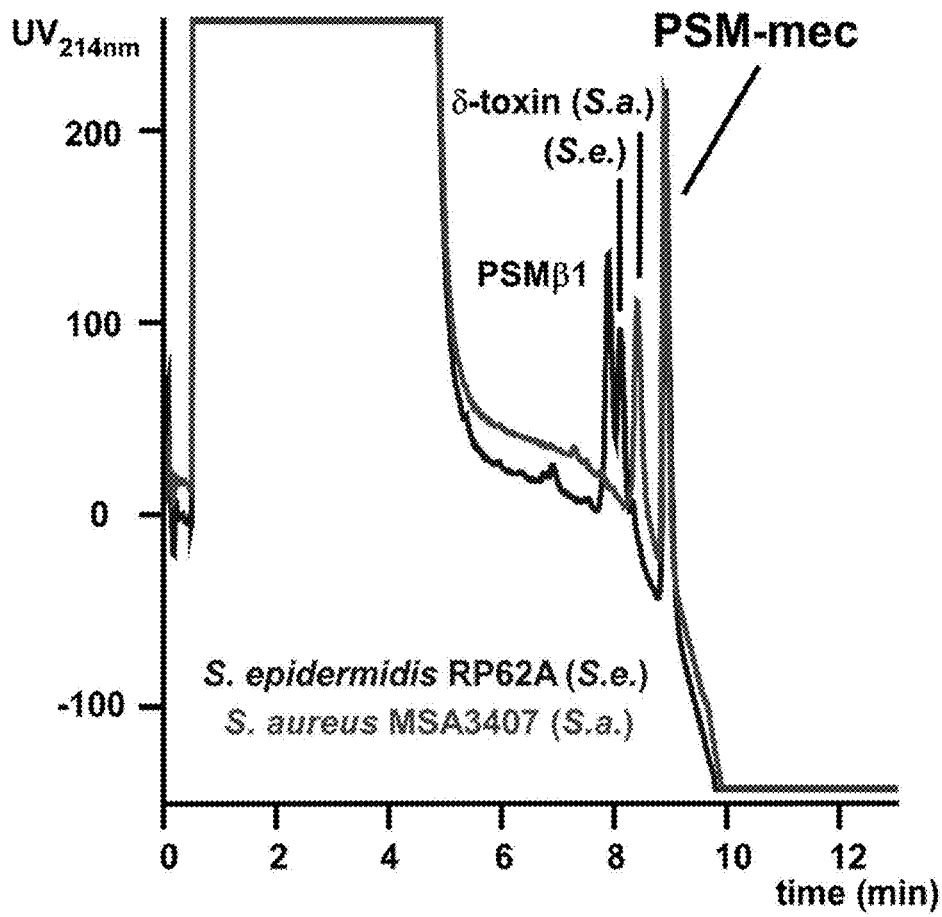
FIG. 18A is an RP-HPLC elution profile of *S. aureus* MSA3407 and *S. epidermidis* RP62A filtrates at 8 hours of growth. Peaks of major PSM peptides and the newly identified PSM-mec are indicated.
Figure 18B:
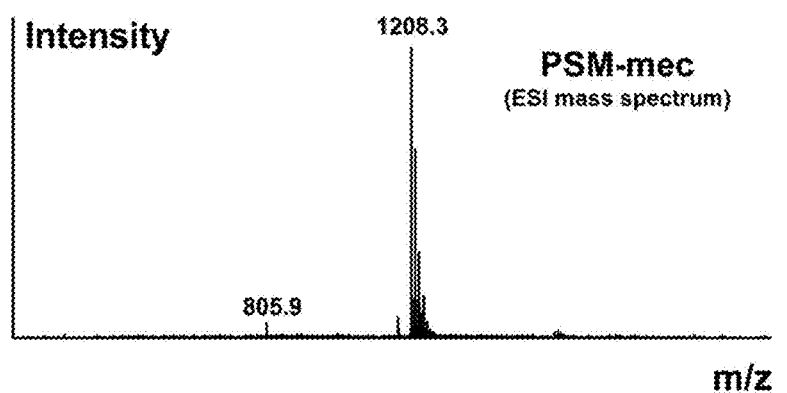
FIG. 18B is an ESI chromatogram of the PSM-mec peak obtained by RP-HPLC/ESI-MS from *S. epidermidis* RP62A. The respective PSM-mec ESI chromatogram of *S. aureus* MSA3407 or any strain with PSM-mec production showed the same m/z peaks. The series of peaks with slightly higher masses close to m/z 1208.3 are due to water and sodium adducts.

A collection representing a wide variety of *S. aureus* strains, which contained 34 strains, 11 of which were MRSA, 79 MRSA strains of pulsed-field types USA100, USA200, USA300, USA500, USA1000, and USA1100 from infection and carriage isolates from San Francisco, 54 infectious *S. epidermidis* strains from Paris, 56% of which were MRSE, and 180 *S. epidermidis* strains from Norway, 29% of which were MRSE was analyzed by RP-HPLC/MS. An *S. epidermidis* strain collection from Shanghai that included 51 colonizing strains (no MRSE) and 41 isolates from infection (29% MRSE) was also analyzed. Ten percent of all analyzed MRSA strains and 68% of all analyzed MRSE strains produced an additional peptide peak in the RP-HPLC profile within the elution range characteristic for PSMs (shown for one *S. epidermidis* and one *S. aureus* strain in FIG. 18A). The molecular weight of the peptide, 2414.6 Da (FIG. 18B), as calculated from the electrospray ionization (ESI) mass spectrum obtained by RP-HPLC/ESI-MS, was the same in all these strains. The peptide was never detected in methicillin-sensitive *S. aureus* (MSSA) or *S. epidermidis* (MSSE). In the Shanghai collection, all PSM-mec producing *S. epidermidis* strains were isolated from human infections, whereas the MSSE skin isolates (colonizers) never produced the peptide. In the San Francisco strain collection, the peptide was found in 5 of 14 infectious USA100 and USA200 isolates, but never in other pulsed-field types. These results indicated that peptide production is linked to specific SCCmec elements.

The peptide was purified and the N-terminal sequence was determined, which allowed identification of the peptide-encoding gene. Analysis of published staphylococcal genome sequences revealed presence of the gene in the type II SCCmec clusters of *S. epidermidis* strain RP62A (Gill et al., *J. Bacteriol.* 187:2426-2438, 2005), and *S. aureus* strains Mu50, N315 and Sanger 252 (Holden et al., *Proc. Natl. Acad. Sci. USA* 101:9786-9791, 2004; Kuroda et al., Lancet 357: 1225-1240, 2001). In addition, a tblastn search showed that the gene was present within SCCmec clusters of types II or III in a series of staphylococcal strains including strains of *S. aureus, S. epidermidis, S. saprophyticus, S. pseudintermedius*, and *S. sciuri*. Furthermore, the analyzed MRSE producers from the Paris and Shanghai collections were typed as predominantly of SCCmec type III and the four MRSA producers from the Fitzgerald et al. collection were typed as SCCmec type II. Finally, the gene was also detected in MRSA strains from Canada and New York City (strains C10682 and BK20781, GenBank FJ390057 and FJ670542.1, respectively) that contained the novel SCCmec type VIII, which appears to have arisen from recombination between different SCCmec elements (Zhang et al., Antimicrob. Agents Chemother. 53:531-540, 2009). These results indicated that the gene is typically encoded in SCCmec elements, specifically in the J1 region that is common to SCCmec types II and III. Thus, the novel PSM peptide was designated as PSM-mec owing to the fact that it is encoded within SCCmec clusters. Presence of the gene in SCCmec types II and III is in accordance with the data obtained with different MRSA pulsed field types, particularly the absence from community-associated MRSA of pulsed-field type USA300, which contain SCCmec type IV (Diep et al., *Lancet* 367:731-739, 2006).

Figure 19B:
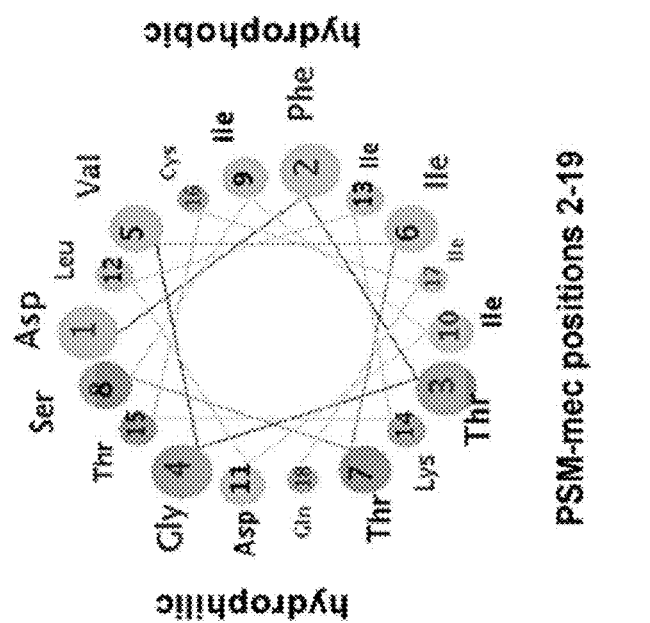
FIG. 19B is an α-helical wheel showing the amphipathy of PSM-mec.
Figure 19A:
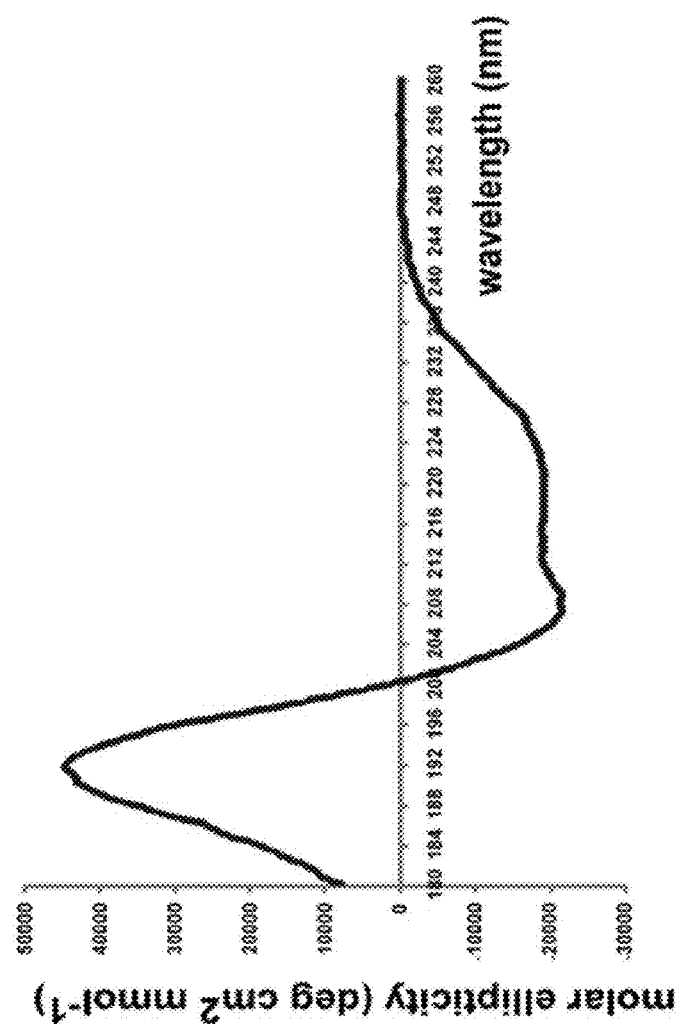
FIG. 19A is a graph showing the CD spectrum of PSM-mec. Computation of α-helical content gave the following results: 59.3% (CONTINLL), 56.2% (SELCON3), 63.7% (CDSSTR).

The psm-mec gene contained only the DNA sequence encoding the final peptide product and no signal peptide. In addition, comparison of the theoretical mass of the translation product (2386.8 Da) with the detected mass of the secreted peptide indicated formylation of the N-terminal methionine (mass difference of 28 Da), which is common in bacterial proteins and found in all PSMs. Analysis of secondary structure by circular dichroism (CD) (FIG. 19A) and arrangement of the peptide sequence in an α-helical wheel (FIG. 19B) revealed strong α-helicity and amphipathy, confirming that PSM-mec had characteristics typical of PSM peptides.

Characteristics of PSM-mec Production

Figure 20A:
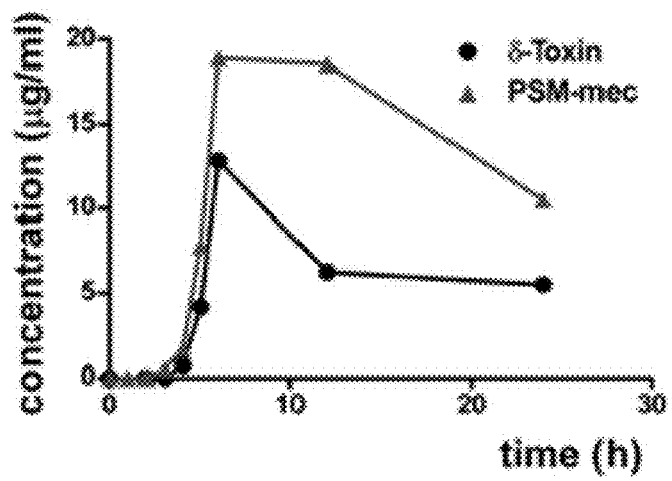
FIG. 20A is a graph showing production of δ-toxin and PSM-mec during growth of *S. aureus* in shaken culture.
Figure 20B:
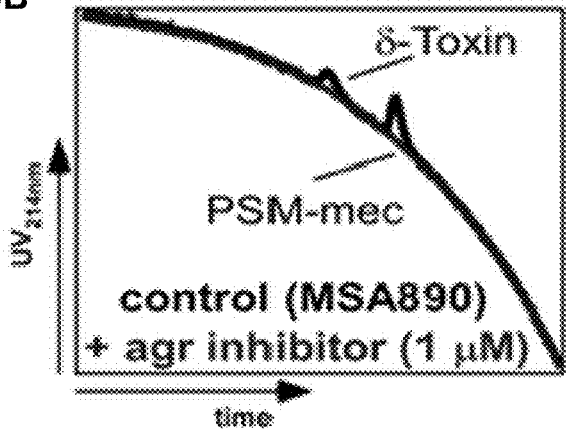
FIG. 20B is a graph showing PSM production in strain *S. aureus* MSA890 with and without addition of agr-inhibiting *S. epidermidis* autoinducing peptide. With addition of inhibitor, no PSMs were detectable.

All known PSM peptides are under control of the agr quorum-sensing system. Growth phase-dependent production of PSM-mec followed the same pattern as observed for other PSMs (FIG. 20A), suggesting quorum-sensing control. Furthermore, the agr-dysfunctional MRSA strains N315 and Mu50 have all psm genes including psm-mec (Kuroda et al., *Lancet* 357:1225-1240, 2001), but do not produce the corresponding gene products. Moreover, PSM-mec was never detected in strains without δ-toxin production, which is indicative of a defective agr system. These observations suggested that PSM-mec production is dependent on agr. To further evaluate this hypothesis, cross-inhibiting *S. epidermidis* autoinducing peptide, an efficient and specific inhibitor of *S. aureus* agr, was applied to cultures of PSM-mec-producing *S. aureus*. This led to complete absence of all PSMs, including PSM-mec (FIG. 20B). Thus, PSM-mec production is under control by the quorum-sensing system agr like other PSMs.

Figure 20C:
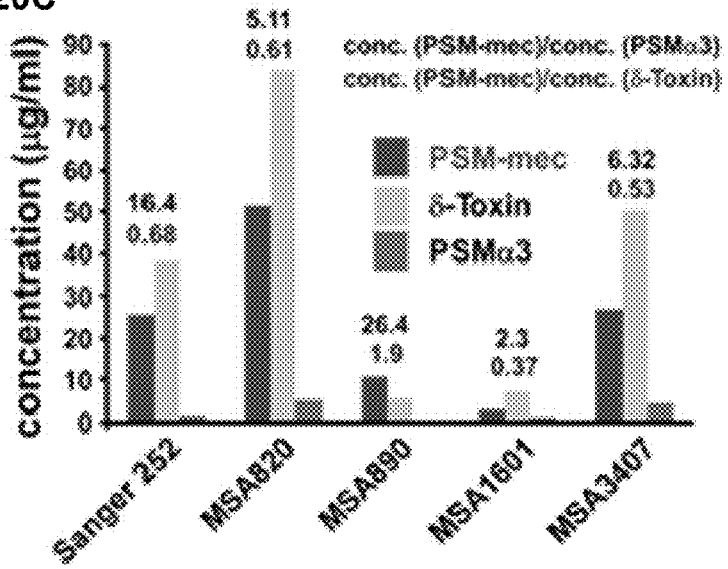
FIG. 20C is a graph showing production of selected PSMs at 8 hours of growth in the PSM-mec producing *S. aureus* Sanger 252 and other MRSA strains.

In many strains, PSM-mec was produced at high levels, approximately achieving, or in one strain exceeding, production levels of the otherwise most abundant PSM, δ-toxin (PSMγ) (FIG. 20C). Furthermore, while PSM-mec production was usually correlated with that of other PSMs, some strains showed a different production pattern. Strain MSA890 for example had high relative production of PSM-mec compared to other PSMs (FIG. 20C). Thus, the fact that PSM-mec production was not always entirely correlated with that of δ-toxin indicated regulatory influences in addition to agr, as previously shown for other PSMs.

Role of PSM-mec in Inflammation and Immune Evasion

Figure 21A:
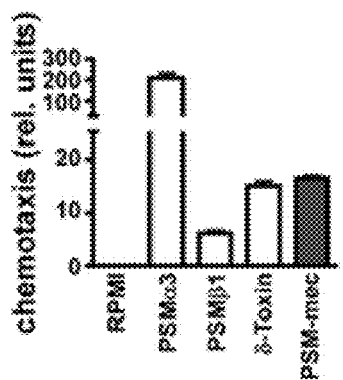
FIG. 21A is a graph showing chemotaxis of human neutrophils. Peptides were applied at 0.5 µg/ml (PSMα3), 2 µg/ml (δ-toxin), 5 µg/ml (PSM-mec), and 10 µg/ml (PSMβ1). Values were corrected for the different concentrations applied.
Figure 21B:
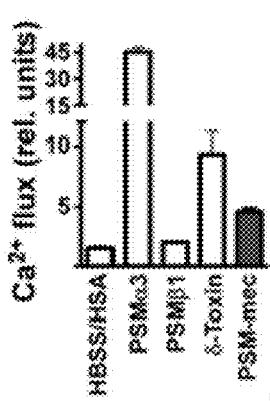
FIG. 21B is a graph showing calcium flux in human neutrophils. Peptides were applied at 0.1 µg/ml (PSMα3), 1 µg/ml (δ-toxin, PSM-mec), and 2.5 µg/ml (PSMβ1). Values were corrected for the different concentrations applied.
Figure 21C:
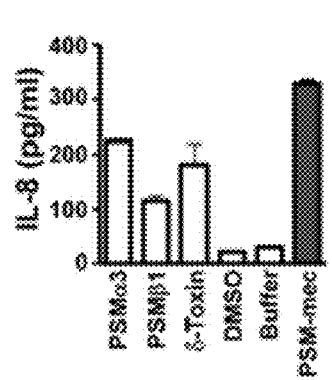
FIG. 21C is a graph showing secretion of the cytokine IL-8 at 10 µg/ml PSM.
Figure 21D:
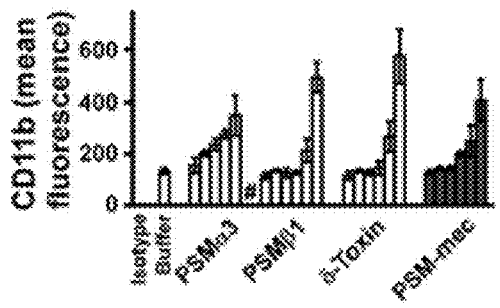
FIG. 21D is a graph showing surface expression of CD11b on human neutrophils. #, lysis of neutrophils occurred. For PSMs, bars represent values obtained from increasing concentrations of peptide: 10, 100, 200, 400, 1000, 10,000 ng/ml, from left to right in each group.
Figure 21E:
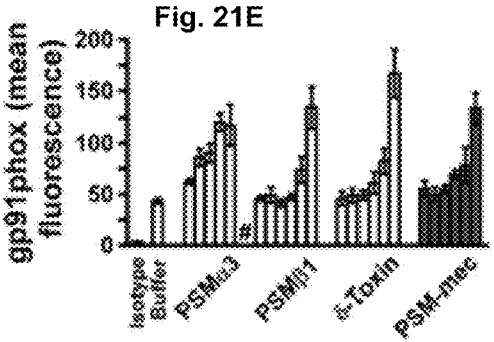
FIG. 21E is a graph showing surface expression of gp91phox on human neutrophils. #, lysis of neutrophils occurred. For PSMs, bars represent values obtained from increasing concentrations of peptide: 10, 100, 200, 400, 1000, 10,000 ng/ml, from left to right in each group.
Figure 21F:
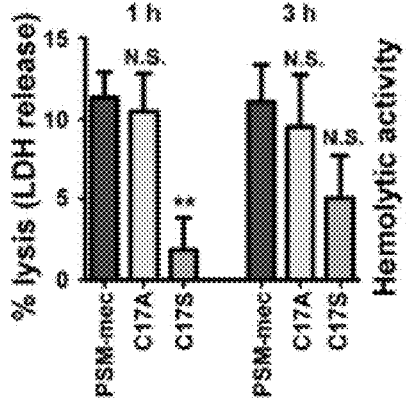
FIG. 21F is a graph showing neutrophil lysis at 50 µg/ml PSM, comparison of PSM-mec with C17A and C17S replacement peptides. Statistical comparisons are vs. PSM-mec. **, $p<0.01$; N.S., not significant.
Figure 21G:
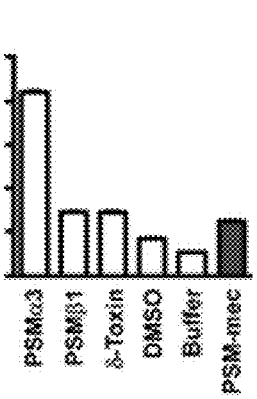
FIG. 21G is a graph showing hemolytic activity of PSM peptides applied at 10 µg/ml.

PSM peptides, particularly those of the α-type, cause chemotaxis, specific release of cytokines such as IL-8, and lysis of neutrophils and erythrocytes (see Example 1). To analyze whether PSM-mec, which by its size and physico-chemical characteristics forms part of the PSMα-type family, has similar pro-inflammatory and lytic capacities, chemotaxis and calcium flux in human neutrophils was assessed. PSM-mec had lower chemotactic activities (FIG. 21A) and elicited lower calcium flux (FIG. 21B) than the most potent PSMα3, but in a range similar to that detected for other α-type PSMs and in general higher than that of β-type PSMs. The capacity of PSM-mec to activate human neutrophils was determined by measuring surface exposure of gp91phox and CD11b (FIGS. 21D and E). The capacity of PSM-mec to activate human neutrophils was lower than that of the most potent PSMα3, but in the range of the other α-type PSMs and δ-toxin, and higher than that of β-type PSMs. The capacity of PSM-mec to elicit production of the cytokine IL-8 was somewhat higher than that detected for other α-type PSMs, but about in the same range (FIG. 21C). Neutrophil lysis (likely the most crucial immune evasion property of PSMs) was lower in PSM-mec than in other α-type PSMs. However, at 50 µg/ml, neutrophil lysis by PSM-mec obtained approximately the same level (FIG. 21F) as observed previously for other α-type PSMs at 10 µg/ml. Of note, these concentrations are typically achieved by many strains in vitro, indicating that the contribution of PSM-mec to overall cytolytic capacity of PSM-mec producing strains achieves that of PSMα peptides. Finally, lysis of sheep erythrocytes by PSM-mec was in an intermediate range compared to other PSMs (FIG. 21G). These results demonstrated that PSM-mec has pro-inflammatory capacities similar to other α-type PSMs.

PSM-mec Impact on Biofilm Formation and Intercellular Aggregation

Figure 22A:
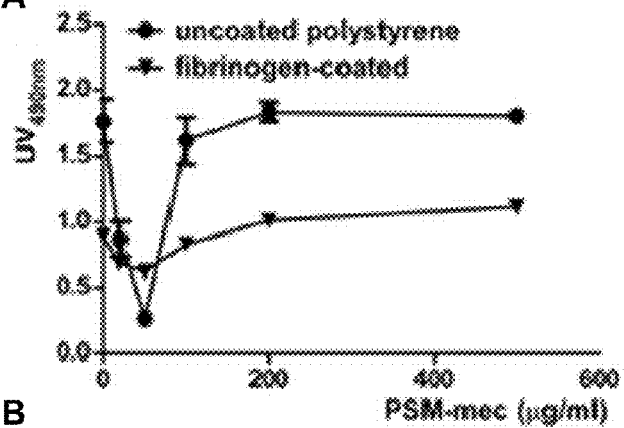
FIG. 22A is a graph showing biofilm formation of PSM-negative *S. aureus* SA113 on uncoated or fibrinogen-coated polystyrene microtiter plates in the presence of increasing concentrations of PSM-mec.

Synthetic PSM-mec was added to the biofilm-positive, agr-negative strain SA113, which lacks PSM production. The impact of PSM-mec on biofilm formation directly on plastic and on fibrinogen-precoated plates (to mimic both possible mechanisms of attachment to indwelling medical devices) was measured (FIG. 22A). In both cases, there was reduced biofilm formation at intermediate PSM-mec concentrations (50 µg/ml), which corresponds to the range of PSM-mec production in bacterial culture filtrates.

Figure 22B:
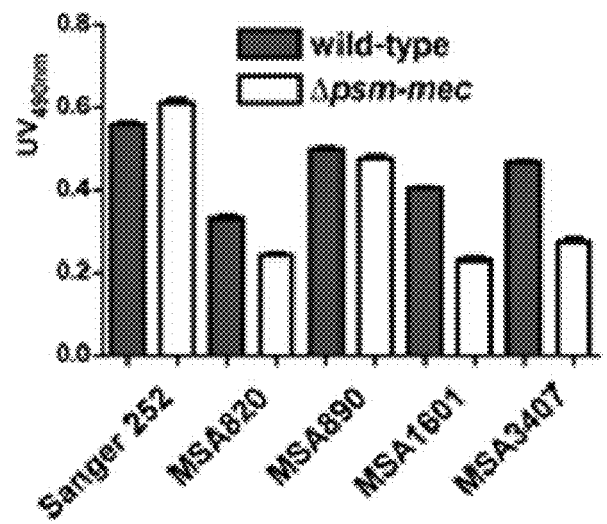
FIG. 22B is a graph showing biofilm formation by *S. aureus* PSM-mec producers (wild-type) in comparison to isogenic psm-mec deletion mutants (Δpsm-mec).
Figure 22C:
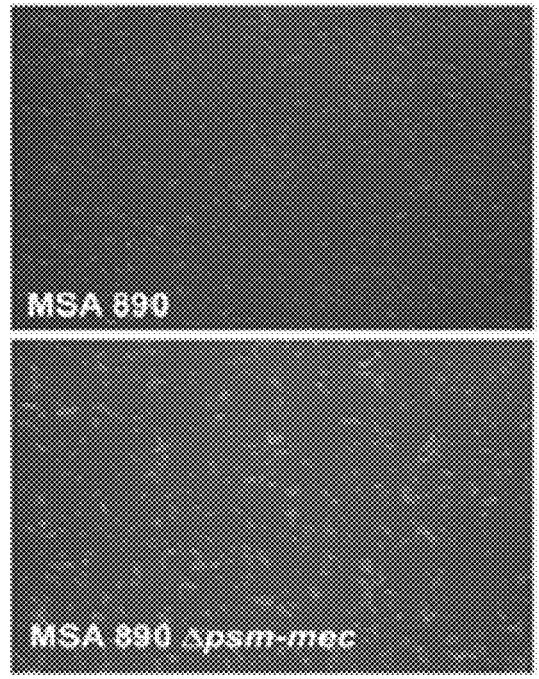
FIG. 22C is a pair of digital images showing aggregation phenotype of *S. aureus* MSA890 and isogenic psm-mec deletion mutant during mid-exponential growth phase (3 h) in shaken TSB flasks.

Isogenic mutants were produced by allelic replacement of the psm-mec gene in strains S. aureus Sanger 252 and the four MRSA strains from the analyzed S. aureus strain collection that showed PSM-mec production (MSA820, MSA890, MSA1601, MSA3407). The isogenic psm-mec deletion mutants were compared with the corresponding wild-type strains. There were slight, yet significant influences on biofilm formation and intercellular aggregation in some strains (FIGS. 22B and C). Together, these results indicate that PSM-mec has a small concentration-dependent capacity to impact adhesion to surfaces, biofilm formation, and intercellular aggregation.

PSM-mec Contributes to Pathogenesis

Figure 23A:
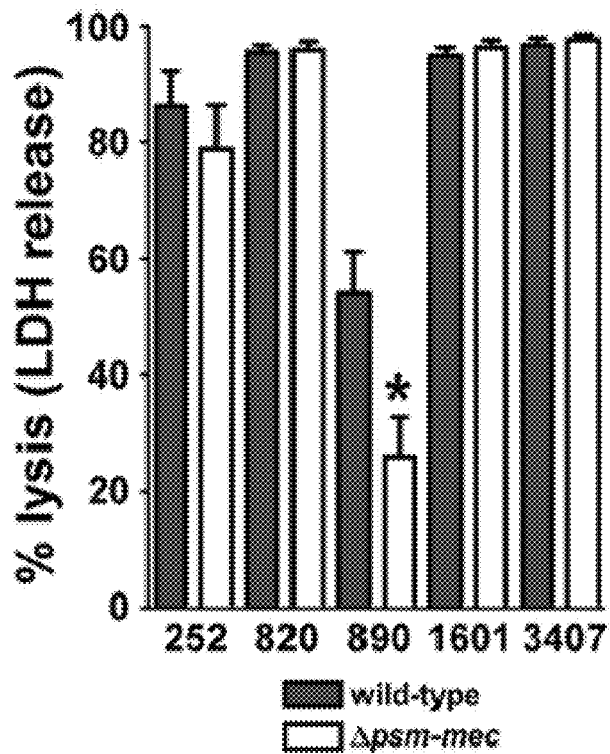
FIG. 23A is a graph showing lysis of human neutrophils by *S. aureus* PSM-mec producers (wild-type) in comparison to isogenic psm-mec deletion mutants (Δpsm-mec). Culture filtrates of strains were mixed with human neutrophils at a 1:10 dilution and lysis was measured after 1 h by release of lactate dehydrogenase (LDH). Values are mean±SEM obtained from neutrophils of 5 independent donors. *, p=0.02 vs. wild-type.
Figure 23B:
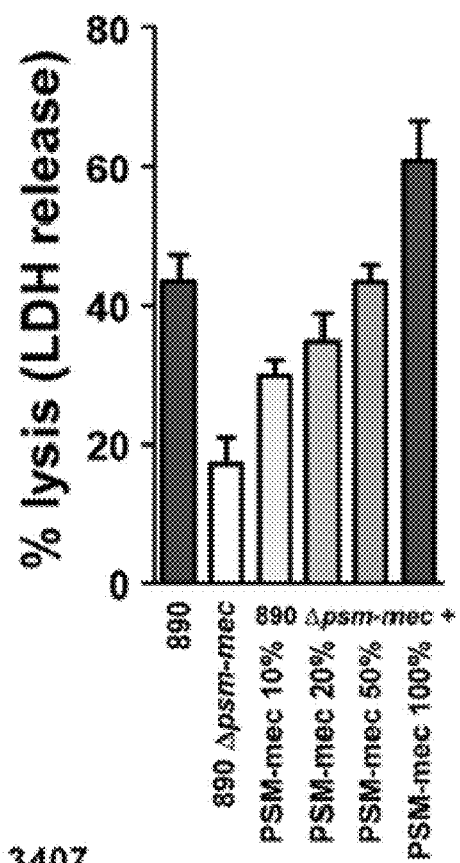
FIG. 23B is a graph showing lysis of human neutrophils in wild-type S. aureus MSA890 and isogenic psm-mec deletion strain with added PSM-mec. PSM-mec was added to culture filtrates of the psm-mec deletion strain in increasing concentrations (10, 20, 50, and 100% of the concentration detected in the wild-type strain). Experimental conditions were the same as in FIG. 23A. Values are mean±SEM obtained from neutrophils of 2 to 4 independent donors.
Figure 23C:
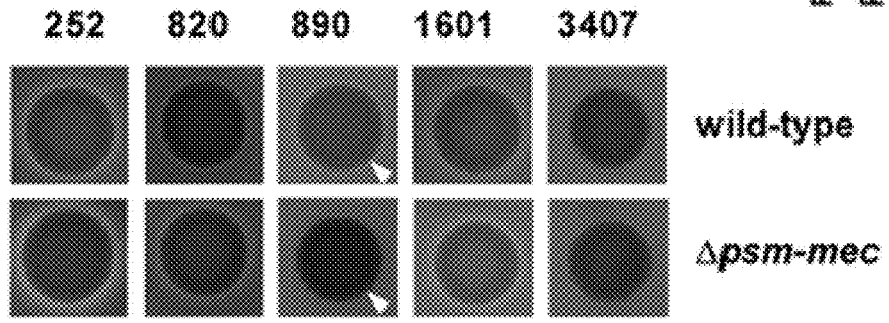
FIG. 23C is a series of digital images showing hemolysis in S. aureus Sanger 252 (252); S. aureus MSA820 (820); S. aureus MSA890 (890); S. aureus MSA1601 (1601); S. aureus MSA3407 (3407) wild-type and isogenic psm-mec deletion strains. Arrowheads mark different zones of synergistic hemolysis in strains S. aureus MSA890 and its isogenic psm-mec deletion mutant.

Neutrophil lysis caused by culture filtrates of the isogenic psm-mec deletion mutant strains compared to those of the corresponding wild-type strains was analyzed. Significantly decreased capacity to lyse human neutrophils was observed in the psm-mec deletion mutant of strain MSA890, but not in the other deletion strains (FIG. 23A). Most likely, this is due to the fact that strain MSA890 produces considerably more relative amounts of PSM-mec, compared to core-genome encoded PSMs, than the other strains (FIG. 20C). Addition of increasing concentrations of PSM-mec to culture filtrates of the MSA890 psm-mec deletion strain, up to 100% of that detected in the wild-type strain under corresponding growth conditions, completely restored the neutrophil-lytic capacity of the MSA890 wild-type strain (FIG. 23B), ruling out the possibility that the observed phenotype was due to unintended second site mutations. Furthermore, pronounced synergistic hemolysis of strain MSA890, a phenotype caused by concerted activity of δ-toxin, other PSM or PSM-like peptides and α-toxin or β-toxin, was considerably reduced by deleting the psm-mec gene in MSA890, whereas no marked reduction was detected in the other isogenic strain pairs (FIG. 23C). These results indicated that PSM-mec production can substitute for the lack of cytolytic capacity in strains such as MSA890, in which expression of genome-encoded cytolytic PSMs is low. Notably, this includes lysis of human neutrophils as likely the most crucial function of PSMs in pathogenesis.

Figure 24A:
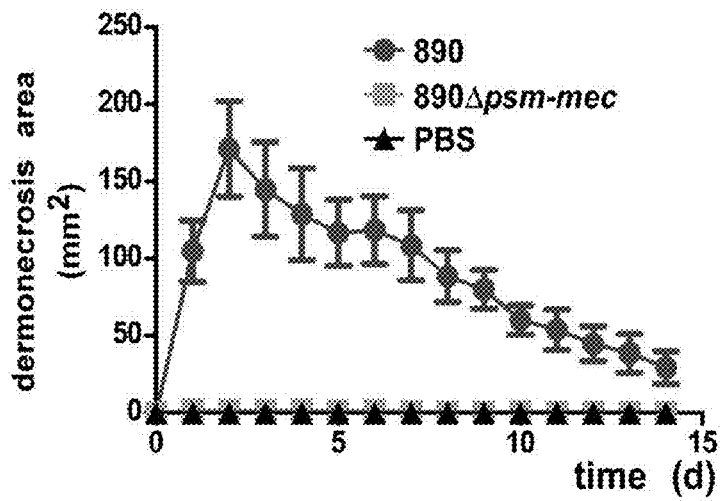
FIG. 24A is a graph showing skin lesion sizes in SKH1-hrBR hairless mice injected subcutaneously with $1\times10^7$ CFUs/50 µl of the indicated strains or phosphate buffered saline as control.
Figure 24B:
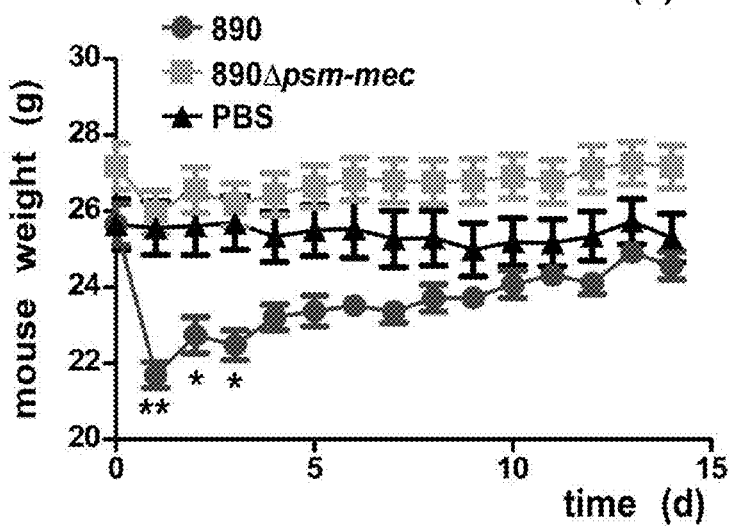
FIG. 24B is a graph showing animal weight in SKH1-hrBR hairless mice injected subcutaneously with $1\times10^7$ CFUs/50 of the indicated strains or phosphate buffered saline as control. *, p<0.05; **, p<0.01, for mice infected with the wild-type strain compared to both other groups.
Figure 24C:
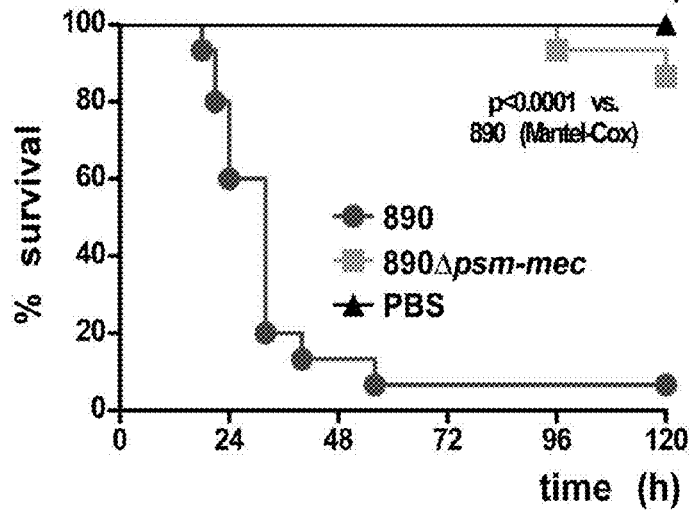
FIG. 24C is a graph showing percent survival in CD1 Swiss female mice injected with $1\times10^8$ CFUs/100 µl of the indicated strains or phosphate buffered saline as control. Disease advancement was measured every 3 h for the first 24 h, then every 8 h for up to 72 h. Number of mice: wild-type strain MSA890, 15; psm-mec deletion strain, 15; PBS control, 5.

Murine bacteremia and skin infection models were used to analyze the impact of psm-mec in pathogenesis. The wild-type and psm-mec deletion mutant pairs of strains S. aureus MSA890 and Sanger 252 were used for these experiments, the latter as an example of the strains in which there was no change in cytolytic activity between psm-mec deletion and wild-type strains. With MSA890 and MSA890Δpsm-mec, very significant differences in lesion size and weight loss were detected in the skin infection model (FIGS. 24A and B) and in animal survival rates in the bacteremia model (FIG. 24C). In contrast, there were no significant differences between strains S. aureus Sanger 252 and Sanger 252Δpsm-mec in the same models. These results are in accordance with those achieved in the neutrophil lysis and hemolysis assays, indicating that the presence of PSM-mec may significantly impact S. aureus pathogenesis when PSM-mec levels exceed those of other cytolytic PSMs.

Example 9

Mutagenesis of PSMα3 Peptide

A series of synthetic PSMα3 peptides were produced in which each amino acid was individually substituted for an alanine (Table 2). The mutant peptides were analyzed for pro-inflammatory activities, including neutrophil lysis, surface expression of CD11b, and secretion of IL-8, using the methods described in Example 2. Wild type PSMα3 lacking N-terminal formylation was also tested.

As shown in Table 2, non-formylated PSMα3 had reduced ability to promote neutrophil lysis and strongly reduced ability to increase CD11b expression, and IL-8 secretion. Several PSMα3 mutants also had reduced pro-inflammatory activity, with #19 (asparagine 21 replaced with alanine; SEQ ID NO: 33) having the greatest reduction in all three activities.

TABLE 2

| Pro-inflammatory activity of PSMα3 mutants | | | | | |
|---|---|---|---|---|---|
| Peptide | Amino acid sequence | SEQ ID NO: | Neutrophil lysis | CD11b | IL-8 |
| PSMα3 | fMEFVAKLFKFFKDLLGKFLGNN | 3 | | | |
| PSMα3, no formyl | MEFVAKLFKFFKDLLGKFLGNN | 3 | x | xx | xx |

TABLE 2-continued

Pro-inflammatory activity of PSMα3 mutants

| Peptide | Amino acid sequence | SEQ ID NO: | Neutrophil lysis | CD11b | IL-8 |
|---|---|---|---|---|---|
| #1 | fMAFVAKLFKFFKDLLGKFLGNN | 14 | xx | x | |
| #2 | fMEAVAKLFKFFKDLLGKFLGNN | 15 | | | |
| #3 | fMEFAAKLFKFFKDLLGKFLGNN | 16 | | | xx |
| #4 | fMEFVAALFKFFKDLLGKFLGNN | 17 | xx | | xx |
| #5 | fMEFVAKAFKFFKDLLGKFLGNN | 18 | xx | | |
| #6 | fMEFVAKLAKFFKDLLGKFLGNN | 19 | | | |
| #7 | fMEFVAKLFAFFKDLLGKFLGNN | 20 | | | xx |
| #8 | fMEFVAKLFKAFKDLLGKFLGNN | 21 | | | |
| #9 | fMEFVAKLFKFAKDLLGKFLGNN | 22 | | | |
| #10 | fMEFVAKLFKFFADLLGKFLGNN | 23 | x | xx | xx |
| #11 | fMEFVAKLFKFFKALLGKFLGNN | 24 | | | xx |
| #12 | fMEFVAKLFKFFKDALGKFLGNN | 25 | | | |
| #13 | fMEFVAKLFKFFKDLAGKFLGNN | 26 | | | |
| #14 | fMEFVAKLFKFFKDLLAKFLGNN | 27 | | | xx |
| #15 | fMEFVAKLFKFFKDLLGAFLGNN | 28 | xx | | xx |
| #16 | fMEFVAKLFKFFKDLLGKALGNN | 29 | | | |
| #17 | fMEFVAKLFKFFKDLLGKFAGNN | 30 | | | |
| #18 | fMEFVAKLFKFFKDLLGKFLANN | 31 | | | |
| #19 | fMEFVAKLFKFFKDLLGKFLGAN | 32 | xx | xx | xx |
| #20 | fMEFVAKLFKFFKDLLGKFLGNA | 33 | x | x | xx | x, reduced activity; xx, strongly reduced activity

In view of the many possible embodiments to which the principles of the disclosure may be applied, it should be recognized that the illustrated embodiments are only preferred examples of the invention and should not be taken as a limitation on the scope of the invention. Rather, the scope of the invention is defined by the following claims. We therefore claim as our invention all that comes within the scope and spirit of these claims.

We claim:

1. An isolated immunogenic peptide comprising at least one antigenic phenol-soluble modulin (PSM) peptide, wherein the PSM peptide is 15-30 amino acids in length and comprises:
   (a) the amino acid sequence set forth as SEQ ID NO: 8;
   (b) the amino acid sequence set forth as SEQ ID NO: 2;
   (c) the amino acid sequence set forth as SEQ ID NO: 3;
   (d) the amino acid sequence set forth as SEQ ID NO: 4;
   (e) the amino acid sequence set forth as SEQ ID NO: 1; or
   (f) the amino acid sequence set forth as SEQ ID NO: 9.

2. The isolated immunogenic peptide of claim 1, wherein the PSM peptide consists of:
   (a) the amino acid sequence set forth as SEQ ID NO: 8;
   (b) the amino acid sequence set forth as SEQ ID NO: 2;
   (c) the amino acid sequence set forth as SEQ ID NO: 3;
   (d) the amino acid sequence set forth as SEQ ID NO: 4;
   (e) the amino acid sequence set forth as SEQ ID NO: 1; or
   (f) the amino acid sequence set forth as SEQ ID NO: 9.

3. The isolated immunogenic peptide of claim 1, wherein the PSM peptide elicits an immune response to methicillin-resistant staphylococcus when administered to a subject in a therapeutically effective amount.

4. The isolated immunogenic peptide of claim 3, wherein the MRSA is community-associated MRSA (CA-MRSA).

5. A pharmaceutical composition comprising a therapeutically effective amount of the immunogenic peptide of claim 1 or a combination thereof, and a pharmaceutically acceptable carrier.

6. The pharmaceutical composition of claim 5, further comprising an amino acid sequence set forth as SEQ ID NO: 6 or SEQ ID NO: 7.

7. The composition of claim 5, further comprising a therapeutically effective amount of an adjuvant.

8. The composition of claim 7, wherein the adjuvant comprises IL-2, RANTES, GM-CSF, G-CSF, TNF-α, IFN-γ, IL-12, or IL-6.

9. A method for eliciting an immune response in a subject, comprising:
   (a) selecting a subject in which an immune response to the immunogenic peptide of claim 1 is desirable; and (b) administering to the subject a therapeutically effective amount of the immunogenic peptide of claim 1 or a combination thereof, thereby producing an immune response in the subject.

10. The method of claim 9, wherein the immunogenic peptide is administered in combination with a therapeutically effective amount of a PSMβ peptide comprising the amino acid sequence set forth as SEQ ID NO: 6 or SEQ ID NO: 7.

11. The method of claim 9, wherein administration comprises oral, topical, mucosal, or parenteral administration.

12. The method of claim 9, wherein administration comprises from about one to about six doses.

13. The method of claim 9, further comprising administering a therapeutically effective amount of an adjuvant to the subject.

14. The method of claim 9, further comprising administering to the subject a therapeutically effective amount of IL-2, RANTES, GM-CSF, G-CSF, TNF-α, IFN-γ, IL-12, IL-6 or a combination thereof.

15. The isolated immunogenic peptide of claim 1, wherein the PSM peptide comprises N-terminal formylation of the PSM peptide.

16. The isolated immunogenic peptide of claim 2, wherein the PSM peptide comprises N-terminal formylation of the PSM peptide.

* * * * *